United States Patent
Tsuboi

(10) Patent No.: US 10,947,522 B2
(45) Date of Patent: Mar. 16, 2021

(54) **MUTANT OF GENUS *RHIZOPUS***

(71) Applicant: Kao Corporation, Tokyo (JP)

(72) Inventor: Yuichi Tsuboi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/074,162

(22) PCT Filed: Feb. 1, 2017

(86) PCT No.: PCT/JP2017/003647
§ 371 (c)(1),
(2) Date: Jul. 31, 2018

(87) PCT Pub. No.: WO2017/135316
PCT Pub. Date: Aug. 10, 2017

(65) Prior Publication Data
US 2019/0352630 A1      Nov. 21, 2019

(30) Foreign Application Priority Data

Feb. 4, 2016 (JP) .............................. JP2016-019676

(51) Int. Cl.
| | | |
|---|---|---|
| *C12P 7/56* | (2006.01) | |
| *C12N 9/88* | (2006.01) | |
| *C12P 7/46* | (2006.01) | |
| *C12P 7/50* | (2006.01) | |
| *C12R 1/845* | (2006.01) | |

(52) U.S. Cl.
CPC .................. *C12N 9/88* (2013.01); *C12P 7/46* (2013.01); *C12P 7/50* (2013.01); *C12P 7/56* (2013.01); *C12R 1/845* (2013.01); *C12Y 401/01001* (2013.01)

(58) Field of Classification Search
None
See application file for complete search history.

(56) References Cited

U.S. PATENT DOCUMENTS

| | | | |
|---|---|---|---|
| 6,268,189 B1 | 7/2001 | Skory | |
| 8,586,526 B2 * | 11/2013 | Gregory | C12N 15/62 514/1.1 |
| 10,253,333 B2 * | 4/2019 | Gregory | C12N 15/62 |
| 2009/0042264 A1 | 2/2009 | Fatland-Bloom et al. | |
| 2015/0125915 A1 | 5/2015 | Tsuboi et al. | |

FOREIGN PATENT DOCUMENTS

| | | |
|---|---|---|
| JP | 09-173090 A | 7/1997 |
| JP | 2002-238590 A | 8/2002 |
| JP | 2005-211042 A | 8/2005 |
| JP | 2017-121184 A | 7/2017 |
| WO | WO 01/72967 A2 | 10/2001 |
| WO | WO 01/73083 A2 | 10/2001 |
| WO | WO 2009/155382 A1 | 12/2009 |
| WO | WO 2013/157398 A1 | 10/2013 |
| WO | WO 2015/017866 A1 | 2/2015 |
| WO | WO 2015/138855 A1 | 9/2015 |

OTHER PUBLICATIONS

Skory et al. (Current Microbiology, vol. 47, pp. 59-64, 2003).*
Thongelhul (Dissertation, 2005, pp. 1-242).*
International Search Report (ISR) for PCT/JP2017/003647; I.A. fd: Feb. 1, 2017, dated May 9, 2017 from the Japan Patent Office, Tokyo, Japan.
International Preliminary Report on Patentability (IPRP), Chapter I of the Patent Cooperation Treaty, including the Written Opinion for PCT/JP2017/003647; I.A. fd: Feb. 1, 2017, dated Aug. 7, 2018, by the International Bureau of WIPO, Geneva, Switzerland.
Fu, Y.-Q. et al., "Strain improvement of *Rhizopus oryzae* for over-production of fumaric acid by reducing ethanol synthesis pathway," Korean Journal of Chemical Engineering, Jan. 2010, vol. 27, Issue 1, pp. 183-186|, First Online: Feb. 16, 2010, The Korean Institute of Chemical Engineers, Seoul, Korea.
Pyruvate decarboxylase isozyme [Rhizopus delemar RA 99-880], database GenBank [online], Mar. 23, 2015, accession No. EIE77072 [retrieval date Apr. 18, 2017], Internet: www.ncbi.nlm.nih.gov/protein/EIE77072.1.
Pyruvate decarboxylase PdcA [Rhizopus oryzae], database GenBank [online], Jul. 14, 2003, accession No. AAM73539 [retrieval date Apr. 20, 2017], Internet: www.ncbi.nlm.nih.gov/protein/AMM73539.1.
Gheinani, AH et al., "RNA silencing of lactate dehydrogenase gene in *Rhizopus oryzae*," J RNAi Gene Silencing. 2011;7:443-8. Epub Jun. 20, 2011, Allied Academies, Candler, NC.
Tsuboi, Y. et al., "Development of gene disruption technique in *Rhizopus oryzae* by programmable nucleases," TALEN, Proceedings of the 2016 Annual Meeting of Japan Society for Bioscience, Biotechnology, and Agrochemistry, Mar. 5, 2016, 3F216, online edition: ISSN 2186-7976.

* cited by examiner

*Primary Examiner* — Hope A Robinson
(74) *Attorney, Agent, or Firm* — Sterne, Kessler, Goldstein & Fox P.L.L.C.

(57) ABSTRACT

The present invention provides a fungus of the genus *Rhizopus* having high productivity of an organic acid. The present invention also provides a mutant of the genus *Rhizopus* with reduced pyruvate decarboxylase activity.

9 Claims, No Drawings

Specification includes a Sequence Listing.

MUTANT OF GENUS *RHIZOPUS*

FIELD OF THE INVENTION

The present invention relates to a mutant of the genus *Rhizopus* and a method for producing an organic acid using the same.

BACKGROUND OF THE INVENTION

Organic acids such as lactic acid, malic acid, succinic acid, and fumaric acid are industrially valuable substances in such a way that these organic acids are used in food production and used as starting materials for synthetic resins or biodegradable polymers.

In recent years, biological production of useful substance using microorganisms or enzymes has been practiced. However, improvement in productivity is one of the important challenges to the industrial production of substances using microorganisms. For the improvement in productivity, the breeding of producers has heretofore been performed by genetic approaches such as mutation. In particular, the development of more efficient microbiological methods for producing substances by use of gene recombination techniques, etc. has received attention with recent progress in microbial genetics and biotechnology.

For example, Patent Literatures 1 to 3 disclose methods for producing lactic acid using a microorganism having a promoter of a filamentous fungus of the genus *Rhizopus* transferred. Also, Non Patent Literature 1 reports a mutant of the genus *Rhizopus* which has a large amount of fumaric acid produced and a small amount of a by-product ethanol produced. Furthermore, Patent Literatures 4 and 5 report that in fumaric acid production in eukaryotes or prokaryotes under particular conditions, the disruption of pyruvate decarboxylase gene or the suppression of pyruvate decarboxylase activity contributes to improvement in fumaric acid productivity. However, the genetic backgrounds of fungi of the genus *Rhizopus* still remain to be fully studied. Hence, at present, it is not easy to develop fungi of the genus *Rhizopus* suitable for useful substance production by gene recombination techniques.

(Patent Literature 1) U.S. Pat. No. 6,268,189
(Patent Literature 2) WO 2001/73083
(Patent Literature 3) WO 2001/72967
(Patent Literature 4) WO 2009/155382
(Patent Literature 5) JP-A-2005-211042
(Non Patent Literature 1) Korean J Chem Eng, 2010, 27 (1): 183-186

SUMMARY OF THE INVENTION

The present invention provides a mutant of the genus *Rhizopus* with reduced pyruvate decarboxylase activity.

The present invention also provides a method for producing a mutant of the genus *Rhizopus*, comprising reducing pyruvate decarboxylase activity in a fungus of the genus *Rhizopus*.

The present invention also provides a method for improving productivity of an organic acid of a fungus of the genus *Rhizopus*, comprising reducing pyruvate decarboxylase activity in the fungus of the genus *Rhizopus*.

The present invention also provides a method for producing an organic acid, comprising culturing the mutant of the genus *Rhizopus*.

DETAILED DESCRIPTION OF THE INVENTION

All patent literatures, non-patent literatures, and other publications cited herein are incorporated herein by reference in their entirety.

In the present specification, nucleotide sequence or amino acid sequence identity is calculated by the Lipman-Pearson method (Science, 1985, 227: 1435-1441). Specifically, the identity is calculated by conducting analysis with Unit size to compare (ktup) set to 2 using the homology analysis (search homology) program of gene information processing software Genetyx-Win.

In the present specification, the term "at least 80% identity" as to an amino acid sequence or a nucleotide sequence refers to 80% or higher, preferably 85% or higher, more preferably 90% or higher, further preferably 95% or higher, still further preferably 97% or higher, still further preferably 98% or higher, still further preferably 99% or higher identity. In the present specification, the term "at least 85% identity" as to an amino acid sequence or a nucleotide sequence refers to 85% or higher, preferably 90% or higher, more preferably 95% or higher, further preferably 97% or higher, still further preferably 98% or higher, still further preferably 99% or higher identity. In the present specification, the term "at least 95% identity" as to an amino acid sequence or a nucleotide sequence refers to 95% or higher, preferably 97% or higher, more preferably 98% or higher, further preferably 99% or higher identity.

In the present specification, examples of the "amino acid sequence having deletion, insertion, substitution or addition of one or more amino acids" include amino acid sequences having deletion, insertion, substitution or addition of 1 or more and 30 or less, preferably 1 or more and 20 or less, more preferably 1 or more and 10 or less, further preferably 1 or more and 5 or less, still further preferably 1 or more and 3 or less amino acids. In the present specification, examples of the "nucleotide sequence having deletion, insertion, substitution or addition of one or more nucleotides" include nucleotide sequences having deletion, insertion, substitution or addition of 1 or more and 90 or less, preferably 1 or more and 60 or less, more preferably 1 or more and 30 or less, further preferably 1 or more and 15 or less, still further preferably 1 or more and 10 or less nucleotides. In the present specification, the "addition" of an amino acid or a nucleotide includes the addition of one or more amino acids or nucleotides to one end and both ends of a sequence.

In the present specification, the term "operable linking" between a control region and a gene refers to the linking between the gene and the control region such that the gene can be expressed under control of the control region. The procedures of the "operable linking" between a gene and a control region are well known to those skilled in the art.

In the present specification, the terms "upstream" and "downstream" as to a gene refer to upstream and downstream in the direction of transcription of the gene unless otherwise specified.

In the present specification, the term "position corresponding" or "region corresponding" on an amino acid sequence or a nucleotide sequence can be determined by aligning a sequence of interest and a reference sequence (e.g., the amino acid sequence represented by SEQ ID NO: 11) so as to provide the maximum homology. The alignment of amino acid sequences or nucleotide sequences can be carried out using an algorithm known in the art, and the procedures thereof are known to those skilled in the art. For example, the alignment can also be manually performed on the basis of the Lipman-Pearson method mentioned above or the like and can be performed by using the default setting of Clustal W multiple alignment program (Thompson, J. D. et al., 1994, Nucleic Acids Res. 22: 4673-4680). Alternatively, Clustal W2 or Clustal omega, a modified version of Clustal W, may be used. These programs Clustal W, Clustal W2 and Clustal omega are available on the website of, for example, the European Bioinformatics Institute: EBI [www.ebi.ac.uk/index.html] or the DNA Data Bank of Japan (DDBJ [www.ddbj.nig.ac.jp/searches-j.html]) run by the National Institute of Genetics Japan. The position or the region in the sequence of interest aligned in response to an arbitrary region in the reference sequence by the alignment mentioned above is regarded as the "position corresponding" or "region corresponding" to the arbitrary region.

In the present specification, the term "pdc gene" is a gene encoding pyruvate decarboxylase and refers to a gene selected from the group consisting of: a polynucleotide consisting of the nucleotide sequence represented by SEQ ID NO: 1; a polynucleotide consisting of a nucleotide sequence having at least 80% identity to the nucleotide sequence represented by SEQ ID NO: 1, and encoding a polypeptide which has pyruvate decarboxylase activity; and a polynucleotide consisting of a nucleotide sequence having deletion, insertion, substitution or addition of one or more nucleotides with respect to the nucleotide sequence represented by SEQ ID NO: 1, and encoding a polypeptide which has pyruvate decarboxylase activity. Examples of the polynucleotide consisting of the nucleotide sequence represented by SEQ ID NO: 1 include a gene encoding pyruvate decarboxylase 1 (PDC1) (SEQ ID NO: 2) derived from *Rhizopus delemar*.

Thus, the "pdc gene" in the present specification also refers to a gene selected from the group consisting of: a polynucleotide encoding a polypeptide which consists of the amino acid sequence represented by SEQ ID NO: 2; a polynucleotide encoding a polypeptide which consists of an amino acid sequence having at least 80% identity to the amino acid sequence represented by SEQ ID NO: 2 and has pyruvate decarboxylase activity; and a polynucleotide encoding a polypeptide which consists of an amino acid sequence having deletion, insertion, substitution or addition of one or more amino acid residues with respect to the amino acid sequence represented by SEQ ID NO: 2 and has pyruvate decarboxylase activity.

In the present specification, the term "reduction of pyruvate decarboxylase activity" in a microbial mutant refers to the reduction of the pyruvate decarboxylase activity in the microbial mutant to 50% or less, preferably 20% or less, more preferably 15% or less, of the activity of the strain before the mutation (parent strain). The pyruvate decarboxylase activity of a microorganism can be measured according to a method described in Examples mentioned later.

The present invention relates to a provision of a mutant of the genus *Rhizopus* having high productivity of an organic acid, and a method for producing an organic acid using the same.

The present inventors conducted studies on improvement in productivity of an organic acid of a fungus of the genus *Rhizopus*. As a result, the present inventors found that a fungus of the genus *Rhizopus* with reduced pyruvate decarboxylase activity has remarkably improved productivity of an organic acid and completed the present invention.

The present invention provides a mutant of the genus *Rhizopus* having high productivity of an organic acid. The mutant of the genus *Rhizopus* of the present invention achieves efficient microbiological production of an organic acid.

The mutant of the genus *Rhizopus* of the present invention is a mutant of the genus *Rhizopus* with reduced pyruvate decarboxylase activity.

Examples of the parent strain of the mutant of the genus *Rhizopus* of the present invention include filamentous fungi belonging to the genus *Rhizopus*, for example, *Rhizopus oryzae*, *Rhizopus arrhizus*, *Rhizopus chinensis*, *Rhizopus nigricans*, *Rhizopus tonkinensis*, *Rhizopus tritici*, and *Rhizopus delemar*. Among them, *Rhizopus oryzae* and *Rhizopus delemar* are preferred, and *Rhizopus delemar* is more preferred. The mutant of the genus *Rhizopus* of the present invention can be prepared by modifying the parent strain so as to reduce pyruvate decarboxylase activity.

The reduction of pyruvate decarboxylase activity in the fungus of the genus *Rhizopus* can be achieved by decreasing the expression level of pyruvate decarboxylase in the cells of the fungus of the genus *Rhizopus*. The pyruvate decarboxylase activity can be reduced, for example, by deleting or inactivating the pdc gene of the fungus of the genus *Rhizopus*, by inactivating mRNA transcribed from the pdc gene, or by inhibiting the translation of the mRNA of the pdc gene to a protein. The "pdc gene" to be deleted or inactivated according to the present invention is as defined above. Even if a different gene, for example, a pyruvate decarboxylase-encoding gene shown in SEQ ID NO: 83 (in the present specification, also referred to as pdc3 gene in some cases), is deleted or inactivated, the "reduction of pyruvate decarboxylase activity" defined in the present specification cannot be achieved. Thus, the effect of improving the productivity of an organic acid according to the present invention cannot be sufficiently obtained. Alternatively, the pyruvate decarboxylase activity may be reduced by decreasing the activity of the pyruvate decarboxylase expressed in the fungus of the genus *Rhizopus*. The modification described above can be artificially performed by use of a molecular biological or genetic engineering approach.

Examples of the method for inactivating the mRNA of the pdc gene in the cells include target-specific mRNA inhibition using siRNA. Basic procedures for the siRNA are well known to those skilled in the art (see, for example, JP-A-2007-512808). Also, a reagent or a kit for the siRNA is commercially available. Those skilled in the art can prepare the desired target-specific siRNA on the basis of a literature known in the art or the manual of a commercially available product and inhibit the target mRNA.

Examples of the method for decreasing the pyruvate decarboxylase activity include a method using a PDC inhibitor. Examples of the PDC inhibitor include omeprazole (see, for example, Biochem. Pharmacol, 44: 177-179).

Examples of the method for deleting or inactivating the pdc gene in the cells include a method of removing a portion or the whole of the nucleotide sequence of the pdc gene from the genome or replacing a portion or the whole of this nucleotide sequence with a different nucleotide sequence, a method of inserting a different polynucleotide fragment into the sequence of the pdc gene, and a method of adding a mutation to the transcription or translation initiation region of the pdc gene. Preferably, a portion or the whole of the nucleotide sequence of the pdc gene is deleted. More specific examples thereof include a method of specifically deleting or inactivating the pdc gene on the genome of the cells, and a method of adding random deletion or inactivation mutations to genes in the cells and then selecting cells having the desired mutation by expression level or activity evaluation on pyruvate decarboxylase encoded by the pdc gene, or gene analysis.

Examples of the method for randomly deleting or inactivating genes in the cells include a method of transferring randomly cloned DNA fragments of inactivated genes to the cells and causing homologous recombination between the transferred DNA fragments and genes on the genome of the cells, and a method of irradiating the cells with ultraviolet ray, γ-ray, or the like to induce mutation. The method for preparing the inactivated genes includes site-directed mutagenesis. A commercially available kit such as Site-Directed Mutagenesis System Mutan-SuperExpress Km kit (Takara Bio Inc.), Transformer™ Site-Directed Mutagenesis kit (Clontech Laboratories, Inc.), or KOD-Plus-Mutagenesis Kit (Toyobo Co., Ltd.) can be used. The cells with the pdc gene deleted or inactivated can be selected by confirming the genomic sequences of the cells having random mutations obtained by the method described above. Alternatively, the cells with the pdc gene deleted or inactivated can be selected by using the pyruvate decarboxylase expression levels or activity of the cells as an index.

Examples of the method for specifically deleting or inactivating the gene in the genome include, but are not limited to, genome editing using programmable nuclease (artificial DNA nuclease).

In a preferred embodiment, the deletion or inactivation of the pdc gene in the fungus of the genus *Rhizopus* according to the present invention is performed by the genome editing of a pdc gene locus. In the present specification, the "pdc gene locus" refers to a region on the genome containing the DNA sequence of the pdc gene, a 1,000-bp region on the 5' end thereof and a 1,000-bp region on the 3' end thereof.

The genome editing is a technique of modifying the genome in a site-directed manner by specifically cleaving the DNA duplex of a target gene locus on the genome and inducing deletion, insertion or substitution of nucleotides in the course of repair of the cleaved DNA or inserting a foreign polynucleotide thereto, for example. Such a technique is known as TALEN (transcription activator-like effector nuclease), ZFN (zinc-finger nuclease), CRISPR (clustered regularly interspaced short palindromic repeat)-Cas9 system, homing endonuclease, compact designer TALEN, etc. (Nature Reviews Genetics, 2014, 15: 321-334; Nucleic Acids Research, 2011, 39: e82; Nucleic Acids Research, 2006, 34: e149; and Nature communications, 2013, 4: 1762). A kit for the genome editing based on these techniques is commercially available and can be purchased from, for example, Life Technologies Corp., Cellectis, or Transposagen Biopharmaceuticals, Inc.

TALEN will be described in detail for the purpose of merely illustrating the genome editing technology. TALEN is a protein which has a transcription activator-like (TAL) effector derived from a DNA binding domain of plant pathogenic bacteria of the genus *Xanthomonas*, and a DNA cleavage domain consisting of DNA nuclease Fok1. The TAL effector of TALEN has a structure in which approximately 17 repeat sequences (repeats) each consisting of approximately 34 amino acids are linked. Each repeat recognizes one nucleotide. The type of the base specifically recognized by each repeat depends on the type of two consecutive amino acid residues (repeat-variable diresidues; referred to as RVDs) located at particular positions in the repeat. The types of amino acid residue pairs of RVDs suiting four bases A, T, G and C are known in the art. Thus, those skilled in the art can construct TALEN specifically recognizing a target genomic DNA sequence. The genome editing using TALEN involves designing one set of TALENs respectively specifically recognizing upstream and downstream sequences near a genomic DNA region to be cleaved, and intracellularly expressing the TALENs. In general, genes encoding target-specific TALENs are constructed and transferred to cells, followed by intracellular expression of the TALENs. Upon binding of the expressed TALENs to suiting genomic DNA, the Fok1 contained therein form a dimer on the target genomic DNA region to be cleaved and thereby cleave the DNA duplex.

Examples of the TALENs for the deletion or inactivation of the pdc gene in the fungus of the genus *Rhizopus* include a pair of TALENs consisting of the following polypeptides (L) and (R):

The polypeptide (L) is a TALEN polypeptide which has a TAL effector targeting the sequence represented by 5'-TGCCTGCTATTAAAATCG-3' (SEQ ID NO: 9) in the sense strand of the pdc gene and a DNA cleavage domain consisting of Fok1-like DNA nuclease. Preferably, the TAL effector contained in the polypeptide (L) (hereinafter, also referred to as a TAL effector (L)) contains a polypeptide in which 17 repeat sequences (repeats) are linked and recognizes the sequence represented by 5'-TGCCTGCTAT-TAAAATCG-3' (SEQ ID NO: 9).

The polypeptide (R) is a TALEN polypeptide which has a TAL effector targeting the sequence represented by 5'-TT-GATTTCCTTAAGACGG-3' (SEQ ID NO: 10) in the antisense strand of the pdc gene and a DNA cleavage domain consisting of Fok1-like DNA nuclease. Preferably, the TAL effector contained in the polypeptide (R) (hereinafter, also referred to as a TAL effector (R)) contains a polypeptide in which 17 repeat sequences (repeats) are linked and recognizes the sequence represented by 5'-TTGATTTCCTTAA-GACGG-3' (SEQ ID NO: 10).

The 1st to 16th repeats counted from the upstream end among the 17 repeats in the TAL effector (L) each consist of an amino acid sequence having at least 85% identity to the amino acid sequence represented by SEQ ID NO: 11, or consist of an amino acid sequence having deletion, insertion, substitution or addition of 5 or less amino acid residues with respect to the amino acid sequence represented by SEQ ID NO: 11. Preferably, the 1st to 16th repeats counted from the upstream end each consist of an amino acid sequence having deletion, insertion, substitution or addition of 3 or less amino acid residues in a site other than RVDs mentioned later with respect to the amino acid sequence represented by SEQ ID NO: 11. The 17th repeat (most downstream repeat) among the repeats in the TAL effector (L) consists of an amino acid sequence having at least 95% identity to the amino acid sequence represented by SEQ ID NO: 27.

The 1st to 16th repeats counted from the upstream end among the 17 repeats in the TAL effector (R) each consist of an amino acid sequence having at least 85% identity to the amino acid sequence represented by SEQ ID NO: 28, or consist of an amino acid sequence having deletion, insertion, substitution or addition of 5 or less amino acid residues with respect to the amino acid sequence represented by SEQ ID NO: 28. Preferably, the 1st to 16th repeats counted from the upstream end each consist of an amino acid sequence having deletion, insertion, substitution or addition of 3 or less amino acid residues in a site other than RVDs mentioned later with respect to the amino acid sequence represented by SEQ ID NO: 28. The 17th repeat (most downstream repeat) among the repeats in the TAL effector (R) consists of an amino acid sequence having at least 95% identity to the amino acid sequence represented by SEQ ID NO: 44.

Preferably, the 17 repeats in the TAL effector (L) each have two amino acid residues (repeat-variable diresidues; RVDs) serving as a base recognition site at positions corresponding to amino acid positions 12 and 13 of the amino acid sequence represented by SEQ ID NO: 11, and the respective RVDs of the repeats recognize bases at positions 2 to 18 of the sequence represented by SEQ ID NO: 9. Also preferably, the 17 repeats in the TAL effector (R) each have RVDs at positions corresponding to amino acid positions 12 and 13 of the amino acid sequence represented by SEQ ID NO: 28, and the respective RVDs of the repeats recognize bases at positions 2 to 18 of the sequence represented by SEQ ID NO: 10. The types of amino acid residues of the RVDs depend on the types of targeted bases, as shown below.

| Target base | RVDs |
|---|---|
| A | NI |
| C | HD |
| G/A | NN |
| T | NG |

However, two or less, preferably one, of the 17 repeats may not have the RVD suiting SEQ ID NO: 9 as long as the TAL effector (L) can recognize the sequence represented by SEQ ID NO: 9. In other words, 15 or more, preferably 16 or more, of the 17 repeats may have the RVDs suiting SEQ ID NO: 9. Also, two or less, preferably one, of the 17 repeats may not have the RVD suiting SEQ ID NO: 10 as long as the TAL effector (R) can recognize the sequence represented by SEQ ID NO: 10. In other words, 15 or more, preferably 16 or more, of the 17 repeats may have the RVDs suiting SEQ ID NO: 10.

In a more preferred embodiment, the 17 repeats of the TAL effector (L) respectively consist of the following amino acid sequences (1) to (17) in order from the upstream end:
(1) the amino acid sequence represented by SEQ ID NO: 11, or an amino acid sequence having at least 95% identity thereto;
(2) the amino acid sequence represented by SEQ ID NO: 12, or an amino acid sequence having at least 95% identity thereto;
(3) the amino acid sequence represented by SEQ ID NO: 13, or an amino acid sequence having at least 95% identity thereto;
(4) the amino acid sequence represented by SEQ ID NO: 14, or an amino acid sequence having at least 95% identity thereto;
(5) the amino acid sequence represented by SEQ ID NO: 15, or an amino acid sequence having at least 95% identity thereto;
(6) the amino acid sequence represented by SEQ ID NO: 16, or an amino acid sequence having at least 95% identity thereto;
(7) the amino acid sequence represented by SEQ ID NO: 17, or an amino acid sequence having at least 95% identity thereto;
(8) the amino acid sequence represented by SEQ ID NO: 18, or an amino acid sequence having at least 95% identity thereto;
(9) the amino acid sequence represented by SEQ ID NO: 19, or an amino acid sequence having at least 95% identity thereto;
(10) the amino acid sequence represented by SEQ ID NO: 20, or an amino acid sequence having at least 95% identity thereto;
(11) the amino acid sequence represented by SEQ ID NO: 21, or an amino acid sequence having at least 95% identity thereto;
(12) the amino acid sequence represented by SEQ ID NO: 22, or an amino acid sequence having at least 95% identity thereto;
(13) the amino acid sequence represented by SEQ ID NO: 23, or an amino acid sequence having at least 95% identity thereto;
(14) the amino acid sequence represented by SEQ ID NO: 24, or an amino acid sequence having at least 95% identity thereto;
(15) the amino acid sequence represented by SEQ ID NO: 25, or an amino acid sequence having at least 95% identity thereto;
(16) the amino acid sequence represented by SEQ ID NO: 26, or an amino acid sequence having at least 95% identity thereto; and
(17) the amino acid sequence represented by SEQ ID NO: 27, or an amino acid sequence having at least 95% identity thereto.

Preferably, the amino acid sequences (1) to (17) respectively have RVDs consisting of the following amino acid residue pairs:
(1) amino acid residues NN (guanine recognition site) at positions corresponding to amino acid positions 12 and 13 of SEQ ID NO: 11;
(2) amino acid residues HD (cytosine recognition site) at positions corresponding to amino acid positions 12 and 13 of SEQ ID NO: 12;
(3) amino acid residues HD (cytosine recognition site) at positions corresponding to amino acid positions 12 and 13 of SEQ ID NO: 13;
(4) amino acid residues NG (thymine recognition site) at positions corresponding to amino acid positions 12 and 13 of SEQ ID NO: 14;
(5) amino acid residues NN (guanine recognition site) at positions corresponding to amino acid positions 12 and 13 of SEQ ID NO: 15;
(6) amino acid residues HD (cytosine recognition site) at positions corresponding to amino acid positions 12 and 13 of SEQ ID NO: 16;
(7) amino acid residues NG (thymine recognition site) at positions corresponding to amino acid positions 12 and 13 of SEQ ID NO: 17;
(8) amino acid residues NI (adenine recognition site) at positions corresponding to amino acid positions 12 and 13 of SEQ ID NO: 18;
(9) amino acid residues NG (thymine recognition site) at positions corresponding to amino acid positions 12 and 13 of SEQ ID NO: 19;
(10) amino acid residues NG (thymine recognition site) at positions corresponding to amino acid positions 12 and 13 of SEQ ID NO: 20;
(11) amino acid residues NI (adenine recognition site) at positions corresponding to amino acid positions 12 and 13 of SEQ ID NO: 21;
(12) amino acid residues NI (adenine recognition site) at positions corresponding to amino acid positions 12 and 13 of SEQ ID NO: 22;
(13) amino acid residues NI (adenine recognition site) at positions corresponding to amino acid positions 12 and 13 of SEQ ID NO: 23;
(14) amino acid residues NI (adenine recognition site) at positions corresponding to amino acid positions 12 and 13 of SEQ ID NO: 24;

(15) amino acid residues NG (thymine recognition site) at positions corresponding to amino acid positions 12 and 13 of SEQ ID NO: 25;
(16) amino acid residues HD (cytosine recognition site) at positions corresponding to amino acid positions 12 and 13 of SEQ ID NO: 26; and
(17) amino acid residues NN (guanine recognition site) at positions corresponding to amino acid positions 12 and 13 of SEQ ID NO: 27.

However,
15 or more, preferably 16 or more, of the repeats (1) to (17) may have the RVDs described above as long as the TAL effector (L) can recognize the sequence represented by 5'-TGCCTGCTATTAAAATCG-3' (SEQ ID NO: 9).

In another more preferred embodiment, the 17 repeats of the TAL effector (R) respectively consist of the following amino acid sequences (1') to (17') in order from the upstream end:
(1') the amino acid sequence represented by SEQ ID NO: 28, or an amino acid sequence having at least 95% identity thereto;
(2') the amino acid sequence represented by SEQ ID NO: 29, or an amino acid sequence having at least 95% identity thereto;
(3') the amino acid sequence represented by SEQ ID NO: 30, or an amino acid sequence having at least 95% identity thereto;
(4') the amino acid sequence represented by SEQ ID NO: 31, or an amino acid sequence having at least 95% identity thereto;
(5') the amino acid sequence represented by SEQ ID NO: 32, or an amino acid sequence having at least 95% identity thereto;
(6') the amino acid sequence represented by SEQ ID NO: 33, or an amino acid sequence having at least 95% identity thereto;
(7') the amino acid sequence represented by SEQ ID NO: 34, or an amino acid sequence having at least 95% identity thereto;
(8') the amino acid sequence represented by SEQ ID NO: 35, or an amino acid sequence having at least 95% identity thereto;
(9') the amino acid sequence represented by SEQ ID NO: 36, or an amino acid sequence having at least 95% identity thereto;
(10') the amino acid sequence represented by SEQ ID NO: 37, or an amino acid sequence having at least 95% identity thereto;
(11') the amino acid sequence represented by SEQ ID NO: 38, or an amino acid sequence having at least 95% identity thereto;
(12') the amino acid sequence represented by SEQ ID NO: 39, or an amino acid sequence having at least 95% identity thereto;
(13') the amino acid sequence represented by SEQ ID NO: 40, or an amino acid sequence having at least 95% identity thereto;
(14') the amino acid sequence represented by SEQ ID NO: 41, or an amino acid sequence having at least 95% identity thereto;
(15') the amino acid sequence represented by SEQ ID NO: 42, or an amino acid sequence having at least 95% identity thereto;
(16') the amino acid sequence represented by SEQ ID NO: 43, or an amino acid sequence having at least 95% identity thereto; and
(17') the amino acid sequence represented by SEQ ID NO: 44, or an amino acid sequence having at least 95% identity thereto.

Preferably, the amino acid sequences (1') to (17') respectively have RVDs consisting of the following amino acid residue pairs:
(1') amino acid residues NG (thymine recognition site) at positions corresponding to amino acid positions 12 and 13 of SEQ ID NO: 28;
(2') amino acid residues NN (guanine recognition site) at positions corresponding to amino acid positions 12 and 13 of SEQ ID NO: 29;
(3') amino acid residues NI (adenine recognition site) at positions corresponding to amino acid positions 12 and 13 of SEQ ID NO: 30;
(4') amino acid residues NG (thymine recognition site) at positions corresponding to amino acid positions 12 and 13 of SEQ ID NO: 31;
(5') amino acid residues NG (thymine recognition site) at positions corresponding to amino acid positions 12 and 13 of SEQ ID NO: 32;
(6') amino acid residues NG (thymine recognition site) at positions corresponding to amino acid positions 12 and 13 of SEQ ID NO: 33;
(7') amino acid residues HD (cytosine recognition site) at positions corresponding to amino acid positions 12 and 13 of SEQ ID NO: 34;
(8') amino acid residues HD (cytosine recognition site) at positions corresponding to amino acid positions 12 and 13 of SEQ ID NO: 35;
(9') amino acid residues NG (thymine recognition site) at positions corresponding to amino acid positions 12 and 13 of SEQ ID NO: 36;
(10') amino acid residues NG (thymine recognition site) at positions corresponding to amino acid positions 12 and 13 of SEQ ID NO: 37;
(11') amino acid residues NI (adenine recognition site) at positions corresponding to amino acid positions 12 and 13 of SEQ ID NO: 38;
(12') amino acid residues NI (adenine recognition site) at positions corresponding to amino acid positions 12 and 13 of SEQ ID NO: 39;
(13') amino acid residues NN (guanine recognition site) at positions corresponding to amino acid positions 12 and 13 of SEQ ID NO: 40;
(14') amino acid residues NI (adenine recognition site) at positions corresponding to amino acid positions 12 and 13 of SEQ ID NO: 41;
(15') amino acid residues HD (cytosine recognition site) at positions corresponding to amino acid positions 12 and 13 of SEQ ID NO: 42;
(16') amino acid residues NN (guanine recognition site) at positions corresponding to amino acid positions 12 and 13 of SEQ ID NO: 43; and
(17') amino acid residues NN (guanine recognition site) at positions corresponding to amino acid positions 12 and 13 of SEQ ID NO: 44.

However, 15 or more, preferably 16 or more, of the repeats (1') to (17') may have the RVDs described above as long as the TAL effector (R) can recognize the sequence represented by 5'-TTGATTTCCTTAAGACGG-3' (SEQ ID NO: 10).

The Fok1-like DNA nuclease contained in each of the polypeptides (L) and (R) refers to a nuclease which functions as DNA endonuclease through dimerization. Preferably, the Fok1-like DNA nuclease is a nuclease which is encoded by a sequence represented by nucleotide positions 2,416 to 3,006 of SEQ ID NO: 3 or a polynucleotide consisting of a sequence at least 95% identical thereto, and functions as DNA endonuclease through dimerization.

Preferred examples of the polypeptides (L) and (R) include:
the polypeptide (L) being
  a polypeptide which consists of the amino acid sequence represented by SEQ ID NO: 4; or
  a polypeptide which consists of an amino acid sequence having at least 95% identity to the amino acid sequence represented by SEQ ID NO: 4 and has the TAL effector (L) targeting the sequence represented by SEQ ID NO: 9 and a DNA cleavage domain consisting of the Fok1-like DNA nuclease, and
the polypeptide (R) being
  a polypeptide which consists of the amino acid sequence represented by SEQ ID NO: 6; or
  a polypeptide which consists of an amino acid sequence having at least 95% identity to the amino acid sequence represented by SEQ ID NO: 6 and has the TAL effector (R) targeting the sequence represented by SEQ ID NO: 10 and a DNA cleavage domain consisting of the Fok1-like DNA nuclease.

Other preferred examples of the polypeptides (L) and (R) include polypeptides which are encoded by the following polynucleotides (l) and (r), respectively: the polynucleotide (l) being
  a polynucleotide consisting of the nucleotide sequence represented by SEQ ID NO: 3; or
  a polynucleotide consisting of a nucleotide sequence having at least 95% identity to the nucleotide sequence represented by SEQ ID NO: 3, and encoding a polypeptide which has the TAL effector (L) targeting the sequence represented by SEQ ID NO: 9 and a DNA cleavage domain consisting of the Fok1-like DNA nuclease, and the polynucleotide (r) being
  a polynucleotide consisting of the nucleotide sequence represented by SEQ ID NO: 5; or
  a polynucleotide consisting of a nucleotide sequence having at least 95% identity to the nucleotide sequence represented by SEQ ID NO: 5, and encoding a polypeptide which has the TAL effector (R) targeting the sequence represented by SEQ ID NO: 10 and a DNA cleavage domain consisting of the Fok1-like DNA nuclease.

In a preferred embodiment, the polypeptide (L) is a polypeptide which consists of the amino acid sequence represented by SEQ ID NO: 4, or a polypeptide which is encoded by a polynucleotide consisting of the nucleotide sequence represented by SEQ ID NO: 3. Also, in a preferred embodiment, the polypeptide (R) is a polypeptide which consists of the amino acid sequence represented by SEQ ID NO: 6, or a polypeptide which is encoded by a polynucleotide consisting of the nucleotide sequence represented by SEQ ID NO: 5.

The TALENs consisting of the polypeptides (L) and (R) respectively specifically bind to the sense strand and the antisense strand of DNA (SEQ ID NO: 81) containing the pdc gene locus on the genome of the fungus of the genus *Rhizopus* and cleave the DNA of the pdc gene locus so that the pdc gene is deleted or inactivated.

Thus, in a preferred embodiment, the mutant of the genus *Rhizopus* of the present invention is prepared by transferring the polypeptides (L) and (R) or polynucleotides encoding the polypeptides (L) and (R) to a parent strain fungus of the genus *Rhizopus* and thereby deleting or inactivating the pdc gene of the fungus of the genus *Rhizopus*. Preferred examples of the polynucleotides encoding the polypeptides (L) and (R) include the polynucleotides (l) and (r), respectively, mentioned above.

The disruption of target DNA of a programmable nuclease such as TALEN is promoted by intracellularly expressing a foreign exonuclease together with the programmable nuclease (Scientific Reports, 2013, 3: 1253, DOI: 10.1038/srep01253; and Nat Methods, 2012, 9: 973-975). Thus, in a preferred embodiment of the present invention, in addition to the TALEN peptides or the polynucleotides encoding the TALEN peptides, an exonuclease or a polynucleotide encoding the exonuclease is further transferred to the parent strain fungus of the genus *Rhizopus*. The exonuclease is not particularly limited as long as the exonuclease is derived from a filamentous fungus. Examples thereof include preferably an exonuclease derived from a fungus of the genus *Rhizopus*, more preferably one belonging to exonuclease 1 or exonuclease 2, further preferably an exonuclease derived from *Rhizopus oryzae* or *Rhizopus delemar*.

Further preferred examples of the exonuclease include a *Rhizopus oryzae*-derived exonuclease (SEQ ID NO: 8) encoded by a polynucleotide consisting of the nucleotide sequence represented by SEQ ID NO: 7 or SEQ ID NO: 82. Thus, further preferred examples of the exonuclease which is used in the present invention include: a polypeptide which consists of the amino acid sequence represented by SEQ ID NO: 8; a polypeptide which consists of an amino acid sequence having at least 95% identity to the amino acid sequence represented by SEQ ID NO: 8 and has exonuclease activity; a polypeptide which is encoded by a polynucleotide consisting of the nucleotide sequence represented by SEQ ID NO: 7; a polypeptide which is encoded by a polynucleotide consisting of a nucleotide sequence having at least 95% identity to the nucleotide sequence represented by SEQ ID NO: 7 and has exonuclease activity; a polypeptide which is encoded by a polynucleotide consisting of the nucleotide sequence represented by SEQ ID NO: 82; and a polypeptide which is encoded by a polynucleotide consisting of a nucleotide sequence having at least 95% identity to the nucleotide sequence represented by SEQ ID NO: 82 and has exonuclease activity.

For the intracellular TALEN or exonuclease expression, a TALEN or exonuclease peptide or a polynucleotide encoding the peptide can be transferred into cells. Preferably, an expression vector containing a polynucleotide encoding each TALEN or exonuclease is transferred into cells, and the TALEN or the exonuclease is expressed in the cells. The polynucleotides of each TALEN and exonuclease may be contained in the same vector or may be contained in separate vectors. The expression vector is not particularly limited as long as the expression vector is stably retained in recipient cells and is capable of proliferating therein. Examples of the expression vector suitable for the fungus of the genus *Rhizopus* include pUC18/19, pUC118/119, pBR322, pMW218/219, pPTR1/2 (Takara Bio Inc.), pRI909/910 (Takara Bio Inc.), pDJB2 (D. J. Ballance et al., Gene, 36, 321-331, 1985), pAB4-1 (van Hartingsveldt W et al., Mol Gen Genet, 206, 71-75, 1987), pLeu4 (M. I. G. Roncero et al., Gene, 84, 335-343, 1989), pPyr225 (C.D. Skory et al., Mol Genet Genomics, 268, 397-406, 2002), and pFG1 (Gruber, F. et al., Curr Genet, 18, 447-451, 1990).

For efficient intracellular TALEN expression, it is preferred that the polynucleotide encoding the TALEN or the exonuclease should be operably linked to a promoter which functions in the fungus of the genus *Rhizopus*. Examples of the promoter which functions in the fungus of the genus *Rhizopus* include, but are not limited to, ldhA promoter (U.S. Pat. No. 6,268,189), pgk1 promoter (WO 2001/73083), pgk2 promoter (WO 2001/72967), pdcA promoter and amyA promoter (Archives of Microbiology, 2006, 186: 41-50), tef and 18S rRNA promoters (U.S. Patent Application Publication No. 2010/112651), and adh1 promoter (JP-A-2015-155759).

The polynucleotide encoding the TALEN or the exonuclease, or the expression vector containing the polynucleotide can be transferred to cells by use of a general transforming method, for example, an electroporation method, a transformation method, a transfection method, a conjugation method, a protoplast method, a particle gun method, or an *Agrobacterium* method.

The cells with the target gene deleted or inactivated by the transfer of the TALENs can be selected by the confirmation of the genomic sequences of the cells or on the basis of the pyruvate decarboxylase expression level or activity, as in the case of random mutation.

The mutant of the genus *Rhizopus* of the present invention with reduced pyruvate decarboxylase activity can be prepared by the procedures described above. The mutant of the genus *Rhizopus* of the present invention has improved productivity of an organic acid, as compared to the strain before the mutation (parent strain). Thus, the organic acid can be efficiently produced by culturing the mutant of the genus *Rhizopus* of the present invention. Thus, the present invention provides a method for producing an organic acid, comprising culturing the mutant of the genus *Rhizopus* of the present invention. Examples of the organic acid preferably include lactic acid, fumaric acid, succinic acid, malic acid and α-ketoglutaric acid, more preferably fumaric acid, succinic acid and malic acid.

The production of an organic acid using the mutant of the genus *Rhizopus* of the present invention can be performed by aerobically culturing the mutant of the genus *Rhizopus* of the present invention according to a general culture method for fungi of the genus *Rhizopus* and subsequently collecting the organic acid from the culture. For example, the mutant of the genus *Rhizopus* of the present invention can be aerobically cultured at 10° C. to 50° C., preferably 25° C. to 35° C., for several days in an appropriate medium to produce an organic acid. The number of culture days can be a period long enough for the organic acid of interest to be produced. When the organic acid of interest is, for example, lactic acid, the lactic acid is produced by culturing at the temperature mentioned above for 1 to 168 hours, preferably 2 to 72 hours, more preferably 4 to 24 hours. Alternatively, when the organic acid of interest is fumaric acid, the fumaric acid is produced by culturing at the temperature mentioned above for 1 to 168 hours, preferably 2 to 72 hours, more preferably 4 to 36 hours. The same holds true for succinic acid, malic acid, and α-ketoglutaric acid.

The medium for culturing the mutant of the genus *Rhizopus* of the present invention is not particularly limited as long as the medium permits healthy growth of the fungus of the genus *Rhizopus* and allows the organic acid of interest to be produced. Examples of the medium which can be used include: a solid or liquid media supplemented with a substrate including monosaccharides such as glucose and xylose, oligosaccharides such as sucrose, lactose, and maltose, and polysaccharides such as starch; and commercially available PDB medium (potato dextrose medium; manufactured by Becton, Dickinson and Company, etc.), PDA medium (manufactured by Becton, Dickinson and Company, etc.), LB medium (Luria-Bertani medium; manufactured by Nihon Pharmaceutical Co., Ltd. (trademark name "Daigo"), etc.), NB medium (nutrient broth; manufactured by Becton, Dickinson and Company, etc.), and SB medium (Sabouraud medium; manufactured by OXOID Limited). The medium can be appropriately further supplemented with: a biogenic substance such as glycerin or citric acid; a nitrogen source including natural nitrogen sources such as ammonium salt, nitrate, nitrite, urea, amino acids, and soybean peptide; various salts of sodium, potassium, magnesium, zinc, iron, phosphoric acid, and the like; etc.

After the culturing, the organic acid can be obtained by collecting the culture supernatant from the medium. If necessary, the organic acid in the culture solution may be collected as an organic acid salt by a method such as decantation, membrane separation, centrifugation, electrodialysis, use of ion-exchange resin, distillation, salting out, or crystallization, or a combination thereof, and then, the organic acid can be isolated or purified from the collected organic acid salt.

In one embodiment, the more efficient production of the organic acid may be performed by steps as shown below. Specifically, the organic acid can be efficiently produced by: preparing a spore suspension of the mutant of the genus *Rhizopus* of the present invention (step A); culturing the spore suspension in a culture solution so that the spores germinate to prepare mycelia (step B1); preferably further allowing the mycelia to proliferate (step B2); and subsequently culturing the prepared mycelia to produce the organic acid (step C).

<Step A: Preparation of Spore Suspension>

The spores of the mutant of the genus *Rhizopus* of the present invention are inoculated to a medium, for example, an inorganic agar medium (composition example: 2% glucose, 0.1% ammonium sulfate, 0.06% potassium dihydrogen phosphate, 0.025% magnesium sulfate heptahydrate, 0.009% zinc sulfate heptahydrate, and 1.5% agar; concentrations for all the components: % (w/v)) or PDA medium, and statically cultured at 10 to 40° C., preferably 27 to 30° C., for 7 to 10 days to form spores, which can be suspended in physiological saline or the like to prepare a spore suspension. The spore suspension may or may not contain mycelia.

<Step B1: Preparation of Mycelia>

The spore suspension obtained in the step A is inoculated to a culture solution and cultured so that the spores germinate to obtain mycelia. The number of filamentous fungal spores inoculated to the culture solution is $1 \times 10^2$ to $1 \times 10^8$ spores/mL culture solution, preferably $1 \times 10^2$ to $5 \times 10^4$ spores/mL culture solution, more preferably $5 \times 10^2$ to $1 \times 10^4$ spores/mL culture solution, further preferably $1 \times 10^3$ to $1 \times 10^4$ spores mL culture solution.

The culture solution for spore germination which is used in this step can be a commercially available medium, for example, PDB medium, LB medium, NB medium, or SB medium. Also, the culture solution can be appropriately supplemented with a carbon source including monosaccharides such as glucose and xylose, oligosaccharides such as sucrose, lactose, and maltose, and polysaccharides such as starch; a biogenic component such as glycerin or citric acid; a nitrogen source including natural nitrogen sources such as ammonium salt, nitrate, nitrite, urea, amino acids, and soybean peptide; and other inorganic materials including various salts of sodium, potassium, magnesium, zinc, iron, phosphoric acid, and the like, from the viewpoint of the rate of germination and the growth of fungal cell. The preferred concentration of a monosaccharide, an oligosaccharide, a polysaccharide or glycerin is from 0.1 to 30% (w/v). The preferred concentration of citric acid is from 0.01 to 10% (w/v). The preferred concentration of a nitrogen source is from 0.01 to 1% (w/v). The preferred concentration of an inorganic material is from 0.0001 to 0.5% (w/v).

In the step B1, the mutant of the genus *Rhizopus* of the present invention is cultured using the culture solution described above. The culturing can be performed by usual procedures. For example, the filamentous fungal spores are inoculated to a culture vessel containing the culture solution and cultured at a controlled culture temperature of 25 to 42.5° C. for preferably 24 to 120 hours, more preferably 48 to 72 hours, with stirring at preferably 80 to 250 rpm, more preferably 100 to 170 rpm. The amount of the culture solution subjected to the culture can be appropriately adjusted according to the culture vessel and can be, for example, on the order of 50 to 100 mL for a 200 mL baffled flask and on the order of 100 to 300 mL for a 500 mL baffled flask. By this culturing, the filamentous fungal spores germinate to grow into mycelia.

<Step B2: Proliferation of Mycelia>

From the viewpoint of improvement in ability to produce the organic acid, it is preferred to perform the step of further culturing the mycelia obtained in the step B1 to proliferate (step B2). The culture solution for proliferation which is used in the step B2 is not particularly limited and can be an inorganic culture solution containing glucose as usually used. Examples thereof include culture solutions containing 7.5 to 30% glucose, 0.05 to 2% ammonium sulfate, 0.03 to 0.6% potassium dihydrogen phosphate, 0.01 to 0.1% magnesium sulfate heptahydrate, 0.005 to 0.1% zinc sulfate heptahydrate, and 3.75 to 20% calcium carbonate (concentrations for all the components: % (w/v)) and preferably include culture solutions containing 10% glucose, 0.1% ammonium sulfate, 0.06% potassium dihydrogen phosphate, 0.025% magnesium sulfate heptahydrate, 0.009% zinc sulfate heptahydrate, and 5.0% calcium carbonate (concentrations for all the components: % (w/v)). The amount of the culture solution can be appropriately adjusted according to the culture vessel and can be, for example, 50 to 300 mL, preferably 100 to 200 mL, for a 500 mL Erlenmeyer flask. The fungal cells cultured in the step B1 are inoculated at 1 to 20 g fungal cells/100 mL medium, preferably 3 to 10 g fungal cells/100 mL medium, in terms of wet weight to this culture solution and cultured at a controlled culture temperature of 25 to 42.5° C. for 12 to 120 hours, preferably 16 to 72 hours, with stirring at 100 to 300 rpm, preferably 170 to 230 rpm.

<Step C: Organic Acid Production>

The filamentous fungal mycelia obtained by the procedures described above (B1 or B2) are cultured so that the fungus produces the organic acid. Then, the produced organic acid can be collected. The culture solution for organic acid production which is used in the step (C) can be a culture solution which contains a carbon source such as glucose, a nitrogen source such as ammonium salt and various metal salts, etc. and allows the organic acid to be produced. Examples of the culture solution which is used in the step (C) include culture solutions containing 7.5 to 30% glucose, 0.05 to 2% ammonium sulfate, 0.03 to 0.6% potassium dihydrogen phosphate, 0.01 to 0.1% magnesium sulfate heptahydrate, 0.005 to 0.1% zinc sulfate heptahydrate, and 3.75 to 20% calcium carbonate (concentrations for all the components: % (w/v)) and preferably include culture solutions containing 10 to 12.5% glucose, 0.1% ammonium sulfate, 0.06% potassium dihydrogen phosphate, 0.025% magnesium sulfate heptahydrate, 0.009% zinc sulfate heptahydrate, and 5.0% calcium carbonate (concentrations for all the components: % (w/v)).

The amount of the culture solution used in the step (C) can be appropriately adjusted according to the culture vessel and can be, for example, on the order of 20 to 80 mL for a 200 mL Erlenmeyer flask and on the order of 50 to 200 mL for a 500 mL Erlenmeyer flask. The fungal cells obtained in the step B1 or B2 are inoculated in an amount of 5 g to 90 g fungal cells/100 mL culture solution, preferably 5 g to 50 g fungal cells/100 mL culture solution, in terms of wet weight to this culture solution and aerobically cultured at a controlled culture temperature of 25 to 45° C. for 2 hours to 72 hours, preferably 4 hours to 36 hours, with stirring at 100 to 300 rpm, preferably 170 to 230 rpm.

The present specification further discloses the following substances, production methods, use, or methods as exemplary embodiments of the present invention. However, the present invention is not limited by these embodiments.

[1] A mutant of the genus *Rhizopus* wherein pyruvate decarboxylase activity is reduced.

[2] The mutant of the genus *Rhizopus* according to [1], wherein preferably, pdc gene is deleted or inactivated.

[3] The mutant of the genus *Rhizopus* according to [2], wherein preferably, the pdc gene is at least one polynucleotide selected from the group consisting of:

a polynucleotide consisting of the nucleotide sequence represented by SEQ ID NO: 1;

a polynucleotide consisting of a nucleotide sequence having at least 80% identity to the nucleotide sequence represented by SEQ ID NO: 1, and encoding a polypeptide which has pyruvate decarboxylase activity;

a polynucleotide consisting of a nucleotide sequence having deletion, insertion, substitution or addition of one or more nucleotides with respect to the nucleotide sequence represented by SEQ ID NO: 1, and encoding a polypeptide which has pyruvate decarboxylase activity;

a polynucleotide encoding a polypeptide which consists of the amino acid sequence represented by SEQ ID NO: 2;

a polynucleotide encoding a polypeptide which consists of an amino acid sequence having at least 80% identity to the amino acid sequence represented by SEQ ID NO: 2 and has pyruvate decarboxylase activity; and a polynucleotide encoding a polypeptide which consists of an amino acid sequence having deletion, insertion, substitution or addition of one or more amino acid residues with respect to the amino acid sequence represented by SEQ ID NO: 2 and has pyruvate decarboxylase activity.

[4] The mutant of the genus *Rhizopus* according to [2] or [3], wherein preferably, the mutant has a polynucleotide consisting of the nucleotide sequence represented by SEQ ID NO: 3, or a nucleotide sequence having at least 95% identity thereto, and a polynucleotide consisting of the nucleotide sequence represented by SEQ ID NO: 5, or a nucleotide sequence having at least 95% identity thereto transferred.

[5] The mutant of the genus *Rhizopus* according to [4], wherein preferably, the mutant further has an exonuclease or a polynucleotide encoding the exonuclease transferred.

[6] The mutant of the genus *Rhizopus* according to [5], wherein the exonuclease is preferably an exonuclease derived from a fungus of the genus *Rhizopus*, more preferably an exonuclease derived from *Rhizopus oryzae* or *Rhizopus delemar*.

[7] The mutant of the genus *Rhizopus* according to [5], wherein preferably, the polynucleotide encoding the exonuclease is a polynucleotide consisting of the nucleotide sequence represented by SEQ ID NO: 7;

a polynucleotide consisting of a nucleotide sequence having at least 95% identity to the nucleotide sequence represented by SEQ ID NO: 7, and encoding a polypeptide which has exonuclease activity;

a polynucleotide consisting of the nucleotide sequence represented by SEQ ID NO: 82;

a polynucleotide consisting of a nucleotide sequence having at least 95% identity to the nucleotide sequence represented by SEQ ID NO: 82, and encoding a polypeptide which has exonuclease activity;

a polynucleotide encoding a polypeptide which consists of the amino acid sequence represented by SEQ ID NO: 8; or a polynucleotide encoding a polypeptide which consists of an amino acid sequence having at least 95% identity to the amino acid sequence represented by SEQ ID NO: 8 and has exonuclease activity.

[8] The mutant of the genus *Rhizopus* according to any one of [1] to [7], wherein pyruvate decarboxylase activity is reduced to preferably 50% or less, more preferably 20% or less, further preferably 15% or less as compared with that before the mutation.

[9] The mutant of the genus *Rhizopus* according to any one of [1] to [8], wherein the fungus of the genus *Rhizopus* is
preferably *Rhizopus oryzae* or *Rhizopus delemar*,
more preferably *Rhizopus delemar*.

[10] The mutant of the genus *Rhizopus* according to any one of [1] to [9], wherein the mutant has improved productivity of an organic acid.

[11] A method for producing a mutant of the genus *Rhizopus*, comprising reducing pyruvate decarboxylase activity in a fungus of the genus *Rhizopus*.

[12] A method for improving productivity of an organic acid of a fungus of the genus *Rhizopus*, comprising reducing pyruvate decarboxylase activity in the fungus of the genus *Rhizopus*.

[13] The method according to [11] or [12], preferably comprising deleting or inactivating pdc gene in the fungus of the genus *Rhizopus*.

[14] The method according to [13], wherein preferably, the pdc gene is at least one polynucleotide selected from the group consisting of:

a polynucleotide consisting of the nucleotide sequence represented by SEQ ID NO: 1;

a polynucleotide consisting of a nucleotide sequence having at least 80% identity to the nucleotide sequence represented by SEQ ID NO: 1, and encoding a polypeptide which has pyruvate decarboxylase activity;

a polynucleotide consisting of a nucleotide sequence having deletion, insertion, substitution or addition of one or more nucleotides with respect to the nucleotide sequence represented by SEQ ID NO: 1, and encoding a polypeptide which has pyruvate decarboxylase activity;

a polynucleotide encoding a polypeptide which consists of the amino acid sequence represented by SEQ ID NO: 2;

a polynucleotide encoding a polypeptide which consists of an amino acid sequence having at least 80% identity to the amino acid sequence represented by SEQ ID NO: 2 and has pyruvate decarboxylase activity; and a polynucleotide encoding a polypeptide which consists of an amino acid sequence having deletion, insertion, substitution or addition of one or more amino acid residues with respect to the amino acid sequence represented by SEQ ID NO: 2 and has pyruvate decarboxylase activity.

[15] The method according to [13] or [14], wherein preferably, the deletion or inactivation of the pdc gene is performed by the genome editing of a pdc gene locus using a programmable nuclease.

[16] The method according to [15], wherein the genome editing is preferably performed using TALEN, Crispr-cas9 system, or ZFN, more preferably TALEN.

[17] The method according to [16], wherein the genome editing is
preferably transfer of TALEN peptides or polynucleotides encoding the TALEN peptides to the fungus of the genus *Rhizopus*,
more preferably transfer of polynucleotides encoding TALEN peptides to the fungus of the genus *Rhizopus*.

[18] The method according to [17], wherein preferably, the TALEN peptides consist of the following polypeptides (L) and (R):

the polypeptide (L)
having a TAL effector having 17 repeats linked, wherein
the 1st to 16th repeats counted from the upstream end among the 17 repeats each consist of an amino acid sequence having at least 85% identity to the amino acid sequence represented by SEQ ID NO: 11, or an amino acid sequence having deletion, insertion, substitution or addition of 5 or less amino acid residues with respect to the amino acid sequence represented by SEQ ID NO: 11,
the 17th repeat counted from the upstream end among the 17 repeats consists of an amino acid sequence having at least 95% identity to the amino acid sequence represented by SEQ ID NO: 27, and
the TAL effector recognizes the sequence represented by SEQ ID NO: 9, and the polypeptide (R)
having a TAL effector having 17 repeats linked, wherein
the 1st to 16th repeats counted from the upstream end among the 17 repeats each consist of an amino acid sequence having at least 85% identity to the amino acid sequence represented by SEQ ID NO: 28, or an amino acid sequence having deletion, insertion, substitution or addition of 5 or less amino acid residues with respect to the amino acid sequence represented by SEQ ID NO: 28,
the 17th repeat counted from the upstream end among the 17 repeats consists of an amino acid sequence having at least 95% identity to the amino acid sequence represented by SEQ ID NO: 44, and
the TAL effector recognizes the sequence represented by SEQ ID NO: 10.

[19] The method according to [18], wherein preferably, the 17 repeats in the TAL effector of the polypeptide (L) each have repeat-variable diresidues (RVDs) at positions corresponding to amino acid positions 12 and 13 of the amino acid sequence represented by SEQ ID NO: 11, and the respective RVDs of the repeats recognize bases at positions 2 to 18 of the sequence represented by SEQ ID NO: 9.

[20] The method according to [18], wherein preferably, the 17 repeats in the TAL effector of the polypeptide (R) each have repeat-variable diresidues (RVDs) at positions corresponding to amino acid positions 12 and 13 of the amino acid sequence represented by SEQ ID NO: 28, and the respective RVDs of the repeats recognize bases at positions 2 to 18 of the sequence represented by SEQ ID NO: 10.

[21] The method according to [18], wherein preferably, the 17 repeats in the TAL effector of the polypeptide (L) respectively consist of the following amino acid sequences (1) to (17) in order from the upstream end:

(1) the amino acid sequence represented by SEQ ID NO: 11, or an amino acid sequence having at least 95% identity thereto;
(2) the amino acid sequence represented by SEQ ID NO: 12, or an amino acid sequence having at least 95% identity thereto;
(3) the amino acid sequence represented by SEQ ID NO: 13, or an amino acid sequence having at least 95% identity thereto;
(4) the amino acid sequence represented by SEQ ID NO: 14, or an amino acid sequence having at least 95% identity thereto;
(5) the amino acid sequence represented by SEQ ID NO: 15, or an amino acid sequence having at least 95% identity thereto;
(6) the amino acid sequence represented by SEQ ID NO: 16, or an amino acid sequence having at least 95% identity thereto;
(7) the amino acid sequence represented by SEQ ID NO: 17, or an amino acid sequence having at least 95% identity thereto;
(8) the amino acid sequence represented by SEQ ID NO: 18, or an amino acid sequence having at least 95% identity thereto;
(9) the amino acid sequence represented by SEQ ID NO: 19, or an amino acid sequence having at least 95% identity thereto;
(10) the amino acid sequence represented by SEQ ID NO: 20, or an amino acid sequence having at least 95% identity thereto;
(11) the amino acid sequence represented by SEQ ID NO: 21, or an amino acid sequence having at least 95% identity thereto;
(12) the amino acid sequence represented by SEQ ID NO: 22, or an amino acid sequence having at least 95% identity thereto;
(13) the amino acid sequence represented by SEQ ID NO: 23, or an amino acid sequence having at least 95% identity thereto;
(14) the amino acid sequence represented by SEQ ID NO: 24, or an amino acid sequence having at least 95% identity thereto;
(15) the amino acid sequence represented by SEQ ID NO: 25, or an amino acid sequence having at least 95% identity thereto;
(16) the amino acid sequence represented by SEQ ID NO: 26, or an amino acid sequence having at least 95% identity thereto; and
(17) the amino acid sequence represented by SEQ ID NO: 27, or an amino acid sequence having at least 95% identity thereto.
[22] The method according to [21], wherein preferably 15 or more, more preferably 16 or more, of the sequences (1) to (17) have the following amino acid residues: amino acid residues NN at positions corresponding to amino acid positions 12 and 13 of SEQ ID NO: 11 as to the sequence (1);
amino acid residues HD at positions corresponding to amino acid positions 12 and 13 of SEQ ID NO: 12 as to the sequence (2);
amino acid residues HD at positions corresponding to amino acid positions 12 and 13 of SEQ ID NO: 13 as to the sequence (3);
amino acid residues NG at positions corresponding to amino acid positions 12 and 13 of SEQ ID NO: 14 as to the sequence (4);
amino acid residues NN at positions corresponding to amino acid positions 12 and 13 of SEQ ID NO: 15 as to the sequence (5);
amino acid residues HD at positions corresponding to amino acid positions 12 and 13 of SEQ ID NO: 16 as to the sequence (6);
amino acid residues NG at positions corresponding to amino acid positions 12 and 13 of SEQ ID NO: 17 as to the sequence (7);
amino acid residues NI at positions corresponding to amino acid positions 12 and 13 of SEQ ID NO: 18 as to the sequence (8);
amino acid residues NG at positions corresponding to amino acid positions 12 and 13 of SEQ ID NO: 19 as to the sequence (9);
amino acid residues NG at positions corresponding to amino acid positions 12 and 13 of SEQ ID NO: 20 as to the sequence (10);
amino acid residues NI at positions corresponding to amino acid positions 12 and 13 of SEQ ID NO: 21 as to the sequence (11);
amino acid residues NI at positions corresponding to amino acid positions 12 and 13 of SEQ ID NO: 22 as to the sequence (12);
amino acid residues NI at positions corresponding to amino acid positions 12 and 13 of SEQ ID NO: 23 as to the sequence (13);
amino acid residues NI at positions corresponding to amino acid positions 12 and 13 of SEQ ID NO: 24 as to the sequence (14);
amino acid residues NG at positions corresponding to amino acid positions 12 and 13 of SEQ ID NO: 25 as to the sequence (15);
amino acid residues HD at positions corresponding to amino acid positions 12 and 13 of SEQ ID NO: 26 as to the sequence (16); and
amino acid residues NN at positions corresponding to amino acid positions 12 and 13 of SEQ ID NO: 27 as to the sequence (17).
[23] The method according to [18], wherein preferably, the 17 repeats in the TAL effector of the polypeptide (R) respectively consist of the following amino acid sequences (1') to (17') in order from the upstream end:
(1') the amino acid sequence represented by SEQ ID NO: 28, or an amino acid sequence having at least 95% identity thereto;
(2') the amino acid sequence represented by SEQ ID NO: 29, or an amino acid sequence having at least 95% identity thereto;
(3') the amino acid sequence represented by SEQ ID NO: 30, or an amino acid sequence having at least 95% identity thereto;
(4') the amino acid sequence represented by SEQ ID NO: 31, or an amino acid sequence having at least 95% identity thereto;
(5') the amino acid sequence represented by SEQ ID NO: 32, or an amino acid sequence having at least 95% identity thereto;
(6') the amino acid sequence represented by SEQ ID NO: 33, or an amino acid sequence having at least 95% identity thereto;
(7') the amino acid sequence represented by SEQ ID NO: 34, or an amino acid sequence having at least 95% identity thereto;
(8') the amino acid sequence represented by SEQ ID NO: 35, or an amino acid sequence having at least 95% identity thereto;

(9') the amino acid sequence represented by SEQ ID NO: 36, or an amino acid sequence having at least 95% identity thereto;
(10') the amino acid sequence represented by SEQ ID NO: 37, or an amino acid sequence having at least 95% identity thereto;
(11') the amino acid sequence represented by SEQ ID NO: 38, or an amino acid sequence having at least 95% identity thereto;
(12') the amino acid sequence represented by SEQ ID NO: 39, or an amino acid sequence having at least 95% identity thereto;
(13') the amino acid sequence represented by SEQ ID NO: 40, or an amino acid sequence having at least 95% identity thereto;
(14') the amino acid sequence represented by SEQ ID NO: 41, or an amino acid sequence having at least 95% identity thereto;
(15') the amino acid sequence represented by SEQ ID NO: 42, or an amino acid sequence having at least 95% identity thereto;
(16') the amino acid sequence represented by SEQ ID NO: 43, or an amino acid sequence having at least 95% identity thereto; and
(17') the amino acid sequence represented by SEQ ID NO: 44, or an amino acid sequence having at least 95% identity thereto.
[24] The method according to [23], wherein preferably 15 or more, more preferably 16 or more, of the sequences (1') to (17') have the following amino acid residues: amino acid residues NG at positions corresponding to amino acid positions 12 and 13 of SEQ ID NO: 28 as to the sequence (1');
amino acid residues NN at positions corresponding to amino acid positions 12 and 13 of SEQ ID NO: 29 as to the sequence (2');
amino acid residues NI at positions corresponding to amino acid positions 12 and 13 of SEQ ID NO: 30 as to the sequence (3');
amino acid residues NG at positions corresponding to amino acid positions 12 and 13 of SEQ ID NO: 31 as to the sequence (4');
amino acid residues NG at positions corresponding to amino acid positions 12 and 13 of SEQ ID NO: 32 as to the sequence (5');
amino acid residues NG at positions corresponding to amino acid positions 12 and 13 of SEQ ID NO: 33 as to the sequence (6');
amino acid residues HD at positions corresponding to amino acid positions 12 and 13 of SEQ ID NO: 34 as to the sequence (7');
amino acid residues HD at positions corresponding to amino acid positions 12 and 13 of SEQ ID NO: 35 as to the sequence (8');
amino acid residues NG at positions corresponding to amino acid positions 12 and 13 of SEQ ID NO: 36 as to the sequence (9');
amino acid residues NG at positions corresponding to amino acid positions 12 and 13 of SEQ ID NO: 37 as to the sequence (10');
amino acid residues NI at positions corresponding to amino acid positions 12 and 13 of SEQ ID NO: 38 as to the sequence (11');
amino acid residues NI at positions corresponding to amino acid positions 12 and 13 of SEQ ID NO: 39 as to the sequence (12');
amino acid residues NN at positions corresponding to amino acid positions 12 and 13 of SEQ ID NO: 40 as to the sequence (13');
amino acid residues NI at positions corresponding to amino acid positions 12 and 13 of SEQ ID NO: 41 as to the sequence (14');
amino acid residues HD at positions corresponding to amino acid positions 12 and 13 of SEQ ID NO: 42 as to the sequence (15');
amino acid residues NN at positions corresponding to amino acid positions 12 and 13 of SEQ ID NO: 43 as to the sequence (16'); and
amino acid residues NN at positions corresponding to amino acid positions 12 and 13 of SEQ ID NO: 44 as to the sequence (17').
[25] The method according to any one of [18] to [24], wherein preferably, the polypeptide (L) is the following polypeptide:
a polypeptide which consists of the amino acid sequence represented by SEQ ID NO: 4;
a polypeptide which consists of an amino acid sequence having at least 95% identity to the amino acid sequence represented by SEQ ID NO: 4 and has a TAL effector targeting the sequence represented by SEQ ID NO: 9 and a DNA cleavage domain consisting of Fok1-like DNA nuclease;
a polypeptide which is encoded by a polynucleotide consisting of the nucleotide sequence represented by SEQ ID NO: 3; or
a polypeptide which is encoded by a polynucleotide consisting of a nucleotide sequence having at least 95% identity to the nucleotide sequence represented by SEQ ID NO: 3 and has a TAL effector targeting the sequence represented by SEQ ID NO: 9 and a DNA cleavage domain consisting of Fok1-like DNA nuclease.
[26] The method according to any one of [18] to [25], wherein preferably, the polypeptide (R) is the following polypeptide:
a polypeptide which consists of the amino acid sequence represented by SEQ ID NO: 6;
a polypeptide which consists of an amino acid sequence having at least 95% identity to the amino acid sequence represented by SEQ ID NO: 6 and has a TAL effector targeting the sequence represented by SEQ ID NO: 10 and a DNA cleavage domain consisting of Fok1-like DNA nuclease;
a polypeptide which is encoded by a polynucleotide consisting of the nucleotide sequence represented by SEQ ID NO: 5; or
a polypeptide which is encoded by a polynucleotide consisting of a nucleotide sequence having at least 95% identity to the nucleotide sequence represented by SEQ ID NO: 5 and has a TAL effector targeting the sequence represented by SEQ ID NO: 10 and a DNA cleavage domain consisting of Fok1-like DNA nuclease.
[27] The method according to [17], wherein preferably, the polynucleotides encoding the TALENs are the following polynucleotides i) and ii):
i) a polynucleotide consisting of the nucleotide sequence represented by SEQ ID NO: 3, or a nucleotide sequence having at least 95% identity thereto, or
a polynucleotide encoding a polypeptide which consists of the amino acid sequence represented by SEQ ID NO: 4, or an amino acid sequence having at least 95% identity thereto, and ii) a polynucleotide consisting of the nucleotide sequence represented by SEQ ID NO: 5, or a nucleotide sequence having at least 95% identity thereto, or
a polynucleotide encoding a polypeptide which consists of the amino acid sequence represented by SEQ ID NO: 6, or an amino acid sequence having at least 95% identity thereto.
[28] The method according to any one of [17] to [27], preferably further comprising transferring an exonuclease or a polynucleotide encoding the exonuclease to the fungus of the genus *Rhizopus*.
[29] The method according to [28], wherein the exonuclease is
preferably an exonuclease derived from a fungus of the genus *Rhizopus*,
more preferably an exonuclease derived from *Rhizopus oryzae* or *Rhizopus delemar*.
[30] The method according to [28], wherein preferably, the polynucleotide encoding the exonuclease is
a polynucleotide consisting of the nucleotide sequence represented by SEQ ID NO: 7;
a polynucleotide consisting of a nucleotide sequence having at least 95% identity to the nucleotide sequence represented by SEQ ID NO: 7, and encoding a polypeptide which has exonuclease activity;
a polynucleotide consisting of the nucleotide sequence represented by SEQ ID NO: 82;
a polynucleotide consisting of a nucleotide sequence having at least 95% identity to the nucleotide sequence represented by SEQ ID NO: 82, and encoding a polypeptide which has exonuclease activity;
a polynucleotide encoding a polypeptide which consists of the amino acid sequence represented by SEQ ID NO: 8; or
a polynucleotide encoding a polypeptide which consists of an amino acid sequence having at least 95% identity to the amino acid sequence represented by SEQ ID NO: 8 and has exonuclease activity.

[31] The method according to any one of [11] to [30], wherein the fungus of the genus *Rhizopus* is
preferably *Rhizopus oryzae* or *Rhizopus delemar*,
more preferably *Rhizopus delemar*.
[32] The method according to any one of [11] to [31], wherein the reduction of pyruvate decarboxylase activity in the fungus of the genus *Rhizopus* is reduction to preferably 50% or less, more preferably 20% or less, further preferably 15% or less.
[33] A method for producing an organic acid, comprising culturing the mutant of the genus *Rhizopus* according to any one of [1] to [10].
[34] The method for producing an organic acid according to [33], preferably further comprising collecting the organic acid from the culture after the culturing.
[35] The method for producing an organic acid according to [33] or [34], wherein the organic acid is
preferably fumaric acid, lactic acid, succinic acid, malic acid or α-ketoglutaric acid,
more preferably fumaric acid, succinic acid or malic acid.
[36] Use of the mutant of the genus *Rhizopus* according to any one of [1] to [10] for production of an organic acid.
[37] The use according to [36], wherein the organic acid is
preferably fumaric acid, lactic acid, succinic acid, malic acid or α-ketoglutaric acid,
more preferably fumaric acid, succinic acid or malic acid.

EXAMPLES

Hereinafter, the present invention will be described in more detail with reference to Examples. However, the present invention is not limited by these examples.

The PCR primers used in the present Examples are shown in Tables 1 and 2.

TABLE 1

| Primer | Sequence (5'→3') | SEQ ID NO |
|---|---|---|
| oJK162 | cgagctcgaattatttaaatgaacagcaagttaataatctagaggg | 45 |
| oJK163 | tatgaccatgattacgatgagaggcaaaatgaagcgtac | 46 |
| oJK164 | atttaaataattcgagctcggtacccgggg | 47 |
| oJK165 | cgtaatcatggtcatagctg | 48 |
| oJK202 | tagagggaaaagagagaattgaaatagg | 49 |
| oJK204 | ttttgttatttaattgtattaattgataatg | 50 |
| oJK205 | aattaaataacaaaatcattttaattacgcattttc | 51 |
| oJK216 | catgattacgcggccgcgccattataatgcactagtg | 52 |
| oJK210 | ctcttttccctctaatgagaggcaaaatgaagcgtac | 53 |
| oJK211 | atttaaatgtaatcatggtcatagctgtttc | 54 |
| trpC-lost-F | tttaaattagagggaaaagagagaattgaaatag | 55 |
| trpC-lost-R | tccctctaatttaaatgaattcgagctcggtaccc | 56 |
| adhpro-R | ttttgttatttaattgtattaattgataatg | 57 |
| adhter-F | tcattttaattacgcattttcatttac | 58 |
| adhpro-TALEN-F | aattaaataacaaaatggactacaaagaccatgacggtg | 59 |
| TAELN-adhter-R | gcgtaattaaaatgattaaaagtttatctcgccgttatta | 60 |

TABLE 1-continued

| Primer | Sequence (5'→3') | SEQ ID NO |
|---|---|---|
| pPTR1-sal1-F | gggtaccgagctcgaattc | 61 |
| pPTR1-sal1-R | ggggatcctctagagtcgac | 62 |
| sal1-Idhpro-F3 | ctctagaggatcccctaggtgtggctgtggtgaccatattg | 63 |
| Idhpro-R | gagaattatattgtaaagaaaaataaag | 64 |
| Idhpro-exo1-F2 | tacaatataattctcatgaaaatccaagttgcttctcctattgaccaatc | 65 |
| exo1-pdcter-R2 | atgaattctaagatttatcttctttcatgagaaacactaaacttgataac | 66 |
| pdcTer-F | aatcttagaattcatctttttttg | 67 |
| pdcTer-sal1-R | tcgagctcggtacccactctaccgtctgctcttttgtct | 68 |
| pUC18-Pae1-F3 | ctgcaggtcgactctagaggatcccccgggtaccg | 69 |
| pUC18-Hind3-R3 | gcttggcactggccgtcgttttacaacgtcgtgac | 70 |
| PDC1-upstr-F | cggccagtgccaagcgcagacttcaacagttggcttttttaagta | 71 |
| PDC1-upstr-R | cattttgcctctcatgttttaaatttgttttgtagagtattgaata | 72 |
| trpCpro-R | gaacagcaagttaataatctagagggcgc | 73 |
| trpCter-F | atgagaggcaaaatgaagcgtacaaagag | 74 |
| PDC1-downstr-F | attaacttgctgttcaatcttagaattcattttttttttgtatcattcg | 75 |
| PDC1-downstr-R | agagtcgacctgcaggcgtcaataagagcttgaaggttggtgccggatc | 76 |
| PDC1-upstr-F2 | gcagacttcaacagttggcttttttaagta | 77 |
| PDC1-downstr-R-P | (p)-gcgtcaataagagcttgaaggttggtgccggatc | 78 |
| pdc1-up2 | cattcccacaggatttgtgc | 79 |
| trpC(d)-1 | gtgagatgttgatcatttgtacatg | 80 |

(p): 5'-terminally phosphorylated

TABLE 2

| Primer | Sequence (5'→3') | SEQ ID NO |
|---|---|---|
| trpCter-R | atgagaggcaaaatgaagcgtacaaagag | 88 |
| trpCter-cicCpro-F | cattttgcctctcatcttacgcaggttgatagtagccgcc | 89 |
| cipCpro-adhter-R | gcgtaattaaaatgaggttagagtatgaagaaaaaaaaaa | 90 |
| trpC-lost-F2 | tttaaatcttacgcaggttgatagtagccgc | 91 |
| trpC-lost-R2 | tgcgtaagatttaaatgaattcgagctcggtac | 92 |
| cipCpro-R | ggttagagtatgaagaaaaaaaaaaacg | 93 |
| cipCpro-LifeTALEN-F | cttcatactctaaccatgggaaaacctattcctaatcctctgctg | 94 |
| LifeTALEN-adhter-R | gcgtaattaaaatgatcagaagttgatctcgccgttgttgaactttc | 95 |
| cipCpro-exo1-F | cttcatactctaaccatgaaaatccaagttgcttctccta | 96 |
| exo1-adhter-R | gcgtaattaaaatgattatcttctttcatgagaaacacta | 97 |
| pdc3-upstr-F | cggccagtgccaagcccgtcagggtgaatgagatatttt | 98 |
| pdc3-upstr-R2 | aaaagatgtgagttataaaaggatgatgcaagc | 99 |
| pdc3-downstr-F2 | taactcacatcttttattcttttctatccctc | 100 |
| pdc3-downstr-R | agagtcgacctgcaggacctgttagaaaggtacatgcattc | 101 |

TABLE 2-continued

| Primer | Sequence (5'→3') | SEQ ID NO |
|---|---|---|
| pdc3-upstr-R | cattttgcctctcatgtgagttataaaaggatgatgcaag | 102 |
| pdc3-downstr-F | attaacttgctgttcatcttttattcttttctatccctc | 103 |
| pdc3-upstr-F2 | ccgtcaggggtgaatgagatatt | 104 |
| pdc3-downstr-R2-P | (p)-acctgttagaaaggtacatgcattc | 105 |
| pdc-up | gacctcaatcactatccttgg | 106 |

(p): 5'-terminally phosphorylated

Example 1 Preparation of PDC Gene-Deficient Mutant of Genus *Rhizopus*

(1) Preparation of Tryptophan Auxotrophic Strain

A tryptophan auxotrophic strain derived from a *Rhizopus delemar* JCM (Japan Collection of Microorganisms/Riken, Japan) 5557 strain (hereinafter, referred to as a 5557 strain) was used as a parent strain for pdc gene (SEQ ID NO: 1) deletion. The tryptophan auxotrophic strain was obtained by screening from among strains mutated by ion beam irradiation of the 5557 strain. The ion beam irradiation was performed at the facility of Takasaki ion accelerators for advanced radiation application (TIARA), Takasaki Advanced Radiation Research Institute, National Institutes for Quantum and Radiological Science and Technology. The strain was irradiated with 100 to 1,250 G ray at an energy of 220 MeV with $^{12}C^{5+}$ accelerated using an AVF cyclotron. Spores were collected from the irradiated fungal cells. From among them, a *Rhizopus delemar* 02T6 strain which had a one-base deletion mutation in the trpC gene region and exhibited tryptophan auxotrophy was obtained. This strain was used as a parent strain of the mutant of the genus *Rhizopus* in subsequent Examples.

(2) Plasmid Vector Preparation

A DNA fragment of the trpC gene was synthesized by PCR using the genomic DNA of the 5557 strain as a template and primers oJK162 (SEQ ID NO: 45) and oJK163 (SEQ ID NO: 46). Next, a DNA fragment was amplified by PCR using a plasmid pUC18 as a template with primers of oJK164 (SEQ ID NO: 47) and oJK165 (SEQ ID NO: 48). These two fragments were ligated using In-Fusion HD Cloning Kit (Clontech Laboratories, Inc.) to prepare a plasmid pUC18-trpC.

Subsequently, a promoter fragment and a terminator fragment of adh1 were amplified by PCR using the genomic DNA of the 5557 strain as a template with primers of oJK202 (SEQ ID NO: 49) and oJK204 (SEQ ID NO: 50) and primers oJK205 (SEQ ID NO: 51) and oJK216 (SEQ ID NO: 52), respectively. Next, a DNA fragment was amplified by PCR using the plasmid pUC18-trpC constructed as described above as a template with primers of oJK210 (SEQ ID NO: 53) and oJK211 (SEQ ID NO: 54). These three fragments were ligated using In-Fusion HD Cloning Kit (Clontech Laboratories, Inc.) to prepare a plasmid pUC18-trpC-Padh-Tadh. In the obtained plasmid, the adh1 promoter and terminator were placed in order downstream of the trpC gene region.

Further, a plasmid vector in which the trpC gene region from pUC18-trpC-Padh-Tadh was prepared. Specifically, a DNA fragment was amplified by PCR using the pUC18-trpC-Padh-Tadh constructed as described above as a template with primers of trpC-lost-F (SEQ ID NO: 55) and trpC-lost-R (SEQ ID NO: 56). This fragment was ligated using In-Fusion HD Cloning Kit (Clontech Laboratories, Inc.) to prepare a plasmid pUC18-Padh-Tadh.

(3) Preparation of TALEN for PDC Gene Disruption

Custom XTN TALEN (trade name of TALEN provided by Transposagen Biopharmaceuticals, Inc.) was prepared by Transposagen Biopharmaceuticals, Inc. on a request. This is a kit for TALENs targeting a gene encoding pyruvate decarboxylase 1 (PDC1) (pdc gene; SEQ ID NO: 1) and contains two polynucleotides LeftTALEN-pdc (SEQ ID NO: 3) and RightTALEN-pdc (SEQ ID NO: 5) which bind to a region containing the pdc gene (SEQ ID NO: 81). LeftTALEN-pdc encodes TALEN targeting the sequence of 5'-TGCCTGCTATTAAAATCG-3' (SEQ ID NO: 9) in the sense strand of the pdc gene, and RightTALEN-pdc encodes TALEN targeting the sequence of 5'-TTGATTTCCTTAA-GACGG-3' (SEQ ID NO: 10) in the antisense strand thereof.

The polynucleotide encoding LeftTALEN-pdc was inserted to the expression vector pUC18-trpC-Padh-Tadh for *R. delemar* prepared in the paragraph (2) to prepare a vector for expression of TALEN under control of the adh1 promoter and the adh1 terminator. Specifically, a vector fragment was amplified by PCR using pUC18-trpC-Padh-Tadh as a template with primers of adhpro-R (SEQ ID NO: 57) and adhter-F (SEQ ID NO: 58). Subsequently, a Left-TALEN-pdc fragment was amplified by PCR using Left-TALEN-pdc as a template with primers of adhpro-TALEN-F (SEQ ID NO: 59) and TALEN-adhter-R (SEQ ID NO: 60). These two fragments contained regions overlapping with each other by 15 bases. These two fragments were ligated using In-Fusion HD cloning kit (Clontech Laboratories, Inc.) to obtain a plasmid padh-LeftTALEN-pdc containing LeftTALEN-pdc.

The polynucleotide encoding RightTALEN-pdc was inserted to the expression vector pUC18-Padh-Tadh for *R. delemar* prepared in the paragraph (2) to prepare a vector for expression of TALEN (without the trpC sequence) under control of the adh1 promoter and the adh1 terminator. Specifically, a vector fragment was amplified by PCR using pUC18-Padh-Tadh as a template with primers of adhpro-R (SEQ ID NO: 57) and adhter-F (SEQ ID NO: 58). Subsequently, a RightTALEN-pdc fragment was amplified by PCR using RightTALEN-pdc as a template with primers of adhpro-TALEN-F (SEQ ID NO: 59) and TALEN-adhter-R (SEQ ID NO: 60), and ligated with the vector fragment to obtain a plasmid padh-RightTALEN-pdc containing RightTALEN-pdc.

(4) Preparation of Exonuclease Expression Vector

A pUC18 vector fragment was amplified by PCR using a plasmid pUC18 (Takara Bio Inc.) as a template with primers of pPTR1-call-F (SEQ ID NO: 61) and pPTR1-sal1-R (SEQ ID NO: 62). Also, a ldh promoter fragment was amplified using a purified genome solution of a *Rhizopus oryzae* NRBC5384 strain (hereinafter, referred to as a 5384 strain) as a template with primers of sal1-ldhpro-F3 (SEQ ID NO: 63) and ldhpro-R (SEQ ID NO: 64). An exonuclease gene fragment (SEQ ID NO: 82) was amplified using the same template as above with primers of ldhpro-exo1-F2 (SEQ ID NO: 65) and exo1-pdcter-R2 (SEQ ID NO: 66). A pdc terminator fragment was amplified using the same template as above with primers of pdcTer-F (SEQ ID NO: 67) and pdcTer-sal1-R (SEQ ID NO: 68). These four amplified fragments were ligated using In-Fusion HD cloning kit (Clontech Laboratories, Inc.) to prepare a plasmid pldh-exo1.

(5) Preparation of Plasmid for trpC Knock-in

A plasmid ptrpC-knock-in for removing pdc gene ORF and knocking-in the trpC gene region at the pdc gene locus was prepared. Specifically, a pUC18 vector fragment amplified using pUC18 as a template with primers of pUC18-Pae1-F3 (SEQ ID NO: 69) and pUC18-Hindi-R3 (SEQ ID NO: 70), a promoter site fragment of the pdc gene amplified using the genome of the JCM5557 strain as a template with primers of PDC1-upstr-F (SEQ ID NO: 71) and PDC1-upstr-R (SEQ ID NO: 72), a trpC gene region fragment amplified using the genome of the JCM5557 strain as a template with primers of trpCpro-R (SEQ ID NO: 73) and trpCter-F (SEQ ID NO: 74), and a terminator site fragment of the pdc gene amplified using the genome of the JCM5557 strain as a template with primers of PDC1-downstr-F (SEQ ID NO: 75) and PDC1-downstr-R (SEQ ID NO: 76) were ligated using In-Fusion HD Cloning Kit (Clontech Laboratories, Inc.) to construct a plasmid ptrpC-knock-in.

(6) Preparation of Single-Stranded DNA

A DNA fragment was amplified by PCR using the plasmid ptrpC-knock-in as a template with primers of PDC1-upstr-F2 (SEQ ID NO: 77) and PDC1-downstr-R-P (SEQ ID NO: 78; 5'-terminally phosphorylated primer). The template was degraded by Dpn1 (Toyobo Co., Ltd.) treatment. Then, the product was purified by phenol/chloroform/isoamyl alcohol treatment and ethanol precipitation treatment. The purified product was further treated using Lambda Exonuclease (NEW ENGLAND BioLabs Inc.) and then purified in the same way as above to obtain single-stranded DNA. The Lambda Exonuclease treatment was performed overnight at 37° C.

(7) Gene Transfer Using Particle Gun

The plasmids padh-LeftTALEN-pdc and padh-RightTALEN-pdc prepared in the paragraph (3) were treated with a restriction enzyme ScaI, and the plasmid pldh-exo1 prepared in the paragraph (4) was treated with a restriction enzyme Pst1. padh-LeftTALEN-pdc, padh-RightTALEN-pdc, pldh-exo1 and the single-stranded DNA prepared in the paragraph (6) were mixed at a concentration ratio of 2:4:2:1 to prepare a DNA solution (approximately 1 to 3 µg/µL). 10 µL of the DNA solution was added to and mixed with 100 µL of a gold particle solution (60 mg/mL, INBIO GOLD, particle size: 1 µm). Further, 40 µL of 0.1 M spermidine was added thereto, and the mixture was well stirred by vortex. 100 µL of 2.5 M CaCl$_2$ was added thereto, and the mixture was stirred for 1 minute by vortex and then centrifuged at 6,000 rpm for 30 seconds to remove a supernatant. To the obtained precipitates, 200 µL of 70% EtOH was added, and the mixture was stirred for 30 seconds by vortex and then centrifuged at 6,000 rpm for 30 seconds to remove a supernatant. The obtained precipitates were resuspended in 100 µL of 100% EtOH.

The spores of the 02T6 strain obtained in the paragraph (1) were subjected to gene transfer using the DNA-gold particle solution described above and GDS-80 (Nepa Gene Co Ltd.). The spores after the gene transfer were statically cultured at 30° C. for approximately 1 week on an inorganic agar medium (20 g/L glucose, 1 g/L ammonium sulfate, 0.6 g/L potassium dihydrogen phosphate, 0.25 g/L magnesium sulfate heptahydrate, 0.09 g/L zinc sulfate heptahydrate, and 15 g/L agar).

(8) Selection of PDC Gene-Deficient Strain

The spores were collected from the fungal cells cultured in the paragraph (7). Fungal strains were isolated using an inorganic agar medium (20 g/L glucose, 1 g/L ammonium sulfate, 0.6 g/L potassium dihydrogen phosphate, 0.25 g/L magnesium sulfate heptahydrate, 0.09 g/L zinc sulfate heptahydrate, and 15 g/L agar) adjusted to pH 3. A portion of mycelia of the grown fungal strains was scraped off using a toothpick, then suspended in 10 mM Tris-HCl (pH 8.5), and incubated at 95° C. for 10 minutes. Then, the suspension was appropriately diluted with 10 mM Tris-HCl (pH 8.5) to prepare a genome template solution for colony PCR. Colony PCR was performed using the genome template solution, primers pdc1-up2 (SEQ ID NO: 79) and trpC(d)-1 (SEQ ID NO: 80), and KOD FX Neo (Toyobo Co., Ltd.). The colony PCR using these primers amplifies a DNA fragment having an appropriate length if the trpC gene fragment is knocked-in at the pdc gene locus. By the colony PCR, a fungal strain with the DNA amplification fragment obtained was obtained as a pdc gene-deficient strain 02T6Δpdc.

Example 2 Evaluation of Pyruvate Decarboxylase Activity in Mutant of Genus *Rhizopus*

The 02T6 strain and 02T6Δpdc strain obtained in Example 1 were cultured, and their pyruvate decarboxylase (PDC) activities were measured.

(1) Culturing of Fungal Cells 200 mL of a seed medium (composition: SD/-Trp Broth (Clontech Laboratories, Inc.; prepared according to the attached protocol), 0.002% tryptophan, and 0.5% sorbitan monolaurate (Rheodol® SP-L10, manufactured by Kao Corp.); concentrations for all the components: % (w/v)) was applied to a 500 mL baffled flask (manufactured by Asahi Glass Co., Ltd.). The spore suspension of the 02T6 strain or the 02T6Δpdc strain was inoculated thereto at 1×10$^3$ spores/mL medium and cultured with stirring at 170 rpm at 27° C. for approximately 72 hours. Subsequently, the obtained cultures were filtered through a sterilized wire mesh having a mesh size of 250 µm to collect fungal cells on the filter. 6.0 to 8.0 g of the collected fungal cells was inoculated to 100 mL of an inorganic culture solution (composition: 10% glucose, 0.1% ammonium sulfate, 0.06% potassium dihydrogen phosphate, 0.025% magnesium sulfate heptahydrate, 0.009% zinc sulfate heptahydrate, 5.0% calcium carbonate, and 0.002% tryptophan; concentrations for all the components: % (w/v)) applied to a 500 mL Erlenmeyer flask, and cultured with stirring at 220 rpm at 27° C. for approximately 40 hours. The obtained cultures were filtered through a sterilized stainless screen filter holder (manufactured by Merck Millipore) to collect fungal cells on the filter. The fungal cells were washed twice with approximately 50 mL of physiological saline on this filter holder. The physiological saline used in the washing was removed by suction filtration. 6 g of the obtained fungal cells was inoculated to 40 mL of an inorganic culture solution (composition: 10% glucose, 0.1% ammonium sulfate, 0.06% potassium dihydrogen phosphate, 0.025% magnesium sulfate heptahydrate, 0.009% zinc sulfate heptahydrate, 5.0% calcium carbonate, and 0.002% tryptophan; concentrations for all the components: % (w/v)) applied to a 200 mL Erlenmeyer flask, and shake-cultured at 35° C. at 170 rpm for 8 hours.

(2) Evaluation of Pyruvate Decarboxylase (PDC) Activity

The cultures obtained in the paragraph (1) were filtered through a sterilized stainless screen filter holder (manufactured by Merck Millipore) to collect fungal cells on the filter. The fungal cells were further washed twice with approximately 50 mL of physiological saline on this filter holder. The physiological saline used in the washing was removed by suction filtration. 0.3 g of the fungal cells was collected into a 3 mL tube for homogenizing (manufactured by Yasui Kikai Corp.), and a metal cone for 3 mL (manufactured by Yasui Kikai Corp.) was placed therein. After closing of the lid, the tube was frozen with liquid nitrogen. The frozen 3 mL tube for homogenizing was applied to Multi-Beads Shocker (manufactured by Yasui Kikai Corp.), and the fungal cells were homogenized at 1,700 rpm for 10 seconds. Then, the homogenate was suspended in a 50 mM Tri-HCl (pH 7.5) solution supplemented with complete ULTRA Tablets, Mini, EDTA-free, EASY pack (F. Hoffmann-La Roche, Ltd.) and then centrifuged at 14,500 rpm for 5 minutes to obtain a supernatant as a homogenate of fungal cells. The protein concentration of the homogenate of fungal cells was measured using Quick Start Bradford Protein Assay (Bio-Rad Laboratories, Inc.).

The PDC activity of the homogenate of fungal cells was quantified by monitoring the amount of $NAD^+$ formed on the basis of change in absorbance, with the NAD being caused by reaction of alcohol dehydrogenase (hereinafter, referred to as ADH) with a reaction product of pyruvate and the homogenate of fungal cells. Specifically, 10 L of the homogenate of fungal cells appropriately diluted was added to 180 µL of a reaction solution [50 mM Tris-HCl (pH 7.5), 175 µM NADH, 2 mM $MgCl_2$, 1 mM thiamine diphosphate, and 1 U ADH (Sigma-Aldrich Co. LLC)], and the mixture was incubating at 35° C. for 5 minutes. Then, 10 µL of a 200 mM sodium pyruvate solution was added to the reaction solution, and the reaction was started at 35° C. Change in absorbance was measured using infinite M200 PRO (Tecan Trading AG). 1 U was defined as the amount of the enzyme forming 1 µmol of $NAD^+$ at 35° C. for 1 minute.

The results are shown in Table 3. The PDC activity in the 02T6Δpdc strain was decreased to approximately 13% as compared with the 02T6 strain as a parent strain.

TABLE 3

|  | O2T6 strain | 02T6Δpdc strain |
| --- | --- | --- |
| PDC activity (U/g-protein) | 2378 | 307 |

Example 3 Evaluation of Organic Acid Productivity in Mutant of Genus Rhizopus

The 02T6 strain and the 02T6Δpdc strain were cultured by the same procedures as in Example 2(1) except that the culture period was set to 2 days. At 0, 4, 8, 10, 24 and 32 hours after the start of culturing, the supernatants of the culture solutions were sampled. Glucose, fumaric acid, malic acid, succinic acid and ethanol in the supernatants were quantified by the procedures described in Reference Example 1 mentioned later. Subsequently, the selectivity of each substance was determined.

Table 4 shows the selectivity of each substance at the time point when the complete consumption of glucose was confirmed (at 24 hours after the start of culturing). The selectivity of ethanol in the 02T6Δpdc strain was decreased to 95.5% as compared with the 02T6 strain as a parent strain, whereas the selectivity s of fumaric acid, malic acid and succinic acid were improved to 117%, 112% and 108%, respectively, demonstrating that the organic acid productivity was improved.

TABLE 4

| | Selectivity | | |
| --- | --- | --- | --- |
|  | 02T6 strain (%) | 02T6Δpdc strain (%) | 02T6Δpdc strain/ 02T6 strain |
| Ethanol | 58.8 | 56.1 | 0.955 |
| Fumaric acid | 21.5 | 25.3 | 1.17 |
| Malic acid | 1.72 | 1.93 | 1.12 |
| Succinic acid | 1.47 | 1.59 | 1.08 |

Comparative Example 1 Evaluation of Pyruvate Decarboxylase Activity of Pdc3 Gene-Disrupted Strain (1) Preparation of Plasmid Vector A plasmid vector was prepared by changing the adh1 promoter of the pUC18-trpC-Padh-Tadh constructed in Example 1(2) to cipC promoter. Specifically, a vector fragment was amplified by PCR using the pUC18-trpC-Padh-Tadh as a template with primers of adhter-F (SEQ ID NO: 58) and trpCter-R (SEQ ID NO: 88). Also, a cipC promoter region fragment was amplified by PCR using the genomic DNA of the 5557 strain as a template with primers of trpCter-cicCpro-F (SEQ ID NO: 89) and cipCpro-adhter-R (SEQ ID NO: 90). These two fragments were ligated using In-Fusion HD Cloning Kit (Clontech Laboratories, Inc.) to prepare a plasmid pUC18-trpC-PcipC-Tadh.

Subsequently, a plasmid vector in which the trpC gene region was removed from the pUC18-trpC-PcipC-Tadh constructed as described above was prepared. Specifically, a DNA fragment was amplified by PCR using the pUC18-trpC-PcipC-Tadh as a template with primers of trpC-lost-F2 (SEQ ID NO: 91) and trpC-lost-R2 (SEQ ID NO: 92). This fragment was ligated using In-Fusion HD Cloning Kit (Clontech Laboratories, Inc.) to prepare a plasmid pUC18-PcipC-Tadh.

(2) Preparation of TALEN for Pdc3 Gene Disruption

TALENs targeting the pdc3 gene locus were prepared. The TALEN preparation was requested to Life Technologies Corp. to obtain GeneArt PerfectMatch TALs (trade name of TALEN provided by Life Technologies Corp.). This kit contains two polynucleotides encoding Left-TALEN and Right-TALEN for the target gene. The kit targeting the pdc3 gene (SEQ ID NO: 83) contains LeftTALEN-pdc3 (SEQ ID NO: 84) and RightTALEN-pdc3 (SEQ ID NO: 85) which encode TALENs targeting the sequence of 5'-CCG-GAATCGACACGATTTT-3' (SEQ ID NO: 86) in the sense strand of the pdc3 gene and the sequence of 5'-CGTAACT-TACCATATTGTA-3' (SEQ ID NO: 87) in the antisense strand thereof, respectively.

The polynucleotide encoding Left-TALEN for the pdc3 gene was inserted to the expression vector pUC18-PcipC-Tadh for R. delemar prepared in the paragraph (1) to prepare a vector for expression of TALEN under control of the cipC promoter and the adh1 terminator. Specifically, a vector fragment was amplified by PCR using pUC18-PcipC-Tadh as a template with primers of cipCpro-R (SEQ ID NO: 93) and adhter-F (SEQ ID NO: 58). Subsequently, a Left-TALEN-pdc3 fragment was amplified by PCR using Left-TALEN-pdc3 as a template with primers of cipCpro-Life-TALEN-F (SEQ ID NO: 94) and LifeTALEN-adhter-R (SEQ ID NO: 95). These two fragments contained regions overlapping with each other by 15 bases. These two fragments were ligated using In-Fusion HD cloning kit (Clontech Laboratories, Inc.) to obtain a plasmid pcipC-Left-TALEN-pdc3 containing LeftTALEN-pdc3.

Likewise, the polynucleotide encoding RightTALEN for the pdc3 gene was inserted to the expression vector pUC18-PcipC-Tadh for *R. delemar* prepared in the paragraph (1) to prepare a vector for expression of TALEN under control of the cipC promoter and the adh1 terminator. Specifically, a vector fragment was amplified by PCR using pUC18-PcipC-Tadh as a template with primers of cipCpro-R (SEQ ID NO: 93) and adhter-F (SEQ ID NO: 58). Subsequently, a Right-TALEN-pdc3 fragment was amplified by PCR using Right-TALEN-pdc3 as a template with primers of cipCpro-Life-TALEN-F (SEQ ID NO: 94) and LifeTALEN-adhter-R (SEQ ID NO: 95). These two fragments contained regions overlapping with each other by 15 bases. These two fragments were ligated using In-Fusion HD cloning kit (Clontech Laboratories, Inc.) to obtain a plasmid pcipC-Right-TALEN-pdc3 containing RightTALEN-pdc3.

(3) Preparation of Exonuclease Expression Vector

An exonuclease gene fragment was amplified by PCR using the plasmid pldh-exo1 prepared in Example 1(4) as a template with primers of cipCpro-exo1-F (SEQ ID NO: 96) and exo1-adhter-R (SEQ ID NO: 97). A vector fragment was amplified by PCR using the plasmid pUC18-PcipC-Tadh prepared in the paragraph (1) as a template with primers of cipCpro-R (SEQ ID NO: 93) and adhter-F (SEQ ID NO: 58). These two fragments contained regions overlapping with each other by 15 bases. These two fragments were ligated using In-Fusion HD cloning kit (Clontech Laboratories, Inc.) to obtain a plasmid pcipC-exo1.

(4) Preparation of Plasmid for trpC Knock-in Targeting Pdc3 Gene Locus

A plasmid ptrpC-knock-in (pdc3) for removing pdc3 gene ORF and knocking-in the trpC gene region at the pdc3 gene locus was prepared. Specifically, a pUC18 vector fragment amplified using pUC18 as a template with primers of pUC18-Pae1-F3 (SEQ ID NO: 69) and pUC18-Hindi-R3 (SEQ ID NO: 70), a pdc3 gene promoter fragment amplified using the genomic DNA of the 5557 strain as a template with primers of pdc3-upstr-F (SEQ ID NO: 98) and pdc3-upstr-R2 (SEQ ID NO: 99), and a pdc3 gene terminator fragment amplified using the genomic DNA of the 5557 strain as a template with primers of pdc3-downstr-F2 (SEQ ID NO: 100) and pdc3-downstr-R (SEQ ID NO: 101) were ligated using In-Fusion HD Cloning Kit (Clontech Laboratories, Inc.) to prepare a plasmid pknock-in (pdc3).

Subsequently, a DNA fragment amplified using pknock-in (pdc3) as a template and primers pdc3-upstr-R (SEQ ID NO: 102) and pdc3-downstr-F (SEQ ID NO: 103), and a trpC gene region fragment amplified using the genomic DNA of the 5557 strain as a template with primers of trpCpro-R (SEQ ID NO: 73) and trpCter-F (SEQ ID NO: 74) were ligated using In-Fusion HD Cloning Kit (Clontech Laboratories, Inc.) to prepare a plasmid ptrpC-knock-in (pdc3).

(5) Preparation of Single-Stranded DNA

Single-stranded DNA was obtained by the same procedures as in Example 1(6) except that: ptrpC-knock-in (pdc3) was used as a PCR template; and pdc3-upstr-F2 (SEQ ID NO: 104) and pdc3-downstr-R2-P (SEQ ID NO: 105; 5'-terminally phosphorylated primer) were used as PCR primers.

(6) Gene Transfer Using Particle Gun

By the same procedures as in Example 1(7), a DNA-gold particle solution containing single-stranded DNA was prepared, and the spores of the 02T6 strain was subjected to gene transfer using this solution, followed by culturing the obtained spores. The single-stranded DNA used was the single-stranded DNA prepared in the paragraph (5). The TALEN expression vectors used were the pcipC-Left-TALEN-pdc3 and the pcipC-RightTALEN-pdc3 prepared in the paragraph (2). The exonuclease expression vector used was the pcipC-exo1 prepared in the paragraph (4). The concentration ratio among pcipC-LeftTALEN-pdc3, pcipC-RightTALEN-pdc3, pcipC-exo1, and single-stranded DNA in the DNA solution was set to approximately 1:1:1:2.

(7) Selection of Pdc3 Gene-Deficient Strain

The spores were collected from the fungal cells cultured in the paragraph (6). The isolation of fungal strains and preparation of a genome template solution were performed by the same procedures as in Example 1(8). Subsequently, a pdc3 gene-deficient strain with the trpC gene region fragment knocked-in at the pdc3 gene locus was selected by colony PCR using the genome template solution as a template. The colony PCR was performed using the genome template solution, primers pdc3-up (SEQ ID NO: 106) and trpC(d)-1 (SEQ ID NO: 80), and KOD FX Neo (Toyobo Co., Ltd.). The colony PCR using these primers amplifies a DNA fragment having an appropriate length if the trpC gene region fragment is knocked-in at the pdc3 gene locus. By the colony PCR, a fungal strain with the DNA amplification fragment obtained was obtained as a pdc3 gene-deficient strain 02T6Δpdc3.

(8) Evaluation of Pyruvate Decarboxylase Activity

The fungal cells of the 02T6 strain, the 02T6Δpdc strain and the 02T6Δpdc3 strain were cultured in the same way as in Example 2(1), and their pyruvate decarboxylase activity was evaluated in the same way as in Example 2(2).

The results are shown in Table 5. The PDC activity was decreased to approximately 20% in the 02T6Δpdc strain, but remained at approximately 89% in the 02T6Δpdc3 strain, as compared with the 02T6 strain as a parent strain. The decrease in PDC activity contributes to the suppression of production of ethanol which is a by-product of organic acid production. It was therefore shown that: the 02T6Δpdc3 strain is inferior in organic acid productivity to the 02T6Δpdc strain; and deficiency in pdc gene among pyruvate decarboxylase-encoding genes is effective for improvement in organic acid productivity.

TABLE 5

|  | O2T6 strain | 02T6Δpdc strain | 02T6Δpdc3 strain |
| --- | --- | --- | --- |
| PDC activity (U/g-protein) | 1939 | 395 | 1721 |

Reference Example 1 Quantification of Glucose, Fumaric Acid, Malic Acid, Succinic Acid and Ethanol in Cultures <Analysis Conditions>

Glucose, fumaric acid, malic acid, succinic acid and ethanol in culture supernatants were quantified using a HPLC apparatus LaChrom Elite (manufactured by Hitachi High-Technologies Corp.). The analytical column used was a polymer column ICSep ICE-ION-300 for organic acid analysis (7.8 mm I.D.×300 mm, manufactured by Transgenomic, Inc.) connected with a guard column ICSep ION-300 Guard Column Cartridge (4.0 mm I.D.×20 mm, manufactured by Transgenomic, Inc.). Elution was performed under conditions of 0.01 N sulfuric acid as an eluent, a flow rate of 0.5 mL/min, and a column temperature of 50° C. A differential refractive index detector (RI detector) was used in the detection of glucose and ethanol. A UV detector (detection wavelength: 210 nm) was used in the detection of fumaric acid, malic acid and succinic acid. Each culture supernatant sample to be subjected to HPLC analysis was diluted 3-fold in advance with a 0.86 M sodium sulfate solution and then appropriately diluted with 37 mM sulfuric acid. Then, insoluble matter was removed using AcroPrep 96-well Filter Plates (0.2 μm GHP membrane, manufactured by Pall Corp.).

<Calculation of the Selectivity>

The selectivity of each substance refers to the ratio of the equivalent of the substance actually obtained from cultures to the maximum equivalent of the substance theoretically obtainable from the cultures (theoretical maximum amount) calculated from the amount of glucose consumed in the cultures. Specifically, the selectivity is determined according to the following expression:

The selectivity=Equivalent of the product/Theoretical maximum amount wherein Theoretical maximum amount=Equivalent of glucose consumed×[Correction coefficient]

The theoretical maximum amount and the correction coefficient of the substance to be measured are as follows:

[Theoretical maximum amount] [Correction coefficient]
Ethanol: from 1 mol to 2 mol at maximum of glucose ½
Fumaric acid: from 2 mol to 3 mol at maximum of glucose ⅔
Malic acid: from 2 mol to 3 mol at maximum of glucose ⅔
Succinic acid: from 2 mol to 3 mol at maximum of glucose ⅔

What is claimed is:

1. A method for improving organic acid productivity of a *Rhizopus* fungus, comprising:
deleting or inactivating a pdc gene in the *Rhizopus* fungus, wherein
the pdc gene is at least one polynucleotide selected from the group consisting of:
a polynucleotide consisting of the nucleotide sequence set forth in SEQ ID NO: 1;
a polynucleotide consisting of a nucleotide sequence having at least 90% identity to the nucleotide sequence set forth in SEQ ID NO: 1 and that encodes a polypeptide which has pyruvate decarboxylase activity;
a polynucleotide comprising a nucleotide sequence that has 1-20 deletions, insertions, substitutions or additions of nucleotides as compared to the nucleotide sequence set forth in SEQ ID NO: 1 and that encodes a polypeptide which has pyruvate decarboxylase activity;
a polynucleotide encoding a polypeptide which consists of the amino acid sequence set forth in SEQ ID NO: 2;
a polynucleotide encoding a polypeptide which consists of an amino acid sequence having at least 90% identity to the amino acid sequence set forth in SEQ ID NO: 2 and that has pyruvate decarboxylase activity; and
a polynucleotide encoding a polypeptide which comprises an amino acid sequence that has 1-10 deletions, insertions, substitutions or additions of amino acid residues as compared to the amino acid sequence set forth in SEQ ID NO: 2 and that has pyruvate decarboxylase activity;
and culturing the fungus to produce the organic acid,
wherein the organic acid is selected from the group consisting of fumaric acid, lactic acid, succinic acid, malic acid, and α-ketoglutaric acid,
and wherein production of the organic acid is improved in the *Rhizopus* fungus compared to the production of the organic acid before deletion or inactivation of the pdc gene.

2. The method of claim 1, wherein the *Rhizopus* is *Rhizopus oryzae* or *Rhizopus delemar*.

3. The method of claim 1, further comprising collecting the organic acid from the culture after the culturing.

4. The method of claim 1, wherein the organic acid is fumaric acid, succinic acid or malic acid.

5. The method of claim 1, wherein the culturing is aerobic culturing.

6. The method of claim 1, wherein the deleting or inactivating of the pdc gene is performed by genome editing of a pdc gene locus using a programmable nuclease.

7. The method of claim 6, wherein the genome editing is transfer of TALEN peptides or polynucleotides encoding the TALEN peptides to the *Rhizopus* fungus.

8. The method of claim 7, wherein the TALEN peptides consist of the following polypeptides (L) and (R):
the polypeptide (L) being
a polypeptide which consists of the amino acid sequence set forth in SEQ ID NO: 4;
a polypeptide which consists of an amino acid sequence having at least 95% identity to the amino acid sequence set forth in SEQ ID NO: 4 and has a TAL effector targeting the sequence set forth in SEQ ID NO: 9 and a DNA cleavage domain consisting of Fok1-like DNA nuclease;
a polypeptide which is encoded by a polynucleotide consisting of the nucleotide sequence set forth in SEQ ID NO: 3; or
a polypeptide which is encoded by a polynucleotide consisting of a nucleotide sequence having at least 95% identity to the nucleotide sequence set forth in SEQ ID NO: 3 and has a TAL effector targeting the sequence set forth in SEQ ID NO: 9 and a DNA cleavage domain consisting of Fok1-like DNA nuclease, and
the polypeptide (R) being
a polypeptide which consists of the amino acid sequence set forth in SEQ ID NO: 6;
a polypeptide which consists of an amino acid sequence having at least 95% identity to the amino acid sequence set forth in SEQ ID NO: 6 and has a TAL effector targeting the sequence set forth in SEQ ID NO: 10 and a DNA cleavage domain consisting of Fok1-like DNA nuclease;
a polypeptide which is encoded by a polynucleotide consisting of the nucleotide sequence set forth in SEQ ID NO: 5; or
a polypeptide which is encoded by a polynucleotide consisting of a nucleotide sequence having at least 95% identity to the nucleotide sequence set forth in SEQ ID NO: 5 and has a TAL effector targeting the sequence set forth in SEQ ID NO: 10 and a DNA cleavage domain consisting of Fok1-like DNA nuclease.

9. The method of claim 7, further comprising transferring an exonuclease or a polynucleotide encoding the exonuclease to the *Rhizopus* fungus.

* * * * *

SEQUENCE LISTING

<160> NUMBER OF SEQ ID NOS: 106

<210> SEQ ID NO 1
<211> LENGTH: 1683
<212> TYPE: DNA
<213> ORGANISM: Rhizopus delemar
<220> FEATURE:
<223> OTHER INFORMATION: pdc gene

<400> SEQUENCE: 1

```
atgcctgcta ttaaaatcgg tcaacatctc cttaaccgtc ttaaggaaat caacattgat      60
gttgtctttg gtgttcctgg tgatttcaac atgcccttgt tggatatcat tgaagatgac     120
ccagaactta cctggggtaa caatgccaac gaattgaatg catcttatgc agctgatggt     180
tatgctcgta ttcgtggtgc aggtgctgtt gtcactacct ttggtgtagg tgagctgtct     240
gctgtcaacg gtattgctgg ttcatactct gagatgcttc ccgtgattca catcgtcggt     300
actccttcta ctaaatccca agctgccggt gccatgcttc accactcttt gggtgacggt     360
aactttgatg tgttcttcaa catgtcctcc atgattgcct gtgcctctgc tcacctcaag     420
aaacaaacgg ccattgcaga aattgaccgt gtgatctccc aagctgttct ctccaagcgt     480
acaggttaca ttggtatccc tatcgatctg atcaagactg aggttgaagt acctgagccc     540
attcctgccc tcaagaccga attacccaaa aacccagctg atgtccaagc gattgccttg     600
agagtggtca cggatgcgat cgccaaagcc caattccctg tgattgttgt cgatggctgt     660
gtgcttcgcc agagatgcca aaaggcagta caagccttta tcgaacgtac tggtttccct     720
acttatgttg ctcctatggg taagggtgcc gttgacgaat cctctgtgag ttaccgtggc     780
tgctactcgg gtaatgtcac attggaagca gtgaatgaag agatcaagca agccgatttg     840
atcatcgaag tgggctccat caagtctgat ttcaacacgg gtaacttttc atactctctc     900
gaccgttcca agacgatcac cttgcactcc tttgccacca tcgtgttttg tgctgaatac     960
caaaaggtct ccatgctcga attcattcct ctcttgaccc aagcccttcc cgaacaaccc    1020
cgtcaattca acctgggtcc ccgcccaaga cccgtaccta tccaacccgg taccgaaatc    1080
acccacaact acttttggca caggtaccc gaattcatgg atgagaacgc cattgtctgt    1140
gccgagaccg gtacagctga atttgcttca ctcaacatgg acggacccaa gggaacgact    1200
tatatcaccc aattcctctg gggctctatc ggtttctcag taggtgccgc tgtgggtgct    1260
```

-continued

```
gcgatcgccg ctcgtgatcg tcgtgtgtat ctctttgtcg gtgatggttc cttccaattg    1320
acctgtcaag aaatctctgg cttccttcgc catggtttga cacctgtgat cttcttgctg    1380
aacaatgacg gttacttgat cgaaaaactc attcacggtc ccgaacgtgc ctataataac    1440
tttcaaatgt gggaatacag caagacgctt gattatttcg gtgctcatct tgaacacaac    1500
aagtccatgg gtgttcctcc cgttggcttc gaaggcaagg tagccacacg cgatgaattt    1560
gaatccgcca tgagacaggt tcaagccaat cctgacaaga ttcatttcct tgaagtcatt    1620
atgcctcaat ttgactctcc tcgtgaactt gaactcttgg ttgccaactc tgaaaaccgt    1680
taa                                                                   1683
```

<210> SEQ ID NO 2
<211> LENGTH: 560
<212> TYPE: PRT
<213> ORGANISM: Rhizopus delemar
<220> FEATURE:
<223> OTHER INFORMATION: pyruvate dehydrogenase 1

<400> SEQUENCE: 2

```
Met Pro Ala Ile Lys Ile Gly Gln His Leu Leu Asn Arg Leu Lys Glu
1               5                   10                  15

Ile Asn Ile Asp Val Val Phe Gly Val Pro Gly Asp Phe Asn Met Pro
            20                  25                  30

Leu Leu Asp Ile Ile Glu Asp Pro Glu Leu Thr Trp Gly Asn Asn
        35                  40                  45

Ala Asn Glu Leu Asn Ala Ser Tyr Ala Ala Asp Gly Tyr Ala Arg Ile
    50                  55                  60

Arg Gly Ala Gly Ala Val Val Thr Thr Phe Gly Val Gly Glu Leu Ser
65                  70                  75                  80

Ala Val Asn Gly Ile Ala Gly Ser Tyr Ser Glu Met Leu Pro Val Ile
                85                  90                  95

His Ile Val Gly Thr Pro Ser Thr Lys Ser Gln Ala Ala Gly Ala Met
            100                 105                 110

Leu His His Ser Leu Gly Asp Gly Asn Phe Asp Val Phe Phe Asn Met
        115                 120                 125

Ser Ser Met Ile Ala Cys Ala Ser Ala His Leu Lys Lys Gln Thr Ala
    130                 135                 140

Ile Ala Glu Ile Asp Arg Val Ile Ser Gln Ala Val Leu Ser Lys Arg
145                 150                 155                 160

Thr Gly Tyr Ile Gly Ile Pro Ile Asp Leu Ile Lys Thr Glu Val Glu
                165                 170                 175

Val Pro Glu Pro Ile Pro Ala Leu Lys Thr Glu Leu Pro Lys Asn Pro
            180                 185                 190

Ala Asp Val Gln Ala Ile Ala Leu Arg Val Val Thr Asp Ala Ile Ala
        195                 200                 205

Lys Ala Gln Phe Pro Val Ile Val Val Asp Gly Cys Val Leu Arg Gln
    210                 215                 220

Arg Cys Gln Lys Ala Val Gln Ala Phe Ile Glu Arg Thr Gly Phe Pro
225                 230                 235                 240

Thr Tyr Val Ala Pro Met Gly Lys Gly Ala Val Asp Glu Ser Ser Val
                245                 250                 255

Ser Tyr Arg Gly Cys Tyr Ser Gly Asn Val Thr Leu Glu Ala Val Asn
            260                 265                 270

Glu Glu Ile Lys Gln Ala Asp Leu Ile Ile Glu Val Gly Ser Ile Lys
        275                 280                 285
```

| | | | | | | | | | | | |
|---|---|---|---|---|---|---|---|---|---|---|---|
Ser | Asp | Phe | Asn | Thr | Gly | Asn | Phe | Ser | Tyr | Ser | Leu | Asp | Arg | Ser | Lys
  | 290 | | | | 295 | | | | 300 | | |

Thr Ile Thr Leu His Ser Phe Ala Thr Ile Val Phe Cys Ala Glu Tyr
305                 310                 315                 320

Gln Lys Val Ser Met Leu Glu Phe Ile Pro Leu Leu Thr Gln Ala Leu
            325                 330                 335

Pro Glu Gln Pro Arg Gln Phe Asn Leu Gly Pro Arg Pro Arg Pro Val
        340                 345                 350

Pro Ile Gln Pro Gly Thr Glu Ile Thr His Asn Tyr Phe Trp His Lys
    355                 360                 365

Val Pro Glu Phe Met Asp Glu Asn Ala Ile Val Cys Ala Glu Thr Gly
370                 375                 380

Thr Ala Glu Phe Ala Ser Leu Asn Met Asp Gly Pro Lys Gly Thr Thr
385                 390                 395                 400

Tyr Ile Thr Gln Phe Leu Trp Gly Ser Ile Gly Phe Ser Val Gly Ala
            405                 410                 415

Ala Val Gly Ala Ala Ile Ala Ala Arg Asp Arg Val Tyr Leu Phe
        420                 425                 430

Val Gly Asp Gly Ser Phe Gln Leu Thr Cys Gln Glu Ile Ser Gly Phe
    435                 440                 445

Leu Arg His Gly Leu Thr Pro Val Ile Phe Leu Leu Asn Asn Asp Gly
450                 455                 460

Tyr Leu Ile Glu Lys Leu Ile His Gly Pro Glu Arg Ala Tyr Asn Asn
465                 470                 475                 480

Phe Gln Met Trp Glu Tyr Ser Lys Thr Leu Asp Tyr Phe Gly Ala His
            485                 490                 495

Leu Glu His Asn Lys Ser Met Gly Val Pro Val Gly Phe Glu Gly
        500                 505                 510

Lys Val Ala Thr Arg Asp Glu Phe Glu Ser Ala Met Arg Gln Val Gln
            515                 520                 525

Ala Asn Pro Asp Lys Ile His Phe Leu Glu Val Ile Met Pro Gln Phe
    530                 535                 540

Asp Ser Pro Arg Glu Leu Glu Leu Leu Val Ala Asn Ser Glu Asn Arg
545                 550                 555                 560

<210> SEQ ID NO 3
<211> LENGTH: 3006
<212> TYPE: DNA
<213> ORGANISM: Artificial Sequence
<220> FEATURE:
<223> OTHER INFORMATION: LeftTALEN-pdc

<400> SEQUENCE: 3

```
atggactaca aagaccatga cggtgattat aaagatcatg acatcgatta caaggatgac      60
gatgacaaga tggccccaa gaagaagagg aaggtgggca ttcaccgcgg ggtacctatg     120
gtggacttga ggacactcgg ttattcgcaa cagcaacagg agaaaatcaa gcctaaggtc     180
aggagcaccg tcgcgcaaca ccacgaggcg cttgtgggc atggcttcac tcatgcgcat     240
attgtcgcgc tttcacagca ccctgcggcg cttgggacgg tgctgtcaa ataccaagat     300
atgattgcgg ccctgcccga agccacgcac gaggcaattg taggggtcgg taaacagtgg     360
tcgggagcgc gagcacttga ggcgctgctg actgtggcgg gtgagcttag ggggcctccg     420
ctccagctcg acaccgggca gctgctgaag atcgcgaaga gaggggagt aacagcggta     480
gaggcagtgc acgcctggcg caatgcgctc accggggccc ccttgaactt gaccccagac     540
```

```
caggtagtcg caatcgcgaa caataatggg ggaaagcaag ccctggaaac cgtgcaaagg      600
ttgttgccgg tcctttgtca agaccacggc ctgactcccg atcaagttgt agcgattgcg      660
tcgcatgacg gagggaaaca agcattggag actgtccaac ggctccttcc cgtgttgtgt      720
caagcccacg gtttgacgcc tgcacaagtg gtcgccatcg ccagccatga tggcggtaag      780
caggcgctgg aaacagtaca gcgcctgctg cctgtactgt gccaggatca tggactgacc      840
ccagaccagg tagtcgcaat cgcgtcaaac ggagggggaa agcaagccct ggaaaccgtg      900
caaaggttgt tgccggtcct ttgtcaagac cacggcctga ccccagacca ggtagtcgca      960
atcgcgaaca ataatggggg aaagcaagcc ctggaaaccg tgcaaaggtt gttgccggtc     1020
ctttgtcaag accatggcct gactcccgat caagttgtag cgattgcgtc gcatgacgga     1080
gggaaacaag cattggagac tgtccaacgg ctccttcccg tgttgtgtca agcccacggt     1140
ttgacgcctg cacaagtggt cgccatcgcc agcaatggcg gcggtaagca ggcgctggaa     1200
acagtacagc gcctgctgcc tgtactgtgc caggatcatg gactgacccc agaccaggta     1260
gtcgcaatcg cgtcgaacat ggggggaaag caagccctgg aaaccgtgca aaggttgttg     1320
ccggtccttt gtcaagacca cggcctgacc ccagaccagg tagtcgcaat cgcgtcaaac     1380
ggagggggaa agcaagccct ggaaaccgtg caaaggttgt tgccggtcct ttgtcaagac     1440
cacggcctga ctcccgatca agttgtagcg attgcgtcca acggtggagg gaaacaagca     1500
ttggagactg tccaacggct ccttcccgtg ttgtgtcaag cccatggatt gaccccagac     1560
caggtagtcg caatcgcgtc aaacattggg ggaaagcaag ccctggaaac cgtgcaaagg     1620
ttgttgccgg tcctttgtca agaccacggc ctgactcccg atcaagttgt agcgattgcg     1680
tcgaacattg agggaaaaca agcattggag actgtccaac ggctccttcc cgtgttgtgt     1740
caagcccacg gtttgacgcc tgcacaagtg gtcgccatcg ccagcaatat tggcggtaag     1800
caggcgctgg aaacagtaca gcgcctgctg cctgtactgt gccaggatca tggactgacc     1860
ccagaccagg tagtcgcaat cgcgtcaaac attgggggaa agcaagccct ggaaaccgtg     1920
caaaggttgt tgccggtcct ttgtcaagac cacggcctga ccccagacca ggtagtcgca     1980
atcgcgtcaa acggaggggg aaagcaagcc ctggaaaccg tgcaaaggtt gttgccggtc     2040
ctttgtcaag accacggcct gactcccgat caagttgtag cgattgcgtc gcatgacgga     2100
gggaaacaag cattggagac tgtccaacgg ctccttcccg tgttgtgtca agcccacggt     2160
ctgacacccg aacaggtggt cgccattgct aataataacg gaggacggcc agccttggag     2220
tccatcgtag cccaattgtc caggcccgat cccgcgttgg ctgcgttaac gaatgaccat     2280
ctggtggcgt tggcatgtct tggtggacga cccgcgctcg atgcagtcaa aaagggtctg     2340
cctcatgctc ccgcattgat caaaagaacc aaccggcgga ttcccgagag aacttcccat     2400
cgagtcgcgg gatcccaact agtcaaaagt gaactggagg agaagaaatc tgaacttcgt     2460
cataaattga aatatgtgcc tcatgaatat attgaattaa ttgaaattgc agaaattcc      2520 actcaggata gaattcttga aatgaaggta atggaatttt ttatgaaagt ttatggatat     2580
agaggtaaac atttgggtgg atcaaggaaa ccggacggag caatttatac tgtcggatct     2640
cctattgatt acgtgtgat cgtggatact aaagcttata gcgagggtta taatctgcca      2700
attggccaag cagatgaaat gcaacgatat gtcgaagaaa atcaaacacg aaacaaacat     2760
atcaacccta tgaatggtg gaaagtctat ccatcttctg taacggaatt taagttttta      2820
tttgtgagtg gtcactttaa aggaaactac aaagctcagc ttacacgatt aaatcatatc     2880
```

```
actaattgta atggagctgt tcttagtgta gaagagcttt taattggtgg agaaatgatt    2940
aaagccggca cattaacctt agaggaagtc agacggaaat ttaataacgg cgagataaac    3000
tttaa                                                                3006
```

<210> SEQ ID NO 4
<211> LENGTH: 1001
<212> TYPE: PRT
<213> ORGANISM: Artificial Sequence
<220> FEATURE:
<223> OTHER INFORMATION: LeftTALEN-pdc

<400> SEQUENCE: 4

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Asn Asn Asn Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Ser His Asp Gly
210                 215                 220

Gly Lys Gln Ala Leu Glu Thr Val Gln Arg Leu Leu Pro Val Leu Cys
225                 230                 235                 240

Gln Ala His Gly Leu Thr Pro Ala Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser Asn Gly Gly Gly Lys Gln Ala Leu Glu Thr Val Gln Arg Leu Leu
290                 295                 300

Pro Val Leu Cys Gln Asp His Gly Leu Thr Pro Asp Gln Val Val Ala
305                 310                 315                 320

Ile Ala Asn Asn Asn Gly Gly Lys Gln Ala Leu Glu Thr Val Gln Arg
                325                 330                 335
```

```
Leu Leu Pro Val Leu Cys Gln Asp His Gly Leu Thr Pro Asp Gln Val
                340                 345                 350

Val Ala Ile Ala Ser His Asp Gly Gly Lys Gln Ala Leu Glu Thr Val
            355                 360                 365

Gln Arg Leu Leu Pro Val Leu Cys Gln Ala His Gly Leu Thr Pro Ala
        370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Ile Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Ala Gln Val Val Ala
            580                 585                 590

Ile Ala Ser Asn Ile Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Ser His Asp Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Asn Asn Asn Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
```

|  |  | 755 |  |  |  | 760 |  |  |  | 765 |  |
| --- | --- | --- | --- | --- | --- | --- | --- | --- | --- | --- | --- |

Gly Arg Pro Ala Leu Asp Ala Val Lys Lys Gly Leu Pro His Ala Pro
770                 775                 780

Ala Leu Ile Lys Arg Thr Asn Arg Arg Ile Pro Glu Arg Thr Ser His
785                 790                 795                 800

Arg Val Ala Gly Ser Gln Leu Val Lys Ser Glu Leu Glu Glu Lys Lys
                805                 810                 815

Ser Glu Leu Arg His Lys Leu Lys Tyr Val Pro His Glu Tyr Ile Glu
                820                 825                 830

Leu Ile Glu Ile Ala Arg Asn Ser Thr Gln Asp Arg Ile Leu Glu Met
                835                 840                 845

Lys Val Met Glu Phe Phe Met Lys Val Tyr Gly Tyr Arg Gly Lys His
850                 855                 860

Leu Gly Gly Ser Arg Lys Pro Asp Gly Ala Ile Tyr Thr Val Gly Ser
865                 870                 875                 880

Pro Ile Asp Tyr Gly Val Ile Val Asp Thr Lys Ala Tyr Ser Gly Gly
                885                 890                 895

Tyr Asn Leu Pro Ile Gly Gln Ala Asp Glu Met Gln Arg Tyr Val Glu
                900                 905                 910

Glu Asn Gln Thr Arg Asn Lys His Ile Asn Pro Asn Glu Trp Trp Lys
                915                 920                 925

Val Tyr Pro Ser Ser Val Thr Glu Phe Lys Phe Leu Phe Val Ser Gly
930                 935                 940

His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
                965                 970                 975

Gly Glu Met Ile Lys Ala Gly Thr Leu Thr Leu Glu Glu Val Arg Arg
                980                 985                 990

Lys Phe Asn Asn Gly Glu Ile Asn  Phe
                995                 1000

<210> SEQ ID NO 5
<211> LENGTH: 3006
<212> TYPE: DNA
<213> ORGANISM: Artificial Sequence
<220> FEATURE:
<223> OTHER INFORMATION: RightTALEN-pdc

<400> SEQUENCE: 5

| atggactaca | agaccatga  | cggtgattat | aaagatcatg | acatcgatta | caaggatgac | 60 |
| atgacaaga  | tggcccccaa | gaagaagagg | aaggtgggca | ttcaccgcgg | ggtacctatg | 120 |
| gtggacttga | ggacactcgg | ttattcgcaa | cagcaacagg | agaaaatcaa | gcctaaggtc | 180 |
| aggagcaccg | tcgcgcaaca | ccacgaggcg | cttgtggggc | atggcttcac | tcatgcgcat | 240 |
| attgtcgcgc | tttcacagca | ccctgcgggc | cttgggacgg | tggctgtcaa | ataccaagat | 300 |
| atgattgcgg | ccctgcccga | agccacgcac | gaggcaattg | taggggtcgg | taaacagtgg | 360 |
| tcgggagcgc | gagcacttga | ggcgctgctg | actgtggcgg | gtgagcttag | ggggcctccg | 420 |
| ctccagctcg | acaccgggca | gctgctgaag | atcgcgaaga | gaggggagt  | aacagcggta | 480 |
| gaggcagtgc | acgcctggcg | caatgcgctc | accgggccc  | ccttgaactt | gaccccagac | 540 |
| caggtagtcg | caatcgcgtc | aaacggaggg | ggaaagcaag | ccctggaaac | cgtgcaaagg | 600 |
| ttgttgccgg | tcctttgtca | agaccacggc | ctgactcccg | atcaagttgt | agcgattgcg | 660 |

```
aataacaatg gagggaaaca agcattggag actgtccaac ggctccttcc cgtgttgtgt      720
caagcccacg gtttgacgcc tgcacaagtg gtcgccatcg ccagcaatat tggcggtaag      780
caggcgctgg aaacagtaca gcgcctgctg cctgtactgt gccaggatca tggactgacc      840
ccagaccagg tagtcgcaat cgcgtcaaac ggagggggaa agcaagccct ggaaaccgtg      900
caaaggttgt tgccggtcct ttgtcaagac cacggcctga ccccagacca ggtagtcgca      960
atcgcgtcaa acggaggggg aaagcaagcc ctggaaaccg tgcaaaggtt gttgccggtc     1020
ctttgtcaag accacggcct gactcccgat caagttgtag cgattgcgtc gaacggtgga     1080
gggaaacaag cattggagac tgtccaacgg ctccttcccg tgttgtgtca gcccacggt      1140 ttgacgcctg cacaagtggt cgccatcgcc agccatgatg gcggtaagca ggcgctggaa     1200
acagtacagc gcctgctgcc tgtactgtgc caggatcatg gactgacccc agaccaggta     1260
gtcgcaatcg cgtcacatga cggggaaag caagccctgg aaaccgtgca aaggttgttg     1320
ccggtccttt gtcaagacca cggcctgacc ccagaccagg tagtcgcaat cgcgtcaaac     1380 ggaggggaa agcaagccct ggaaaccgtg caaaggttgt tgccggtcct ttgtcaagac     1440
cacggcctga ctcccgatca agttgtagcg attgcgtcca acggtggagg gaaacaagca     1500
ttggagactg tccaacggct ccttcccgtg ttgtgtcaag cccatggatt gaccccagac     1560
caggtagtcg caatcgcgtc aaacattggg ggaaagcaag ccctggaaac cgtgcaaagg     1620
ttgttgccgg tcctttgtca agaccacggc ctgactcccg atcaagttgt agcgattgcg     1680
tcgaacattg agggaaaaca agcattggag actgtccaac ggctccttcc cgtgttgtgt     1740
caagcccacg gtttgacgcc tgcacaagtg gtcgccatcg ccaacaacaa cggcggtaag     1800
caggcgctgg aaacagtaca gcgcctgctg cctgtactgt gccaggatca tggactgacc     1860
ccagaccagg tagtcgcaat cgcgtcaaac attgggggaa agcaagccct ggaaaccgtg     1920
caaaggttgt tgccggtcct ttgtcaagac cacggcctga ccccagacca ggtagtcgca     1980
atcgcgtcac atgacggggg aaagcaagcc ctggaaaccg tgcaaaggtt gttgccggtc     2040
ctttgtcaag accatggcct gactcccgat caagttgtag cgattgcgaa taacaatgga     2100
gggaaacaag cattggagac tgtccaacgg ctccttcccg tgttgtgtca gcccacggt      2160 ctgacacccg aacaggtggt cgccattgct aataataacg gaggacggcc agccttggag     2220
tccatcgtag cccaattgtc caggcccgat cccgcgttgg ctgcgttaac gaatgaccat     2280
ctggtggcgt tggcatgtct tggtggacga cccgcgctcg atgcagtcaa aaagggtctg     2340
cctcatgctc ccgcattgat caaaagaacc aaccggcgga ttcccgagag aacttcccat     2400
cgagtcgcgg gatcccaact agtcaaaagt gaactggagg agaagaaatc tgaacttcgt     2460
cataaattga aatatgtgcc tcatgaatat attgaattaa ttgaaattgc agaaattcc      2520 actcaggata gaattcttga aatgaaggta atggaatttt ttatgaaagt ttatggatat     2580
agaggtaaac atttgggtgg atcaaggaaa ccggacggag caatttatac tgtcggatct     2640
cctattgatt acgtgtgat cgtggatact aaagcttata gcggaggtta taatctgcca      2700
attggccaag cagatgaaat gcaacgatat gtcgaagaaa atcaaacacg aaacaaacat     2760
atcaacccta tgaatggtg aaagtctat ccatcttctg taacgaatt taagttttta       2820 tttgtgagtg gtcactttaa aggaaactac aaagctcagc ttacacgatt aaatcatatc     2880
actaattgta atggagctgt tcttagtgta aagagctttt taattggtgg agaaatgatt     2940
aaagccggca cattaacctt agaggaagtc agacggaaat ttaataacgg cgagataaac     3000
ttttaa                                                              3006
```

<210> SEQ ID NO 6
<211> LENGTH: 1001
<212> TYPE: PRT
<213> ORGANISM: Artificial Sequence
<220> FEATURE:
<223> OTHER INFORMATION: RightTALEN-pdc

<400> SEQUENCE: 6

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Gly Gly Gly Lys
            180                 185                 190

Gln Ala Leu Glu Thr Val Gln Arg Leu Leu Pro Val Leu Cys Gln Asp
        195                 200                 205

His Gly Leu Thr Pro Asp Gln Val Val Ala Ile Ala Asn Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Ala Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Asp His Gly Leu Thr Pro Asp Gln Val Val Ala Ile Ala
        275                 280                 285

Ser Asn Gly Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Asp His Gly Leu Thr Pro Asp Gln Val
            340                 345                 350

Val Ala Ile Ala Ser Asn Gly Gly Gly Lys Gln Ala Leu Glu Thr Val
        355                 360                 365
```

-continued

```
Gln Arg Leu Leu Pro Val Leu Cys Gln Ala His Gly Leu Thr Pro Ala
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
            420                 425                 430

Leu Glu Thr Val Gln Arg Leu Leu Pro Val Leu Cys Gln Asp His Gly
        435                 440                 445

Leu Thr Pro Asp Gln Val Val Ala Ile Ala Ser Asn Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Asp Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Ala Gln Val Val Ala
            580                 585                 590

Ile Ala Asn Asn Asn Gly Gly Lys Gln Ala Leu Glu Thr Val Gln Arg
        595                 600                 605

Leu Leu Pro Val Leu Cys Gln Asp His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Asp His Gly Leu Thr Pro Asp
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Asp His Gly Leu Thr
        675                 680                 685

Pro Asp Gln Val Val Ala Ile Ala Asn Asn Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Asn Asn Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
        755                 760                 765

Gly Arg Pro Ala Leu Asp Ala Val Lys Lys Gly Leu Pro His Ala Pro
    770                 775                 780
```

```
Ala Leu Ile Lys Arg Thr Asn Arg Arg Ile Pro Glu Arg Thr Ser His
785                 790                 795                 800

Arg Val Ala Gly Ser Gln Leu Val Lys Ser Glu Leu Glu Glu Lys Lys
            805                 810                 815

Ser Glu Leu Arg His Lys Leu Lys Tyr Val Pro His Glu Tyr Ile Glu
        820                 825                 830

Leu Ile Glu Ile Ala Arg Asn Ser Thr Gln Asp Arg Ile Leu Glu Met
            835                 840                 845

Lys Val Met Glu Phe Phe Met Lys Val Tyr Gly Tyr Arg Gly Lys His
    850                 855                 860

Leu Gly Ser Arg Lys Pro Asp Gly Ala Ile Tyr Thr Val Gly Ser
865                 870                 875                 880

Pro Ile Asp Tyr Gly Val Ile Val Asp Thr Lys Ala Tyr Ser Gly Gly
            885                 890                 895

Tyr Asn Leu Pro Ile Gly Gln Ala Asp Glu Met Gln Arg Tyr Val Glu
            900                 905                 910

Glu Asn Gln Thr Arg Asn Lys His Ile Asn Pro Asn Glu Trp Trp Lys
            915                 920                 925

Val Tyr Pro Ser Ser Val Thr Glu Phe Lys Phe Leu Phe Val Ser Gly
    930                 935                 940

His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
            965                 970                 975

Gly Glu Met Ile Lys Ala Gly Thr Leu Thr Leu Glu Val Arg Arg
            980                 985                 990

Lys Phe Asn Asn Gly Glu Ile Asn  Phe
    995                 1000

<210> SEQ ID NO 7
<211> LENGTH: 5115
<212> TYPE: DNA
<213> ORGANISM: Rhizopus oryzae
<220> FEATURE:
<223> OTHER INFORMATION: exonuclease gene

<400> SEQUENCE: 7
atgaaaatcc aagttgcttc tcctattgac caatccattg catatgaagt cagctgtctt      60
actcaggatc aagtcagcga tgctgtcgaa agatcccaaa tggccttctt gtcttggaaa     120
aaggtacctg tctcggatcg tgtggctatt atggaaaagt tttgtacact ttttgagcaa     180
aagaaggatg aggtagctaa atccatcacg tatcagatgg gacgtccaat tcgttatgga     240
cacggtgaag tcaagggagt tttggaaaga gcaagataca tgatatccgt agctgaagag     300
tgtatgaaag atactgtagt tgaacatacg ccgggtgttg ttaaaagatt tttacgcaag     360
gaacctttgg gtcctgtctt tattatcgct tcttggaatt acccttatct gacaacagtc     420
aataacgtga ttcctgctct tttggctggc aacactgtct tattgaagca gtcccctcaa     480
actccccagt gtgctgatat ctttgtggat accttgagag aggctggtgt gcccaaggat     540
gtcattcagg ctattcacgt tcaagataaa gaagctagct atcttgtgca acatcctttg     600
gttcaatttg ttaactttac cggaagtgtt gccgtcggta aaacgattag aaaagccatt     660
ggagattgtg aaaacctcat aggttgcggt atggaacttg gtggtaaaga tcctgcttat     720
gtcttacctg atcaaacttt ggattttgct gttgaaaaca tagtggatgg cgccttttc      780 aattctggac agtgctgctg ctctattgaa cgctgttatg ttcacaaaga tgtttatgat     840
```

```
gcatttgtag aaaaagcagt ggctttaact aagacttatg ttcttggtaa ccccgctcaa    900
ccagaaacta ctcttggtcc aatggctaat attaaatttg ccaatactgt cagaaaacat    960
ctgaaagatg ctattgaaaa aggagccaag cccttaatag aaccatttgc agaagacaag   1020
cctgacactg cttacgttgg ccctcaaata ttaatcaatg tcaaccatga tatgctggtg   1080
atgaaagaag aaacctttgg tcctgttttg cctatcatga agtgtcctc ggatgaagaa    1140 gcagtcaagc taatgaatga ttccaaatat ggcttaacag cttgtatttg gaccaccaac   1200
gaagaaagag cagtggaaat tggtgatcaa attgagactg gaacctggtt catgaatcgc   1260
tgtgattata tcgatcctgc tttagcctgg gtgggcgcaa aagagagtgg attgggattt   1320
tcaatgagta acaaggctt tagtcaatat acaagcgaac gctaccctat gtgttctgaa    1380
ctcattactg acaaggccat tccagaattt gacaatcttt atttggacat gaatggtatt   1440
gttcacaatt gctctcacaa taactctgat gatccgcatt acagaattac tgaagaacaa   1500
atctggcgag gcatctttca atacatggac cacctctttt caaaaatcaa acccaaaaaa   1560 ttgttttttcg tagctattga tggtgtggcg cctagagcca aaatgaacca gcaacgttct   1620
cgacgatttc gtacggccaa ggatgctgaa gacgcgcggc aaaaggcgtt ggctaagggc   1680
gaggaattgc ctgagcaaga cccatttgat accaattgta tcacacctgg aacggagttc   1740
atgattaaac ttacacagca attacgttat tttatttcaa agaaggtctc tgaggatgca   1800
gactggcgta atgttcaaat catcctgtca ggtcctgagg tacctggtga aggtgaacat   1860
aaaattatgg aatacattcg tttagctaag gctcagccgg attataaccc aaacacaaga   1920
cattgtttat atggcttgga tgctgacttg ttgatgctgg gtttattgag ccatgatccc   1980
cattttgctt tactacgtga agaagtaaca tttggtagaa accaaaagaa gaagataggt   2040
ttggataacc aaaacttta tctattacat ttatgtttaa taagagaata cctggatatg   2100
gaattcagtt cattgaaaac aaccctaccc ttcccatacg actttgaacg cgttgtagac   2160
gattttattt tacttgcgct gttcatcggt aacgatttct tgcctcattt acccaacatt   2220
catatcaacg aaggcgcctt gggtcttatg ttcaagatct ataaggagac attacccacc   2280
tgtgaaggat acttgcaaga cggtggtcgc gtagatatga caagacttca aaaggtacta   2340
gaccaaattt cagctgtggt agaaaaggaa gcttttgaag cagaaggcat cgacgcactc   2400
tatcttgctg gtaagcaacc agatggtgag cgcgcacgcg agattgtaca tcaattggaa   2460
cgcaagaagg caaagaaaa taaacaagc atgacagaac accaagcaga aattttttaga   2520 gccgtccggg atttcttgac aggtcctcct aagctcttgg cctctggttc cgtccttcgt   2580 ttctctttttc ctttcaagaa tcgcgataaa aactttataa agaaattggc caaggagctc   2640
aatatgaatc atatggtgac gtggcatcaa gcgcaaaaaa tgactgaact tgggctcatc   2700
ttctcgcatc aacttgatgc tgatgatcaa acctctgata caacgagtga gaatcagag    2760 atagatgaag aggctatagc cgctcgagac cgtgtattga aaagtatga gaatgcagat    2820 attgtgcctg aagacattga cagggaacag attgagaagg aagagaaggc gcaatttgag   2880
gccgcctttg agcaatggaa ggcagaatac tataaagaca agatgaatat cgatattggt   2940
gattctcagc aaatggaaaa actaataggc tcctatgtga ttggtattca atgggttctt   3000
cagtactatt ataatggtgt tgcctcctgg ggatggtttt atccttatca ctatgcccct   3060
aaaatttctg atcttaccaa cattgttcgt ttccaagacc acaccttac ccttggccaa    3120 cccttcaaac cctatgaaca gctcatgggt gtcttgccca tgctcagtaa aaagctacta   3180
```

```
cctgctgctt atcaagaact catgacagac cctagctcac ccatcattga ttttttaccct    3240 actgatttcg atatggacat gaacggcaag aaacaaagtt gggaagcaat tgtgaagatt    3300
cctttcattg atgaaaaacg cttgttggat gccatgaagt cacgagaaca tcgcttgact    3360
aaagatgaac gcgaaatggc tcgatttggt gaaagttacc gatttgtata cgatgattct    3420
attgccaaga aggaccccaa agagtggccg gtctacaaga gtcctttgcc tggcaagttc    3480
ccagatatcc gtccttgttt tgttcgagaa acagttgatt gtcttccaga gttacctagc    3540
actggattaa gaaaaggtct gttaccaggc gccaagacag gcaaggaagc gcttgctggt    3600
ttcccttcgc tccacactat caatcatcag tttcacattg ctaaccacaa tgttcgcgtg    3660
tttcaacagg acagctccaa tgaatctgtt gtggtcacca ttaaggatcg attcaaaagt    3720
gccaagttac atgagcttgc caagttgttt atttatcggt ctgtttatgt tggataccca    3780
tacttgaaac aagctgttgt tgttggtgtc tcgaatgcag agtgcaagtt gcacgtggtt    3840
ttggatgcac aaggcaaaaa acactgcaaa gaacatcgtt gggatgaacg ggaacgtgat    3900
gattggtata acactgtaca acgtctccag taccttcgca gcaaacgatt tggtcttttg    3960
gttggtgaaa cggagattgt ggctcatgtg tgtctcttga caggcatgca tcaaactgaa    4020
gaaggagcaa tggttaagca atatgcacac cctagtttgg ctgaagcaat tccattccag    4080
acgattgtga tcaaggtagc caatccagac cctcgatttg cagagttacc agctcctcct    4140
gttgagcaga gttaccctgt gggtacagct tgctttttga gcgacggtaa atttattggt    4200
acccaaacca aggtcattgg ctatactcga ggcaatatcg atgtcgagat ggaggtctac    4260
cgcgacaaga cgcttgagtc caaacccgaa tttggacatg cggttgcaaa gaacaagag     4320 cgagaggtca attatcttcc tggtcatgtc gtggctcgtg aatgcagcgt gtcttccttg    4380
acactatcca aattaacctc ttctctggtc gtcattgaac gctctggaca gaaattgaat    4440
attggtttga acttgaagtt tgagtctcga ggagaaaagg tacctggcta tacgcgcaag    4500
aaccctgagg ctggttactg ggagtactcg accctggctg ttcaattgat tcgtgaatac    4560
attacagctt tcccagagtt tattgaaatg ttgaatggta gaaagaatag ttcgatgatg    4620
gatgtttctg atttttggatg gacatcagaa ggacaaaagt atcttcatgc tatgaaggat    4680
tggatcaagg caaggaaggt gcatgatttg cctcgcgctc ctaatgaagc acaagaatta    4740
tatgatggat atgtccaact ggttgaaaag gctgcaaaga aattccaaga acagtgggat    4800
gctgaaccaa agaagactat tattatcaaa aacattcctc gcaagagttt actacgaccct   4860 tctgacgcac cttttaaact ggataatcaa acattcactt taggtgatcg agttgtttat    4920
gtatctgata caggtattgt ccctctcggt ctcaagggta caattgttgc tctttctgaa    4980
aagattattg atgtttttatt cgataaacct ttttttgggtg gaacaacatt gaatggaaga    5040
tgtcaagaat taagaggtgc agcactttca tcctggcagg ttatcaagtt tagtgtttct    5100
catgaaagaa gataa                                                     5115
```

<210> SEQ ID NO 8
<211> LENGTH: 1704
<212> TYPE: PRT
<213> ORGANISM: Rhizopus oryzae

<400> SEQUENCE: 8

Met Lys Ile Gln Val Ala Ser Pro Ile Asp Gln Ser Ile Ala Tyr Glu
1               5                   10                  15

Val Ser Cys Leu Thr Gln Asp Gln Val Ser Asp Ala Val Glu Arg Ser
            20                  25                  30

```
Gln Met Ala Phe Leu Ser Trp Lys Lys Val Pro Val Ser Asp Arg Val
         35                  40                  45

Ala Ile Met Glu Lys Phe Cys Thr Leu Phe Glu Gln Lys Lys Asp Glu
 50                  55                  60

Val Ala Lys Ser Ile Thr Tyr Gln Met Gly Arg Pro Ile Arg Tyr Gly
 65                  70                  75                  80

His Gly Glu Val Lys Gly Val Leu Glu Arg Ala Arg Tyr Met Ile Ser
                 85                  90                  95

Val Ala Glu Glu Cys Met Lys Asp Thr Val Val Glu His Thr Pro Gly
                100                 105                 110

Val Val Lys Arg Phe Leu Arg Lys Glu Pro Leu Gly Pro Val Phe Ile
            115                 120                 125

Ile Ala Ser Trp Asn Tyr Pro Tyr Leu Thr Thr Val Asn Asn Val Ile
130                 135                 140

Pro Ala Leu Leu Ala Gly Asn Thr Val Leu Leu Lys Gln Ser Pro Gln
145                 150                 155                 160

Thr Pro Gln Cys Ala Asp Ile Phe Val Asp Thr Leu Arg Glu Ala Gly
                165                 170                 175

Val Pro Lys Asp Val Ile Gln Ala Ile His Val Gln Asp Lys Glu Ala
            180                 185                 190

Ser Tyr Leu Val Gln His Pro Leu Val Gln Phe Val Asn Phe Thr Gly
        195                 200                 205

Ser Val Ala Val Gly Lys Thr Ile Arg Lys Ala Ile Gly Asp Cys Glu
    210                 215                 220

Asn Leu Ile Gly Cys Gly Met Glu Leu Gly Gly Lys Asp Pro Ala Tyr
225                 230                 235                 240

Val Leu Pro Asp Thr Asn Leu Asp Phe Ala Val Glu Asn Ile Val Asp
                245                 250                 255

Gly Ala Phe Phe Asn Ser Gly Gln Cys Cys Cys Ser Ile Glu Arg Cys
            260                 265                 270

Tyr Val His Lys Asp Val Tyr Asp Ala Phe Val Glu Lys Ala Val Ala
        275                 280                 285

Leu Thr Lys Thr Tyr Val Leu Gly Asn Pro Ala Gln Pro Glu Thr Thr
    290                 295                 300

Leu Gly Pro Met Ala Asn Ile Lys Phe Ala Asn Thr Val Arg Lys His
305                 310                 315                 320

Leu Lys Asp Ala Ile Glu Lys Gly Ala Lys Pro Leu Ile Glu Pro Phe
                325                 330                 335

Ala Glu Asp Lys Pro Asp Thr Ala Tyr Val Gly Pro Gln Ile Leu Ile
            340                 345                 350

Asn Val Asn His Asp Met Leu Val Met Lys Glu Glu Thr Phe Gly Pro
        355                 360                 365

Val Leu Pro Ile Met Lys Val Ser Ser Asp Glu Glu Ala Val Lys Leu
    370                 375                 380

Met Asn Asp Ser Lys Tyr Gly Leu Thr Ala Cys Ile Trp Thr Thr Asn
385                 390                 395                 400

Glu Glu Arg Ala Val Glu Ile Gly Asp Gln Ile Glu Thr Gly Thr Trp
                405                 410                 415

Phe Met Asn Arg Cys Asp Tyr Ile Asp Pro Ala Leu Ala Trp Val Gly
            420                 425                 430

Ala Lys Glu Ser Gly Leu Gly Phe Ser Met Ser Lys Gln Gly Phe Ser
        435                 440                 445
```

-continued

```
Gln Tyr Thr Ser Glu Arg Tyr Pro Met Cys Ser Glu Leu Ile Thr Asp
    450                 455                 460

Lys Ala Ile Pro Glu Phe Asp Asn Leu Tyr Leu Asp Met Asn Gly Ile
465                 470                 475                 480

Val His Asn Cys Ser His Asn Asn Ser Asp Asp Pro His Tyr Arg Ile
                485                 490                 495

Thr Glu Glu Gln Ile Trp Arg Gly Ile Phe Gln Tyr Met Asp His Leu
            500                 505                 510

Phe Ser Lys Ile Lys Pro Lys Lys Leu Phe Phe Val Ala Ile Asp Gly
        515                 520                 525

Val Ala Pro Arg Ala Lys Met Asn Gln Gln Arg Ser Arg Arg Phe Arg
530                 535                 540

Thr Ala Lys Asp Ala Glu Asp Ala Arg Gln Lys Ala Leu Ala Lys Gly
545                 550                 555                 560

Glu Glu Leu Pro Glu Gln Asp Pro Phe Asp Thr Asn Cys Ile Thr Pro
                565                 570                 575

Gly Thr Glu Phe Met Ile Lys Leu Thr Gln Gln Leu Arg Tyr Phe Ile
            580                 585                 590

Ser Lys Lys Val Ser Glu Asp Ala Asp Trp Arg Asn Val Gln Ile Ile
        595                 600                 605

Leu Ser Gly Pro Glu Val Pro Gly Glu Gly Glu His Lys Ile Met Glu
610                 615                 620

Tyr Ile Arg Leu Ala Lys Ala Gln Pro Asp Tyr Asn Pro Asn Thr Arg
625                 630                 635                 640

His Cys Leu Tyr Gly Leu Asp Ala Asp Leu Leu Met Leu Gly Leu Leu
                645                 650                 655

Ser His Asp Pro His Phe Ala Leu Leu Arg Glu Glu Val Thr Phe Gly
            660                 665                 670

Arg Asn Gln Lys Lys Lys Ile Gly Leu Asp Asn Gln Asn Phe Tyr Leu
        675                 680                 685

Leu His Leu Cys Leu Ile Arg Glu Tyr Leu Asp Met Glu Phe Ser Ser
690                 695                 700

Leu Lys Thr Thr Leu Pro Phe Pro Tyr Asp Phe Glu Arg Val Val Asp
705                 710                 715                 720

Asp Phe Ile Leu Leu Ala Leu Phe Ile Gly Asn Asp Phe Leu Pro His
                725                 730                 735

Leu Pro Asn Ile His Ile Asn Glu Gly Ala Leu Gly Leu Met Phe Lys
            740                 745                 750

Ile Tyr Lys Glu Thr Leu Pro Thr Cys Glu Gly Tyr Leu Gln Asp Gly
        755                 760                 765

Gly Arg Val Asp Met Thr Arg Leu Gln Lys Val Leu Asp Gln Ile Ser
770                 775                 780

Ala Val Val Glu Lys Glu Ala Phe Glu Ala Glu Gly Ile Asp Ala Leu
785                 790                 795                 800

Tyr Leu Ala Gly Lys Gln Pro Asp Gly Glu Arg Ala Arg Glu Ile Val
                805                 810                 815

His Gln Leu Glu Arg Lys Lys Ala Lys Glu Asn Lys Thr Ser Met Thr
            820                 825                 830

Glu His Gln Ala Glu Ile Phe Arg Ala Val Arg Asp Phe Leu Thr Gly
        835                 840                 845

Pro Pro Lys Leu Leu Ala Ser Gly Ser Val Leu Arg Phe Ser Phe
850                 855                 860

Phe Lys Asn Arg Asp Lys Asn Phe Ile Lys Lys Leu Ala Lys Glu Leu
```

```
                865              870              875              880
            Asn Met Asn His Met Val Thr Trp His Gln Ala Gln Lys Met Thr Glu
                            885              890              895
            Leu Gly Leu Ile Phe Ser His Gln Leu Asp Ala Asp Asp Gln Thr Ser
                            900              905              910
            Asp Thr Thr Ser Glu Glu Ser Glu Ile Asp Glu Glu Ala Ile Ala Ala
                            915              920              925
            Arg Asp Arg Val Leu Lys Lys Tyr Glu Asn Ala Asp Ile Val Pro Glu
                            930              935              940
            Asp Ile Asp Arg Glu Gln Ile Glu Lys Glu Glu Lys Ala Gln Phe Glu
            945              950              955              960
            Ala Ala Phe Glu Gln Trp Lys Ala Glu Tyr Tyr Lys Asp Lys Met Asn
                            965              970              975
            Ile Asp Ile Gly Asp Ser Gln Met Glu Lys Leu Ile Gly Ser Tyr
                            980              985              990
            Val Ile Gly Ile Gln Trp Val Leu  Gln Tyr Tyr Asn Gly Val Ala
                            995              1000             1005
            Ser Trp Gly Trp Phe Tyr Pro  Tyr His Tyr Ala Pro  Lys Ile Ser
                1010             1015              1020
            Asp Leu Thr Asn Ile Val Arg  Phe Gln Asp His Thr  Phe Thr Leu
                1025             1030              1035
            Gly Gln Pro Phe Lys Pro Tyr  Glu Gln Leu Met Gly  Val Leu Pro
                1040             1045              1050
            Met Leu Ser Lys Lys Leu Leu  Pro Ala Ala Tyr Gln  Glu Leu Met
                1055             1060              1065
            Thr Asp Pro Ser Ser Pro Ile  Ile Asp Phe Tyr Pro  Thr Asp Phe
                1070             1075              1080
            Asp Met Asp Met Asn Gly Lys  Lys Gln Ser Trp Glu  Ala Ile Val
                1085             1090              1095
            Lys Ile Pro Phe Ile Asp Glu  Lys Arg Leu Leu Asp  Ala Met Lys
                1100             1105              1110
            Ser Arg Glu His Arg Leu Thr  Lys Asp Glu Arg Glu  Met Ala Arg
                1115             1120              1125
            Phe Gly Glu Ser Tyr Arg Phe  Val Tyr Asp Asp Ser  Ile Ala Lys
                1130             1135              1140
            Lys Asp Pro Lys Glu Trp Pro  Val Tyr Lys Ser Pro  Leu Pro Gly
                1145             1150              1155
            Lys Phe Pro Asp Ile Arg Pro  Cys Phe Val Arg Glu  Thr Val Asp
                1160             1165              1170
            Cys Leu Pro Glu Leu Pro Ser  Thr Gly Leu Arg Lys  Gly Leu Leu
                1175             1180              1185
            Pro Gly Ala Lys Thr Gly Lys  Glu Ala Leu Ala Gly  Phe Pro Ser
                1190             1195              1200
            Leu His Thr Ile Asn His Gln  Phe His Ile Ala Asn  His Asn Val
                1205             1210              1215
            Arg Val Phe Gln Gln Asp Ser  Ser Asn Glu Ser Val  Val Val Thr
                1220             1225              1230
            Ile Lys Asp Arg Phe Lys Ser  Ala Lys Leu His Glu  Leu Ala Lys
                1235             1240              1245
            Leu Phe Ile Tyr Arg Ser Val  Tyr Val Gly Tyr Pro  Tyr Leu Lys
                1250             1255              1260
            Gln Ala Val Val Val Gly Val  Ser Asn Ala Glu Cys  Lys Leu His
                1265             1270              1275
```

-continued

Val Val Leu Asp Ala Gln Gly Lys Lys His Cys Lys Glu His Arg
1280            1285            1290

Trp Asp Glu Arg Glu Arg Asp Trp Tyr Asn Thr Val Gln Arg
1295            1300            1305

Leu Gln Tyr Leu Arg Ser Lys Arg Phe Gly Leu Leu Val Gly Glu
1310            1315            1320

Thr Glu Ile Val Ala His Val Cys Leu Leu Thr Gly Met His Gln
1325            1330            1335

Thr Glu Glu Gly Ala Met Val Lys Gln Tyr Ala His Pro Ser Leu
1340            1345            1350

Ala Glu Ala Ile Pro Phe Gln Thr Ile Val Ile Lys Val Ala Asn
1355            1360            1365

Pro Asp Pro Arg Phe Ala Glu Leu Pro Ala Pro Val Glu Gln
1370            1375            1380

Ser Tyr Pro Val Gly Thr Ala Cys Phe Leu Ser Asp Gly Lys Phe
1385            1390            1395

Ile Gly Thr Gln Thr Lys Val Ile Gly Tyr Thr Arg Gly Asn Ile
1400            1405            1410

Asp Val Glu Met Glu Val Tyr Arg Asp Lys Thr Leu Glu Ser Lys
1415            1420            1425

Pro Glu Phe Gly His Ala Val Ala Lys Lys Gln Glu Arg Glu Val
1430            1435            1440

Asn Tyr Leu Pro Gly His Val Val Ala Arg Glu Cys Ser Val Ser
1445            1450            1455

Ser Leu Thr Leu Ser Lys Leu Thr Ser Ser Leu Val Val Ile Glu
1460            1465            1470

Arg Ser Gly Gln Lys Leu Asn Ile Gly Leu Asn Leu Lys Phe Glu
1475            1480            1485

Ser Arg Gly Glu Lys Val Pro Gly Tyr Thr Arg Lys Asn Pro Glu
1490            1495            1500

Ala Gly Tyr Trp Glu Tyr Ser Thr Leu Ala Val Gln Leu Ile Arg
1505            1510            1515

Glu Tyr Ile Thr Ala Phe Pro Glu Phe Ile Glu Met Leu Asn Gly
1520            1525            1530

Arg Lys Asn Ser Ser Met Met Asp Val Ser Asp Phe Gly Trp Thr
1535            1540            1545

Ser Glu Gly Gln Lys Tyr Leu His Ala Met Lys Asp Trp Ile Lys
1550            1555            1560

Ala Arg Lys Val His Asp Leu Pro Arg Ala Pro Asn Glu Ala Gln
1565            1570            1575

Glu Leu Tyr Asp Gly Tyr Val Gln Leu Val Glu Lys Ala Ala Lys
1580            1585            1590

Lys Phe Gln Glu Gln Trp Asp Ala Glu Pro Lys Lys Thr Ile Ile
1595            1600            1605

Ile Lys Asn Ile Pro Arg Lys Ser Leu Leu Arg Pro Ser Asp Ala
1610            1615            1620

Pro Phe Lys Leu Asp Asn Gln Thr Phe Thr Leu Gly Asp Arg Val
1625            1630            1635

Val Tyr Val Ser Asp Thr Gly Ile Val Pro Leu Gly Leu Lys Gly
1640            1645            1650

Thr Ile Val Ala Leu Ser Glu Lys Ile Ile Asp Val Leu Phe Asp
1655            1660            1665

```
Lys Pro Phe Leu Gly Gly Thr Thr Leu Asn Gly Arg Cys Gln Glu
    1670            1675                1680

Leu Arg Gly Ala Ala Leu Ser Ser Trp Gln Val Ile Lys Phe Ser
    1685            1690                1695

Val Ser His Glu Arg Arg
    1700

<210> SEQ ID NO 9
<211> LENGTH: 18
<212> TYPE: DNA
<213> ORGANISM: Rhizopus delemar
<220> FEATURE:
<223> OTHER INFORMATION: Target of LeftTALEN-pdc

<400> SEQUENCE: 9
tgcctgctat taaaatcg                                                18

<210> SEQ ID NO 10
<211> LENGTH: 18
<212> TYPE: DNA
<213> ORGANISM: Rhizopus delemar
<220> FEATURE:
<223> OTHER INFORMATION: Target of RightTALEN-pdc

<400> SEQUENCE: 10
ttgatttcct taagacgg                                                18

<210> SEQ ID NO 11
<211> LENGTH: 34
<212> TYPE: PRT
<213> ORGANISM: Artificial Sequence
<220> FEATURE:
<223> OTHER INFORMATION: 1st repeat of LeftTALEN-pdc

<400> SEQUENCE: 11

Leu Thr Pro Asp Gln Val Val Ala Ile Ala Asn Asn Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 12
<211> LENGTH: 34
<212> TYPE: PRT
<213> ORGANISM: Artificial Sequence
<220> FEATURE:
<223> OTHER INFORMATION: 2nd repeat of LeftTALEN-pdc

<400> SEQUENCE: 12

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 13
<211> LENGTH: 34
<212> TYPE: PRT
<213> ORGANISM: Artificial Sequence
<220> FEATURE:
<223> OTHER INFORMATION: 3rd repeat of LeftTALEN-pdc

<400> SEQUENCE: 13
```

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 14
<211> LENGTH: 34
<212> TYPE: PRT
<213> ORGANISM: Artificial Sequence
<220> FEATURE:
<223> OTHER INFORMATION: 4th repeat of LeftTALEN-pdc

<400> SEQUENCE: 14

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 15
<211> LENGTH: 34
<212> TYPE: PRT
<213> ORGANISM: Artificial Sequence
<220> FEATURE:
<223> OTHER INFORMATION: 5th repeat of LeftTALEN-pdc

<400> SEQUENCE: 15

Leu Thr Pro Asp Gln Val Val Ala Ile Ala Asn Asn Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 16
<211> LENGTH: 34
<212> TYPE: PRT
<213> ORGANISM: Artificial Sequence
<220> FEATURE:
<223> OTHER INFORMATION: 6th repeat of LeftTALEN-pdc

<400> SEQUENCE: 16

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 17
<211> LENGTH: 34
<212> TYPE: PRT
<213> ORGANISM: Artificial Sequence
<220> FEATURE:
<223> OTHER INFORMATION: 7th repeat of LeftTALEN-pdc

<400> SEQUENCE: 17

Leu Thr Pro Ala Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 18
<211> LENGTH: 34
<212> TYPE: PRT
<213> ORGANISM: Artificial Sequence
<220> FEATURE:
<223> OTHER INFORMATION: 8th repeat of LeftTALEN-pdc

<400> SEQUENCE: 18

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 19
<211> LENGTH: 34
<212> TYPE: PRT
<213> ORGANISM: Artificial Sequence
<220> FEATURE:
<223> OTHER INFORMATION: 9th repeat of LeftTALEN-pdc

<400> SEQUENCE: 19

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 20
<211> LENGTH: 34
<212> TYPE: PRT
<213> ORGANISM: Artificial Sequence
<220> FEATURE:
<223> OTHER INFORMATION: 10th repeat of LeftTALEN-pdc

<400> SEQUENCE: 20

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 21
<211> LENGTH: 34
<212> TYPE: PRT
<213> ORGANISM: Artificial Sequence
<220> FEATURE:
<223> OTHER INFORMATION: 11th repeat of LeftTALEN-pdc

<400> SEQUENCE: 21

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 22
<211> LENGTH: 34
<212> TYPE: PRT
<213> ORGANISM: Artificial Sequence
<220> FEATURE:

```
<223> OTHER INFORMATION: 12th repeat of LeftTALEN-pdc

<400> SEQUENCE: 22

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 23
<211> LENGTH: 34
<212> TYPE: PRT
<213> ORGANISM: Artificial Sequence
<220> FEATURE:
<223> OTHER INFORMATION: 13th repeat of LeftTALEN-pdc

<400> SEQUENCE: 23

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 24
<211> LENGTH: 34
<212> TYPE: PRT
<213> ORGANISM: Artificial Sequence
<220> FEATURE:
<223> OTHER INFORMATION: 14th repeat of LeftTALEN-pdc

<400> SEQUENCE: 24

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 25
<211> LENGTH: 34
<212> TYPE: PRT
<213> ORGANISM: Artificial Sequence
<220> FEATURE:
<223> OTHER INFORMATION: 15th repeat of LeftTALEN-pdc

<400> SEQUENCE: 25

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 26
<211> LENGTH: 34
<212> TYPE: PRT
<213> ORGANISM: Artificial Sequence
<220> FEATURE:
<223> OTHER INFORMATION: 16th repeat of LeftTALEN-pdc

<400> SEQUENCE: 26

Leu Thr Pro Asp Gln Val Val Ala Ile Ala Ser His Asp Gly Gly Lys
1               5                   10                  15
```

Gln Ala Leu Glu Thr Val Gln Arg Leu Leu Pro Val Leu Cys Gln Ala
            20                  25                  30

His Gly

<210> SEQ ID NO 27
<211> LENGTH: 20
<212> TYPE: PRT
<213> ORGANISM: Artificial Sequence
<220> FEATURE:
<223> OTHER INFORMATION: 17th repeat of LeftTALEN-pdc

<400> SEQUENCE: 27

Leu Thr Pro Glu Gln Val Val Ala Ile Ala Asn Asn Asn Gly Gly Arg
1               5                   10                  15

Pro Ala Leu Glu
            20

<210> SEQ ID NO 28
<211> LENGTH: 34
<212> TYPE: PRT
<213> ORGANISM: Artificial Sequence
<220> FEATURE:
<223> OTHER INFORMATION: 1st repeat of RightTALEN-pdc

<400> SEQUENCE: 28

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 29
<211> LENGTH: 34
<212> TYPE: PRT
<213> ORGANISM: Artificial Sequence
<220> FEATURE:
<223> OTHER INFORMATION: 2nd repeat of RightTALEN-pdc

<400> SEQUENCE: 29

Leu Thr Pro Asp Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 30
<211> LENGTH: 34
<212> TYPE: PRT
<213> ORGANISM: Artificial Sequence
<220> FEATURE:
<223> OTHER INFORMATION: 3rd repeat of RightTALEN-pdc

<400> SEQUENCE: 30

Leu Thr Pro Ala Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 31
<211> LENGTH: 34
<212> TYPE: PRT

```
<213> ORGANISM: Artificial Sequenc
<220> FEATURE:
<223> OTHER INFORMATION: 4th repeat of RightTALEN-pdc

<400> SEQUENCE: 31

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 32
<211> LENGTH: 34
<212> TYPE: PRT
<213> ORGANISM: Artificial Sequenc
<220> FEATURE:
<223> OTHER INFORMATION: 5th repeat of RightTALEN-pdc

<400> SEQUENCE: 32

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 33
<211> LENGTH: 34
<212> TYPE: PRT
<213> ORGANISM: Artificial Sequenc
<220> FEATURE:
<223> OTHER INFORMATION: 6th repeat of RightTALEN-pdc

<400> SEQUENCE: 33

Leu Thr Pro Asp Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 34
<211> LENGTH: 34
<212> TYPE: PRT
<213> ORGANISM: Artificial Sequenc
<220> FEATURE:
<223> OTHER INFORMATION: 7th repeat of RightTALEN-pdc

<400> SEQUENCE: 34

Leu Thr Pro Ala Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 35
<211> LENGTH: 34
<212> TYPE: PRT
<213> ORGANISM: Artificial Sequenc
<220> FEATURE:
<223> OTHER INFORMATION: 8th repeat of RightTALEN-pdc

<400> SEQUENCE: 35

Leu Thr Pro Asp Gln Val Val Ala Ile Ala Ser His Asp Gly Gly Lys
```

-continued

```
                1               5                  10                 15
Gln Ala Leu Glu Thr Val Gln Arg Leu Leu Pro Val Leu Cys Gln Asp
            20                  25                 30

His Gly

<210> SEQ ID NO 36
<211> LENGTH: 34
<212> TYPE: PRT
<213> ORGANISM: Artificial Sequenc
<220> FEATURE:
<223> OTHER INFORMATION: 9th repeat of RightTALEN-pdc

<400> SEQUENCE: 36

Leu Thr Pro Asp Gln Val Val Ala Ile Ala Ser Asn Gly Gly Gly Lys
1               5                  10                 15

Gln Ala Leu Glu Thr Val Gln Arg Leu Leu Pro Val Leu Cys Gln Asp
            20                  25                 30

His Gly

<210> SEQ ID NO 37
<211> LENGTH: 34
<212> TYPE: PRT
<213> ORGANISM: Artificial Sequenc
<220> FEATURE:
<223> OTHER INFORMATION: 10th repeat of RightTALEN-pdc

<400> SEQUENCE: 37

Leu Thr Pro Asp Gln Val Val Ala Ile Ala Ser Asn Gly Gly Gly Lys
1               5                  10                 15

Gln Ala Leu Glu Thr Val Gln Arg Leu Leu Pro Val Leu Cys Gln Ala
            20                  25                 30

His Gly

<210> SEQ ID NO 38
<211> LENGTH: 34
<212> TYPE: PRT
<213> ORGANISM: Artificial Sequenc
<220> FEATURE:
<223> OTHER INFORMATION: 11th repeat of RightTALEN-pdc

<400> SEQUENCE: 38

Leu Thr Pro Asp Gln Val Val Ala Ile Ala Ser Asn Ile Gly Gly Lys
1               5                  10                 15

Gln Ala Leu Glu Thr Val Gln Arg Leu Leu Pro Val Leu Cys Gln Asp
            20                  25                 30

His Gly

<210> SEQ ID NO 39
<211> LENGTH: 34
<212> TYPE: PRT
<213> ORGANISM: Artificial Sequenc
<220> FEATURE:
<223> OTHER INFORMATION: 12th repeat of RightTALEN-pdc

<400> SEQUENCE: 39

Leu Thr Pro Asp Gln Val Val Ala Ile Ala Ser Asn Ile Gly Gly Lys
1               5                  10                 15

Gln Ala Leu Glu Thr Val Gln Arg Leu Leu Pro Val Leu Cys Gln Ala
            20                  25                 30

His Gly
```

<210> SEQ ID NO 40
<211> LENGTH: 34
<212> TYPE: PRT
<213> ORGANISM: Artificial Sequenc
<220> FEATURE:
<223> OTHER INFORMATION: 13th repeat of RightTALEN-pdc

<400> SEQUENCE: 40

Leu Thr Pro Ala Gln Val Val Ala Ile Ala Asn Asn Asn Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 41
<211> LENGTH: 34
<212> TYPE: PRT
<213> ORGANISM: Artificial Sequenc
<220> FEATURE:
<223> OTHER INFORMATION: 14th repeat of RightTALEN-pdc

<400> SEQUENCE: 41

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 42
<211> LENGTH: 34
<212> TYPE: PRT
<213> ORGANISM: Artificial Sequenc
<220> FEATURE:
<223> OTHER INFORMATION: 15th repeat of RightTALEN-pdc

<400> SEQUENCE: 42

Leu Thr Pro Asp Gln Val Val Ala Ile Ala Ser His Asp Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 43
<211> LENGTH: 34
<212> TYPE: PRT
<213> ORGANISM: Artificial Sequenc
<220> FEATURE:
<223> OTHER INFORMATION: 16th repeat of RightTALEN-pdc

<400> SEQUENCE: 43

Leu Thr Pro Asp Gln Val Val Ala Ile Ala Asn Asn Asn Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 44
<211> LENGTH: 20
<212> TYPE: PRT
<213> ORGANISM: Artificial Sequenc
<220> FEATURE:
<223> OTHER INFORMATION: 17th repeat of RightTALEN-pdc

```
<400> SEQUENCE: 44

Leu Thr Pro Glu Gln Val Val Ala Ile Ala Asn Asn Asn Gly Gly Arg
1               5                   10                  15

Pro Ala Leu Glu
            20

<210> SEQ ID NO 45
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 45
cgagctcgaa ttatttaaat gaacagcaag ttaataatct agaggg                      46

<210> SEQ ID NO 46
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 46
tatgaccatg attacgatga gaggcaaaat gaagcgtac                              39

<210> SEQ ID NO 47
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 47
atttaaataa ttcgagctcg gtacccgggg                                        30

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
cgtaatcatg gtcatagctg                                                   20

<210> SEQ ID NO 49
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 49
tagagggaaa aagagagaat tgaaatagg                                         29

<210> SEQ ID NO 50
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 50
```

```
ttttgttatt taattgtatt aattgataat g                              31
```

<210> SEQ ID NO 51
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 51

```
aattaaataa caaaatcatt ttaattacgc attttc                         36
```

<210> SEQ ID NO 52
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 52

```
catgattacg cggccgcgcc attataatgc actagtg                        37
```

<210> SEQ ID NO 53
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 53

```
ctcttttcc ctctaatgag aggcaaaatg aagcgtac                        38
```

<210> SEQ ID NO 54
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 54

```
atttaaatgt aatcatggtc atagctgttt c                              31
```

<210> SEQ ID NO 55
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 55

```
tttaaattag agggaaaaag agagaattga aatag                          35
```

<210> SEQ ID NO 56
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 56

```
tccctctaat ttaaatgaat tcgagctcgg taccc                          35
```

<210> SEQ ID NO 57
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 57
ttttgttatt taattgtatt aattgataat g                                       31

<210> SEQ ID NO 58
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 58
tcattttaat tacgcatttt catttac                                            27

<210> SEQ ID NO 59
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 59
aattaaataa caaaatgga ctacaaagac catgacggtg                               40

<210> SEQ ID NO 60
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 60
gcgtaattaa aatgattaaa agtttatctc gccgttatta                              40

<210> SEQ ID NO 61
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 61
gggtaccgag ctcgaattc                                                     19

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
ggggatcctc tagagtcgac                                                    20

<210> SEQ ID NO 63
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 63
ctctagagga tcccctaggt gtggctgtgg tgaccatatt g                            41

<210> SEQ ID NO 64
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 64
gagaattata ttgtaaagaa aaataaag                                    28

<210> SEQ ID NO 65
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 65
tacaatataa ttctcatgaa aatccaagtt gcttctccta ttgaccaatc            50

<210> SEQ ID NO 66
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 66
atgaattcta agattttatc ttctttcatg agaaacacta aacttgataa c          51

<210> SEQ ID NO 67
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 67
aatcttagaa ttcatctttt tttg                                        24

<210> SEQ ID NO 68
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 68
tcgagctcgg tacccactct accgtctgct cttttgtct                        39

<210> SEQ ID NO 69
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 69
ctgcaggtcg actctagagg atccccgggt accg                             34

<210> SEQ ID NO 70
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 70
gcttggcact ggccgtcgtt ttacaacgtc gtgac                                35

<210> SEQ ID NO 71
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 71
cggccagtgc caagcgcaga cttcaacagt tggcttttt aagta                      45

<210> SEQ ID NO 72
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 72
cattttgcct ctcatgtttt taaatttgtt ttgtagagta ttgaata                   47

<210> SEQ ID NO 73
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 73
gaacagcaag ttaataatct agagggcgc                                       29

<210> SEQ ID NO 74
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 74
atgagaggca aaatgaagcg tacaaagag                                       29

<210> SEQ ID NO 75
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 75
attaacttgc tgttcaatct tagaattcat ttttttttg tatcattcg                  49

<210> SEQ ID NO 76
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 76
agagtcgacc tgcaggcgtc aataagagct tgaaggttgg tgccggatc                 49

<210> SEQ ID NO 77

```
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 77
gcagacttca acagttggct tttttaagta                                30

<210> SEQ ID NO 78
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 78
gcgtcaataa gagcttgaag gttggtgccg gatc                           34

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 79
cattcccaca ggatttgtgc                                           20

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 80
gtgagatgtt gatcatttgt acatg                                     25

<210> SEQ ID NO 81
<211> LENGTH: 3735
<212> TYPE: DNA
<213> ORGANISM: Rhizopus delemar
<220> FEATURE:
<223> OTHER INFORMATION: region including pdc gene

<400> SEQUENCE: 81
gcagacttca acagttggct tttttaagta aaaaagatag tgtttctcga taaattaatt    60
ttgataagat aaagagagag agagaatgaa acgatacttt ttgtttattt tttcgtgaat   120
aaaaaaaagt cattccactt ttagaaacca agagtagtgt tcttgacaac aacgccattt   180
ttttgcgtag tcttaaaaaa aaagtcattc gttttttgaag gaatacaacg gatctgatta   240
aggaaggcag tagattcaat ttgattggat aaagttcatc ttccgaaatc gactttatg   300 tgtcattgta tttgggcgca taaaagtaat aacgggatgt tccactgcgt tcggttatca   360
gttttaatat cagaaatcat acatgttttt tttatatta cttatcccga aatatctatt   420
gtctcctccg taggctgact tgctgtcaat gtcaaataag gtatggctgt agtacattct   480
atgcacgttc tataaagtaa tttactagtt taaagcaaaa aacatgagca aaagaagcct   540
gatatgcttt ggttttcatt tcatttgaac gtattctttc tttttttttt tgcagagtat   600 ttttatgcg tttttttttt tttttttttt ttttactac gatcaaagat atcttcgatt   660
acagaaacag aaagggattt gccggagtat gaatacttgt cttttaattt tattctttga   720
```

```
aagaagcata aagaataaac tgatggtacg gtgtttatct gttcacaagt actggtaagc    780
aacatacttg tttttaaggaa acattaaact ctatttgcca gctattgaaa gaaagaaaga    840
aaaaatatgc attttaattc tccgatgctt tcgggcacag tcgttattag gtatcgattt    900
gctgatatga cattgcgacg aaaatagtat aaaagaaacc cactctttt tcgttcaaaa    960 aaaatcatta ttcaatactc tacaaaacaa atttaaaaac atgcctgcta ttaaaatcgg   1020
tcaacatctc cttaaccgtc ttaaggaaat caacattgat gttgtctttg gtgttcctgg   1080
tgatttcaac atggtaagca gacaattgaa ttgaacgaga gcctataaac ttattatttc   1140 tatagcccctt gttggatatc attgaagatg acccagaact tacctggggt aacaatgcca   1200
acgaattgaa tgcatcttat gcagctgatg gttatgctcg tattcgtggt gcaggtgctg   1260
ttgtcactac ctttggtgta ggtgagctgt ctgctgtcaa cggtattgct ggttcatact   1320
ctgagatgct tcccgtgatt cacatcgtcg gtactccttc tactaaatcc caagctgccg   1380
gtgccatgct tcaccactct ttgggtacgg gtaactttga tgtgttcttc aacatgtcct   1440
ccatgattgc ctgtgcctct gctcacctca agaaacaaac ggccattgca gaaattgacc   1500
gtgtgatctc ccaagctgtt ctctccaagc gtacaggtta cattggtatc cctatcgatc   1560
tgatcaagac tgaggttgaa gtacctgagc ccattcctgc cctcaagacc gaattaccca   1620 aaacccagc tgatgtccaa gcgattgcct tgagagtggt cacggatgcg atcgccaaag   1680
cccaattccc tgtgattgtt gtcgatggct gtgtgcttcg ccagagatgc caaaaggcag   1740
tacaagcctt tatcgaacgt actggttttcc ctacttatgt tgctcctatg ggtaagggtg   1800
ccgttgacga atcctctgtg agttaccgtg gctgctactc gggtaatgtc acattggaag   1860
cagtgaatga agagatcaag caagccgatt tgatcatcga agtgggctcc atcaagtctg   1920 attttcaacac gggtaactttt tcatactctc tcgaccgttc caagacgatc accttgcact   1980
cctttgccac catcgtgttt tgtgctgaat accaaaaggt ctccatgctc gaattcattc   2040
ctctcttgac ccaagcccctt cccgaacaac cccgtcaatt caacctgggt ccccgcccaa   2100
gacccgtacc tatccaaccc ggtaccgaaa tcacccacaa ctactttttgg cacaaggtac   2160 ccgaattcat ggatgagaac gccattgtct gtgccgagac cggtacagct gaatttgctt   2220
cactcaacat ggacggaccc aagggaacga cttatatcac ccaattcctc tggggctcta   2280
tcggtttctc agtaggtgcc gctgtgggtg ctgcgatcgc cgctcgtgat cgtcgtgtgt   2340
atctctttgt cggtgatggt tccttccaat tgacctgtca agaaatctct ggcttccttc   2400
gccatggttt gacacctgtg atcttcttgc tgaacaatga cggttacttg atcgaaaaac   2460
tcattcacgg tcccgaacgt gcctataata actttcaaat gtgggaatac agcaagacgc   2520
ttgattattt cggtgctcat cttgaacaca acaagtccat gggtgttcct cccgttggct   2580
tcgaaggcaa ggtagccaca cgcgatgaat ttgaatccgc catgagacag gttcaagcca   2640
atcctgacaa gattcatttc cttgaagtca ttatgcctca atttgactct cctcgtgaac   2700
ttgaactctt ggttgccaac tctgaaaacc gttaaaatct tagaattcat ttttttttttg   2760 tatcattcgt tctatacttc attactacag taaattcata ataaaatcat atttttgaaa   2820
ataagctttt tttttctttt acctgtgggc cccatgatga ttggtgtaac ttttacaagc   2880
tttggattgc caagttttat cagcatgtga caagtcagca cacgctcttg aatattcta   2940 ggcaacaagg ctttgatttc ttttagggac ttggtttata ttgaatccctt ttaaggattg   3000 tatttaaaaa tagtttttatt gcaagaaatg atgtatgtat gggtgtttgt tacaatgtaa   3060
```

| | |
|---|---:|
| ataggcatga aaatatatac aacaagaaaa aacggtctat aaagtctata agcattcaat | 3120 |
| aaaatgaatt attattcgtc atggccacaa ggacaagatt catcgtgagt gaactgagag | 3180 |
| acatcgattc cacaaccagg acagaaggca tattcataaa gaaatgtaaa ttgaaccaag | 3240 |
| tttagtgagt ccatgttttt gattgtaaaa ggataaggaa agaaagaga cagtttgaga | 3300 |
| agcaaccttt ttataaacat attccttcaa ccaaggtcat tcattcccta aactattttc | 3360 |
| cttgtgtggc aaaagtacgc cggcagagac ggataaatat gcttgcgctc tcttttgact | 3420 |
| tgtacaactc taatttgttt gtgctaagca tcgatggggg tccacttttta gccattgttt | 3480 |
| gttataggcc ttggcattgt ctattaataa attagaaaaa gagcagacga gagagagaga | 3540 |
| gagagagtga agggggggggg accatctgat ctgtctttac aagtcacatc tatgacaatt | 3600 |
| tttatgcctt ttttgagaaa aaaaaatcta tttttttttat ccttccttct tactctttca | 3660 |
| cagcatgtcc catcttccga ccatcgtcgt cctcatttct ggatccggca ccaaccttca | 3720 |
| agctcttatt gacgc | 3735 |

<210> SEQ ID NO 82
<211> LENGTH: 5772
<212> TYPE: DNA
<213> ORGANISM: Rhizopus oryzae
<220> FEATURE:
<223> OTHER INFORMATION: exonuclease gene

<400> SEQUENCE: 82

| | |
|---|---:|
| atgaaaatcc aagttgcttc tcctattgac caatccattg catatgaagt cagctgtctt | 60 |
| actcaggatc aagtcagcga tgctgtcgaa agatcccaaa tggccttctt gtcttggaaa | 120 |
| aaggtacctg tctcggatcg tgtggctatt atggaaaagt tttgtacact ttttgagcaa | 180 |
| aagaaggatg aggtagctaa atccatcacg tatcagatgg acgtccaat tcgttatgga | 240 |
| cacggtgaag tcaagggagt tttggaaaga gcaagataca tgatatccgt agctgaagag | 300 |
| tgtatgaaaa tactgtagt tgaacatacg ccgggtgttg ttaaaagatt tttacgcaag | 360 |
| gaaccttttgg gtcctgtctt tattatcgct tcttggaatt acccttatct gacaacagtc | 420 |
| aataacgtga ttcctgctct tttggctggc aacactgtct tattgaagca gtcccctcaa | 480 |
| actccccagt gtgctgatat cttttgtggat accttgagag aggctggtgt gcccaaggat | 540 |
| gtcattcagg ctattcacgt tcaagataaa gaagctagct atcttgtgca acatcctttg | 600 |
| gttcaatttg ttaactttac cggaagtgtt gccgtcggta aaacgattag aaaagccatt | 660 |
| ggagattgtg aaaaccctcat aggtattgag aggagctata tttatttgat cgtgtactga | 720 |
| tacacaaaat acaggttgcg gtatggaact tggtggtaaa gatcctgctt atgtcttacc | 780 |
| tgatacaaac ttggattttg ctgttgaaaa catagtggat ggcgcctttt tcaattctgg | 840 |
| acagtgctgc tgctctattg aacgctgtta tgttcacaaa gatgtttatg atgcatttgt | 900 |
| agaaaaagca gtggctttaa ctaaggtaga gcatacaatc ttaattatgt aaagttaaaa | 960 |
| taaaatcata atagacttat gttcttggta accccgctca accagaaact actcttggtc | 1020 |
| caatggctaa tattaaattt gccaatactg tcagaaaaca tctgaaagat gctattgaaa | 1080 |
| aaggagccaa gccctaaata gaaccatttg cagaagacaa gcctgacact gcttacgttg | 1140 |
| gccctcaaat attaatcaat gtcaaccatg atatgctggt gatgaaagaa gaaacctttg | 1200 |
| gtcctgtttt gcctatcatg aaagtgtcct cggatgaaga agcagtcaag ctaatgaatg | 1260 |
| attccaaata tggcttaaca gcttgtattt ggaccaccaa cgaagaaaga gcagtggaaa | 1320 |
| ttggtgatca aattgagact ggaacctggt tcatgaatcg ctgtgattat atcgatcctg | 1380 |

```
ctttagcctg ggtgggcgca aaagagagtg gattgggatt ttcaatgagt aaacaaggct    1440
ttagtcaata tacaaggtaa aaaaaaaaaa aaaaaaaaag tttttggagc taataatagt    1500
attaatagac ctaagtccta tcaccttaaa ttgtcgcagc agtaactttt gcaagcctat    1560
tggttcaaac gtaactcctg taaaaataaa gcgacgcagt taaattttcc gtatttcctg    1620
tttttttttt tgcttttttct cttgttaaca agaaaataa gatgggaatt cccaaatttt    1680
tccgatggat taggtacatt tttgaacaaa caatctttg ctatgtttgc cattaatata    1740
cctatttttt tttgacaatc agcgaacgct accctatgtg ttctgaactc attactgaca    1800
aggccattcc agaatttggt tagtttatta ttactataag tcctaccgtg tttcttaaac    1860
aatatgcatt tttttattta caaagacaa tctttatttg gacatgaatg gtattgttca    1920
caattgctct cacaataact ctgatgatcc gcattacaga attactgaag aacaaatctg    1980
gcgaggcatc tttcaataca tggaccacct cttttcaaaa atcaaaccca aaaaattgtt    2040
tttcgtagct attgatggtg tggcgcctag agccaaaatg aaccagcaac gttctcgacg    2100
atttcgtacg gccaaggatg ctgaagacgc gcggcaaaag gcgttggcta agggcgagga    2160
attgcctgag caagacccat ttgataccaa ttgtatcaca cctggaacgg agttcatgat    2220
taaacttaca cagcaattac gttatttat ttcaaagaag gtctctgagg atgcagactg    2280
gcgtaatgtt caaatcatcc tgtcaggtcc tgaggtacct ggtgaaggtg aacataaaat    2340
tatggaatac attcgtttag ctaaggctca gccggattat aacccaaaca caagacattg    2400
tttatatggc ttggatgctg acttgttgat gctgggttta ttgagccatg atccccattt    2460
tgctttacta cgtgaagaag taacatttgg tagaaaccaa aagaagaaga tagggtaaga    2520
aagtgaagga aaataggatg tgtgttttat tgaccttttt atttcatcta tagtttggat    2580
aaccaaaact tttatctatt acatttatgt ttaataagag aatacctgga tatggaattc    2640
agttcattga aaacaacccct acccttccca tacgactttg aacgcgttgt agacgatttt    2700
attttacttg cgctgttcat cggtaacgat ttcttgcctc atttacccaa cattcatatc    2760
aacgaaggcg ccttgggtct tatgttcaag atctataagg agacattacc cacctgtgaa    2820
ggatacttgc aagacggtgg tcgcgtagat atgacaagac ttcaaaaggt actagaccaa    2880
atttcagctg tggtagaaaa ggaagctttt gaagcagaag gcatcgacgc actctatctt    2940
gctggtaagc aaccagatgg tgagcgcgca cgcgagattt acatcaatt ggaacgcaag    3000 aaggcaaaag aaaataaaac aagcatgaca gaacaccaag cagaaatttt tagagccgtc    3060
cgggatttct tgacaggtcc tcctaagctc ttggcctctg gttccgtcct tcgtttctct    3120
tttcctttca agaatcgcga taaaaacttt ataagaaat tggccaagga gctcaatatg    3180
aatcatatgt tgacgtggca tcaagcgcaa aaaatgactg aacttgggct catcttctcg    3240
catcaacttg atgctgatga tcaaacctct gatacaacga gtgaagaatc agagatagat    3300
gaagaggcta tagccgctcg agaccgtgta ttgaaaagt atgagaatgc agatattgtg    3360
cctgaagaca ttgacaggga acagattgag aaggaagaga aggcgcaatt tgaggccgcc    3420
tttgagcaat ggaaggcaga atactataaa gacaagatga atatcgatat tggtgattct    3480
cagcaaatgg aaaaactaat aggctcctat gtgattggta ttcaatgggt tcttcagtac    3540
tattataatg gtgttgcctc ctggggatgg ttttatcctt atcactatgc ccctaaaatt    3600
tctgatctta ccaacattgt tcgttttccaa gaccacacct ttacccttgg ccaacccttc    3660
aaaccctatg aacagctcat gggtgtcttg cccatgctca gtaaaaagct actacctgct    3720
```

```
gcttatcaag aactcatgac agaccctagc tcacccatca ttgatttta ccctactgat   3780
ttcgatatgg acatgaacgg caagaaacaa agttgggaag caattgtgaa gattcctttc   3840
attgatgaaa aacgcttgtt ggatgccatg aagtcacgag aacatcgctt gactaaagat   3900
gaacgcgaaa tggctcgatt tggtgaaagt taccgatttg tatacgatga ttctattgcc   3960
aagaaggacc ccaaagagtg gccggtctac aagagtcctt tgcctggcaa gttcccagat   4020
atccgtcctt gttttgttcg agaaacagtt gattgtcttc cagagttacc tagcactgga   4080
ttaagaaaag gtctgttacc aggcgccaag acaggcaagg aagcgcttgc tggtttccct   4140
tcgctccaca ctatcaatca tcagtttcac attgctaacc acaatgttcg cgtgtttcaa   4200
caggacagct ccaatgaatc tgttgtggtc accattaagg atcgattcaa aagtgccaag   4260
ttacatgagc ttgccaagtt gtttatttat cggtctgttt atgttggata cccatacttg   4320
aaacaagctg ttgttgttgg tgtctcgaat gcagagtgca agttgcacgt ggttttggat   4380
gcacaaggca aaaacactg caaagaacat cgttgggatg aacgggaacg tgatgattgg   4440
tataacactg tacaacgtct ccagtacctt cgcagcaaac gatttggtct tttgttggt   4500
gaaacggaga ttgtggctca tgtgtgtctc ttgacaggca tgcatcaaac tgaagaagga   4560
gcaatggtta agcaatatgc acccctagt ttggctgaag caattccatt ccagacgatt   4620
gtgatcaagg tagccaatcc agaccctcga tttgcagagt taccagctcc tcctgttgag   4680
cagagttacc ctgtgggtac agcttgcttt ttgagcgacg gtaaatttat tggtacccaa   4740
accaaggtca ttggctatac tcgaggcaat atcgatgtcg agatggaggt ctaccgcgac   4800
aagacgcttg agtccaaacc cgaatttgga catgcggttg caaagaaaca agagcgagag   4860
gtcaattatc ttcctggtca tgtcgtggct cgtgaatgca gcgtgtcttc cttgacacta   4920
tccaaattaa cctcttctct ggtcgtcatt gaacgctctg gacagaaatt gaatattggt   4980
ttgaacttga gtttgagtc tcgaggagaa aaggtacctg gctatacgcg caagaaccct   5040
gaggctggtt actgggagta ctcgaccctg gctgttcaat tgattcgtga atacattaca   5100
gctttcccag agtttattga aatgttgaat ggtagaaaga atagttcgat gatggatgtt   5160
tctgattttg gatggacatc agaaggacaa aagtatcttc atgctatgaa ggattggatc   5220
aaggcaagga aggtgcatga tttgcctcgc gctcctaatg aagcacaaga attatatgat   5280
gtaaagtagc ttttttcctt ttttttttct tagatttctc aatatttgtt tttattttgt   5340
tagggatatg tccaactggt tgaaaaggct gcaaagaaat tccaagaaca gtgggatgct   5400
gaaccaaaga agactattat tatcaaaaac attcctcgca agagtttact acgaccttct   5460
gacgcaccctt taaactgga taatcaaaca ttcactttag gtgatcgagt tgtttatgta   5520
tctgatacag gtattgtccc tctcggtctc aagggtacaa ttgttgctct ttctgaaaag   5580
attattgatg ttttattcga taaaccttt ttgggtggaa caacattgaa tggaaggtat   5640
ataagaaaaa aagaaaaaa aaagcaaca gacatcttaa ataactttgt gtgtagatgt   5700
caagaattaa gaggtgcagc actttcatcc tggcaggtta tcaagtttag tgtttctcat   5760
gaaagaagat aa                                                      5772
```

<210> SEQ ID NO 83
<211> LENGTH: 1749
<212> TYPE: DNA
<213> ORGANISM: Rhizopus delemar;
<220> FEATURE:
<223> OTHER INFORMATION: pdc3 gene

<400> SEQUENCE: 83

```
atggttagta tcaaaattgg agattatctc attcaacgtc ttaaagaaac cggaatcgac    60 acgattttg gtgttccagg tgattacaat atggtaagtt acgaagtgga tacagattta   120
tttgaatgtg tgtatatcct gaaaaacttt gcaatgtagc cgctattgga tttaattgaa   180
gatgattctg agctcatatg gggtaataat gcaaacgaac tcaatgcttc ctatgctgct   240
gatggctatg ctcgtatcag aggctttggt gctgtagtta ccacgtttgg tgtaggggaa   300 cttctgctg cagcaggtat tgctggatct tattctgaaa aagtcccagt acttcatatt   360
gtcggcactc ctaatactaa atcccaggaa gctggagcta ttcttcatca cacgcttggt   420
aatggcaatt tcaggtgtt tgttgaaatg ttttccatga tcacgtgtgc ttctactcat   480
ttaaactttg acaatgccat ccgagaaatt gatcgcgtca tccagcagac tatgattcga   540
aagcgacctg gttatatcgg catccccatt gatctgatta atgctgaggt tgctcttcct   600
agttctgaac ctctcaattt ttttgtcccc aaaaatccta ctcaaactca agatgtggct   660
cttaaggttg ttttggacgc tatttcacag gctaagcatc cgattatagt tgttgatgca   720
tgtgttcagc gacacaattt agttcaagag gctattgaat tcgtgaaacg taccggtttt   780 ccacttacg ttgcacctat gggtaaaggt attgttcccg aggatcttgt caattatcgt   840
ggttgctatg ctggtaatat taccatcgag ggtatcgcca gggaacttga gcaagctgat   900
ctggtcattg aacttggtgc gattaaatcc gatttcaaca ctggtggctt cacctataaa   960
ctggatcctg ctagaacgat ctctcttcac tcatttggta cccagatatt ttatgccgac  1020
tatgacaaag tgggaatgac ggaatttctt cctctttga ccaagtctct tcctcaaagg  1080
cctcgtgtat ttgatctagg ccctcgtcat gagccagatc caattcaatc aggaactgaa  1140
ataacgcaca attatttctg gaataaggta ccagaataca tggatcctcg cgctgttgtt  1200
gttgctgaaa caggcacagc tgaatttgcc tcttttaatt taagagctcc caaagacgct  1260
ctctttattt ctcaagtact ctggggatcc atcggttttg ctgtcggatg tgctgtcggt  1320
gctgcgttcg ctgatcgaga tcgacgagtt tatctttttg tgggtgatgg ctctttccag  1380
gttacttgtc aagaaatttc agtcttttg catcaagggt tgacacctgt cattttcttg  1440
ttgaacaatg atggatacct tatcgaaaaa ctcattcatg ggcctcaccg ctcttataat  1500
aactttcaga tgtggaacta cagcaaaact cttgactata tgggtggaca tcttcagcgc  1560
aatctgtctg atgtttcgcc agctcaagtt ggtgttgaag ctcaagtccg tacgcgagat  1620
gagtttgaga gggcaatgaa gacagtcaag gaggaacgta acaaaattca ttttattgaa  1680
gttgtcatgc ctcaatttga tgctcctcgc gaattgatac tccaagttca aacttctgaa  1740
aatcgttaa                                                          1749
```

<210> SEQ ID NO 84
<211> LENGTH: 3075
<212> TYPE: DNA
<213> ORGANISM: Artificial
<220> FEATURE:
<223> OTHER INFORMATION: LeftTALEN-pdc3

<400> SEQUENCE: 84

```
atgggaaaac ctattcctaa tcctctgctg ggcctggatt ctaccggagg catggcccct    60
aagaaaaagc ggaaggtgga cggcggagtg gacctgagaa cactgggata ttctcagcag   120
cagcaggaga agatcaagcc caaggtgaga tctacagtgg cccagcacca cgaagccctg   180
gtgggacacg gatttacaca cgcccacatt gtggccctgt ctcagcaccc tgccgccctg   240
```

```
ggaacagtgg ccgtgaaata tcaggatatg attgccgccc tgcctgaggc cacacacgaa    300
gccattgtgg gagtgggaaa acgaggcgct ggagccagag ccctggaagc cctgctgaca    360
gtggccggag aactgagagg acctcctctg cagctggata caggacagct gctgaagatt    420
gccaaaaggg gcggagtgac cgcggtggaa gccgtgcacg cctggagaaa tgccctgaca    480
ggagcccctc tgaacctgac ccccgaacag gtggtggcca ttgccagcca cgacggcggc    540
aagcaggccc tggaaaccgt gcagagactg ctgcccgtgc tgtgccaggc ccatggcctg    600
acacctgaac aggtggtggc tatcgcctct aacaacggag aaaacaggc tctggaaaca    660 gtgcagcggc tgctgcctgt gctgtgtcag gctcacggct tgactccaga acaggtggtg    720
gctattgctt ccaacaacgg ggggaaacag gccctggaaa ctgtgcagcg cctgctgcca    780
gtgctgtgcc aggctcacgg actgaccccc gaacaggtgg tggccattgc cagcaacatc    840
ggcggcaagc aggccctgga aaccgtgcag agactgctgc ccgtgctgtg ccaggcccat    900
ggcctgacac ctgaacaggt ggtggctatc gcctctaata tcggaggaaa acaggctctg    960
gaaacagtgc agcggctgct gcctgtgctg tgtcaggctc acggcttgac tccagaacag   1020
gtggtggcta ttgcttccaa cggcgggggg aaacaggccc tggaaactgt gcagcgcctg   1080
ctgccagtgc tgtgccaggc tcacgggctg accccgaac aggtggtggc cattgccagc   1140
cacgacggcg gcaagcaggc cctggaaacc gtgcagagac tgctgcccgt gctgtgccag   1200
gcccatggcc tgacacctga acaggtggtg gctatcgcct ctaacaacgg aggaaaacag   1260
gctctggaaa cagtgcagcg gctgctgcct gtgctgtgtc aggctcacgg cttgactcca   1320
gaacaggtgg tggctattgc ttccaatatt ggggggaaac aggccctgga aactgtgcag   1380
cgcctgctgc cagtgctgtg ccaggctcac ggcctcactc ccgaacaggt ggtggccatt   1440
gccagccacg acggcggcaa gcaggccctg gaaaccgtgc agagactgct gcccgtgctg   1500
tgccaggccc atggcctgac acctgaacag gtggtggcta tcgcctctaa tatcggagga   1560
aaacaggctc tggaaacagt gcagcggctg ctgcctgtgc tgtgtcaggc tcacggcttg   1620
actccagaac aggtggtggc tattgcttcc cacgacgggg gaaacaggc cctggaaact   1680 gtgcagcgc tgctgccagt gctgtgccag gctcacggac tgaccccga caggtggtg   1740 gccattgcca gcaacaacgg cggcaagcag gccctggaaa ccgtgcagag actgctgccc   1800
gtgctgtgcc aggcccatgg cctgacacct gaacaggtgg tggctatcgc ctctaatatc   1860
ggaggaaaac aagcactcga gacagtgcag cggctgctgc ctgtgctgtg tcaggctcac   1920
ggcttgactc cagaacaggt ggtggctatt gcttccaacg gcgggggaa acaggccctg   1980 gaaactgtgc agcgcctgct gccagtgctg tgccaggctc acgggctgac ccccgaacag   2040
gtggtggcca ttgccagcaa cggcggcggc aagcaggccc tggaaaccgt gcagagactg   2100
ctgcccgtgc tgtgccaggc ccatggcctg acacctgaac aggtggtggc tatcgcctct   2160
aacggcggag aaaacaggc tctggaaaca gtgcagcggc tgctgcctgt gctgtgtcag   2220
gctcacggct tgactccaca gcaggtcgtg gcaattgcta gcaacggcgg cggacggccc   2280
gccctggaga gcattgtggc ccagctgtct agacctgatc ctgccctggc cgccctgaca   2340
aatgatcacc tggtggccct ggcctgtctg ggaggcagac ctgccctgga tgccgtgaaa   2400
aaaggactgc ctcacgcccc ctgccctgatc aagagaacaa atagaagaat ccccgagcgg   2460
acctctcaca gagtggccgg atcccagctg gtgaaatctg agctggagga agaagtct   2520 gagctgagac acaagctgaa gtacgtgcct cacgagtaca tcgagctgat cgagatcgcc   2580
agaaatagca cccaggatag aatcctggag atgaaggtga tggagttctt catgaaggtg   2640
```

| | |
|---|---|
| tacggctaca gaggaaagca cctgggagga agcagaaaac ctgacggagc catttataca | 2700 |
| gtgggcagcc ctatcgatta tggcgtgatc gtggatacaa aggcctacag cggaggctac | 2760 |
| aatctgccta ttggacaggc cgatgagatg cagagatacg tggaggagaa ccagaccagg | 2820 |
| aacaagcaca tcaaccctaa cgagtggtgg aaggtgtacc cttctagcgt gaccgagttc | 2880 |
| aagttcctgt ttgtgagcgg ccacttcaag ggcaattata aggcccagct gaccaggctg | 2940 |
| aaccacatca caaattgtaa tggcgccgtg ctgtctgtgg aggaactgct gattggagga | 3000 |
| gagatgatta aggccggaac actgacactg gaggaggtga agaaagttt caacaacggc | 3060 |
| gagatcaact tctga | 3075 |

<210> SEQ ID NO 85
<211> LENGTH: 3075
<212> TYPE: DNA
<213> ORGANISM: Artificial
<220> FEATURE:
<223> OTHER INFORMATION: RightTALEN-pdc3

<400> SEQUENCE: 85

| | |
|---|---|
| atgggaaaac ctattcctaa tcctctgctg ggcctggatt ctaccggagg catggcccct | 60 |
| aagaaaaagc ggaaggtgga cggcggagtg gacctgagaa cactgggata ttctcagcag | 120 |
| cagcaggaga agatcaagcc caaggtgaga tctacagtgg cccagcacca cgaagccctg | 180 |
| gtgggacacg gatttacaca cgcccacatt gtggccctgt ctcagcaccc tgccgccctg | 240 |
| ggaacagtgg ccgtgaaata tcaggatatg attgccgccc tgcctgaggc cacacacgaa | 300 |
| gccattgtgg gagtgggaaa acgaggcgct ggagccagag ccctggaagc cctgctgaca | 360 |
| gtggccggag aactgagagg acctcctctg cagctggata caggacagct gctgaagatt | 420 |
| gccaaagggg gcggagtgac cgcggtggaa gccgtgcacg cctggagaaa tgccctgaca | 480 |
| ggagcccctc tgaacctgac ccccgaacag gtggtggcca ttgccagcaa caacggcggc | 540 |
| aagcaggccc tggaaaccgt gcagagactg ctgcccgtgc tgtgccaggc catggcctg | 600 |
| acacctgaac aggtggtggc tatcgcctct aacggcggag aaaacaggc tctgaaaaca | 660 |
| gtgcagcggc tgctgcctgt gctgtgtcag gctcacggct tgactccaga acaggtggtg | 720 |
| gctattgctt ccaatattgg ggggaaacag gccctggaaa ctgtgcagcg cctgctgcca | 780 |
| gtgctgtgcc aggctcacgg actgaccccc gaacaggtgg tggccattgc cagcaacatc | 840 |
| ggcggcaagc aggccctgga aaccgtgcag agactgctgc ccgtgctgtg ccaggcccat | 900 |
| ggcctgacac ctgaacaggt ggtggctatc gcctctcacg acggaggaaa acaggctctg | 960 |
| gaaacagtgc agcggctgct gcctgtgctg tgtcaggctc acggcttgac tccagaacag | 1020 |
| gtggtggcta ttgcttccaa cggcgggggg aaacaggccc tggaaactgt gcagcgcctg | 1080 |
| ctgccagtgc tgtgccaggc tcacgggctg accccgaac aggtggtggc cattgccagc | 1140 |
| aacggcggcg gcaagcaggc cctggaaacc gtgcagagac tgctgcccgt gctgtgccag | 1200 |
| gcccatggcc tgacacctga acaggtggtg gctatcgcct ctaatatcgg aggaaaacag | 1260 |
| gctctggaaa cagtgcagcg gctgctgcct gtgctgtgtc aggctcacgg cttgactcca | 1320 |
| gaacaggtgg tggctattgc ttcccacgac gggggggaaa aggccctgga aactgtgcag | 1380 |
| cgcctgctgc cagtgctgtg ccaggctcac ggcctcactc ccgaacaggt ggtggccatt | 1440 |
| gccagcacg acggcggcaa gcaggccctg gaaaccgtgc agagactgct gcccgtgctg | 1500 |
| tgccaggccc atggcctgac acctgaacag gtggtggcta tcgcctctaa tatcggagga | 1560 |

```
aaacaggctc tggaaacagt gcagcggctg ctgcctgtgc tgtgtcaggc tcacggcttg    1620
actccagaac aggtggtggc tattgcttcc aacggcgggg ggaaacaggc cctggaaact    1680
gtgcagcgcc tgctgccagt gctgtgccag gctcacggac tgaccccgga acaggtggtg    1740
gccattgcca gcaacatcgg cggcaagcag gccctggaaa ccgtgcagag actgctgccc    1800
gtgctgtgcc aggcccatgg cctgacacct gaacaggtgg tggctatcgc ctctaacggc    1860
ggaggaaaac aagcactcga gacagtgcag cggctgctgc tgtgctgtg tcaggctcac    1920 ggcttgactc cagaacaggt ggtggctatt gcttccaacg gcgggggaa acaggccctg    1980 gaaactgtgc agcgcctgct gccagtgctg tgccaggctc acgggctgac ccccgaacag    2040
gtggtggcca ttgccagcaa caacggcggc aagcaggccc tggaaaccgt gcagagactg    2100
ctgcccgtgc tgtgccaggc ccatggcctg acacctgaac aggtggtggc tatcgcctct    2160
aacggcggag gaaaacaggc tctggaaaca gtgcagcggc tgctgcctgt gctgtgtcag    2220
gctcacggct tgactccaca gcaggtcgtg gcaattgcta gcaatatcgg cggacggccc    2280
gccctggaga gcattgtggc ccagctgtct agacctgatc ctgccctggc cgccctgaca    2340
aatgatcacc tggtggccct ggcctgtctg ggaggcagac ctgccctgga tgccgtgaaa    2400
aaaggactgc ctcacgcccc tgccctgatc aagagaacaa atagaagaat ccccgagcgg    2460
acctctcaca gagtggccgg atcccagctg gtgaaatctg agctggagga agaagtct    2520 gagctgagac acaagctgaa gtacgtgcct cacgagtaca tcgagctgat cgagatcgcc    2580
agaaatagca cccaggatag aatcctggag atgaaggtga tggagttctt catgaaggtg    2640
tacggctaca gaggaaagca cctgggagga agcagaaaac ctgacggagc catttataca    2700
gtgggcagcc ctatcgatta tggcgtgatc gtggatacaa aggcctacag cggaggctac    2760
aatctgccta ttggacaggc cgatgagatg cagagatacg tggaggagaa ccagaccagg    2820
aacaagcaca tcaaccctaa cgagtggtgg aaggtgtacc cttctagcgt gaccgagttc    2880
aagttcctgt ttgtgagcgg ccacttcaag ggcaattata aggcccagct gaccaggctg    2940
aaccacatca caaattgtaa tggcgccgtg ctgtctgtgg aggaactgct gattggagga    3000
gagatgatta aggccggaac actgacactg gaggaggtga aagaaagtt caacaacggc    3060 gagatcaact tctga                                                    3075
```

```
<210> SEQ ID NO 86
<211> LENGTH: 19
<212> TYPE: DNA
<213> ORGANISM: Rhizopus delemar
<220> FEATURE:
<223> OTHER INFORMATION: Target of LeftTALEN-pdc3

<400> SEQUENCE: 86
ccggaatcga cacgatttt                                                  19

<210> SEQ ID NO 87
<211> LENGTH: 19
<212> TYPE: DNA
<213> ORGANISM: Rhizopus delemar
<220> FEATURE:
<223> OTHER INFORMATION: Target of RightTALEN-pdc3

<400> SEQUENCE: 87
cgtaacttac catattgta                                                  19

<210> SEQ ID NO 88
<211> LENGTH: 29
```

```
<212> TYPE: DNA
<213> ORGANISM: Artificial
<220> FEATURE:
<223> OTHER INFORMATION: trpCter-R

<400> SEQUENCE: 88
atgagaggca aaatgaagcg tacaaagag                                   29

<210> SEQ ID NO 89
<211> LENGTH: 40
<212> TYPE: DNA
<213> ORGANISM: Artificial
<220> FEATURE:
<223> OTHER INFORMATION: trpCter-cicCpro-F

<400> SEQUENCE: 89
cattttgcct ctcatcttac gcaggttgat agtagccgcc                       40

<210> SEQ ID NO 90
<211> LENGTH: 40
<212> TYPE: DNA
<213> ORGANISM: Artificial
<220> FEATURE:
<223> OTHER INFORMATION: cipCpro-adhter-R

<400> SEQUENCE: 90
gcgtaattaa aatgaggtta gagtatgaag aaaaaaaaaa                       40

<210> SEQ ID NO 91
<211> LENGTH: 31
<212> TYPE: DNA
<213> ORGANISM: Artificial
<220> FEATURE:
<223> OTHER INFORMATION: trpC-lost-F2

<400> SEQUENCE: 91
tttaaatctt acgcaggttg atagtagccg c                                31

<210> SEQ ID NO 92
<211> LENGTH: 33
<212> TYPE: DNA
<213> ORGANISM: Artificial
<220> FEATURE:
<223> OTHER INFORMATION: trpC-lost-R2

<400> SEQUENCE: 92
tgcgtaagat ttaaatgaat tcgagctcgg tac                              33

<210> SEQ ID NO 93
<211> LENGTH: 29
<212> TYPE: DNA
<213> ORGANISM: Artificial
<220> FEATURE:
<223> OTHER INFORMATION: cipCpro-R

<400> SEQUENCE: 93
ggttagagta tgaagaaaaa aaaaaaacg                                   29

<210> SEQ ID NO 94
<211> LENGTH: 45
<212> TYPE: DNA
<213> ORGANISM: Artificial
<220> FEATURE:
<223> OTHER INFORMATION: cipCpro-LifeTALEN-F

<400> SEQUENCE: 94
```

```
cttcatactc taaccatggg aaaacctatt cctaatcctc tgctg                    45

<210> SEQ ID NO 95
<211> LENGTH: 47
<212> TYPE: DNA
<213> ORGANISM: Artificial
<220> FEATURE:
<223> OTHER INFORMATION: LifeTALEN-adhter-R

<400> SEQUENCE: 95
gcgtaattaa aatgatcaga agttgatctc gccgttgttg aactttc                  47

<210> SEQ ID NO 96
<211> LENGTH: 40
<212> TYPE: DNA
<213> ORGANISM: Artificial
<220> FEATURE:
<223> OTHER INFORMATION: cipCpro-exo1-F

<400> SEQUENCE: 96
cttcatactc taaccatgaa aatccaagtt gcttctccta                          40

<210> SEQ ID NO 97
<211> LENGTH: 40
<212> TYPE: DNA
<213> ORGANISM: Artificial
<220> FEATURE:
<223> OTHER INFORMATION: exo1-adhter-R

<400> SEQUENCE: 97
gcgtaattaa aatgattatc ttctttcatg agaaacacta                          40

<210> SEQ ID NO 98
<211> LENGTH: 40
<212> TYPE: DNA
<213> ORGANISM: Artificial
<220> FEATURE:
<223> OTHER INFORMATION: pdc3-upstr-F

<400> SEQUENCE: 98
cggccagtgc caagcccgtc aggggtgaat gagatatttt                          40

<210> SEQ ID NO 99
<211> LENGTH: 33
<212> TYPE: DNA
<213> ORGANISM: Artificial
<220> FEATURE:
<223> OTHER INFORMATION: pdc3-upstr-R2

<400> SEQUENCE: 99
aaaagatgtg agttataaaa ggatgatgca agc                                 33

<210> SEQ ID NO 100
<211> LENGTH: 33
<212> TYPE: DNA
<213> ORGANISM: Artificial
<220> FEATURE:
<223> OTHER INFORMATION: pdc3-downstr-F2

<400> SEQUENCE: 100
taactcacat cttttattct ttttctatcc ctc                                 33

<210> SEQ ID NO 101
<211> LENGTH: 40
<212> TYPE: DNA
<213> ORGANISM: Artificial
```

```
<220> FEATURE:
<223> OTHER INFORMATION: pdc3-downstr-R

<400> SEQUENCE: 101
agagtcgacc tgcagacctg ttagaaaggt acatgcattc                              40

<210> SEQ ID NO 102
<211> LENGTH: 40
<212> TYPE: DNA
<213> ORGANISM: Artificial
<220> FEATURE:
<223> OTHER INFORMATION: pdc3-upstr-R

<400> SEQUENCE: 102
cattttgcct ctcatgtgag ttataaaagg atgatgcaag                              40

<210> SEQ ID NO 103
<211> LENGTH: 40
<212> TYPE: DNA
<213> ORGANISM: Artificial
<220> FEATURE:
<223> OTHER INFORMATION: pdc3-downstr-F

<400> SEQUENCE: 103
attaacttgc tgttcatctt ttattctttt tctatccctc                              40

<210> SEQ ID NO 104
<211> LENGTH: 23
<212> TYPE: DNA
<213> ORGANISM: Artificial
<220> FEATURE:
<223> OTHER INFORMATION: pdc3-upstr-F2

<400> SEQUENCE: 104
ccgtcagggg tgaatgagat att                                                23

<210> SEQ ID NO 105
<211> LENGTH: 25
<212> TYPE: DNA
<213> ORGANISM: Artificial
<220> FEATURE:
<223> OTHER INFORMATION: pdc3-downstr-R2-P

<400> SEQUENCE: 105
acctgttaga aaggtacatg cattc                                              25

<210> SEQ ID NO 106
<211> LENGTH: 21
<212> TYPE: DNA
<213> ORGANISM: Artificial
<220> FEATURE:
<223> OTHER INFORMATION: pdc3-up

<400> SEQUENCE: 106
gacctcaatc actatccttg g                                                  21
```